(12) United States Patent
Sucholeiki

(10) Patent No.: US 8,765,953 B2
(45) Date of Patent: *Jul. 1, 2014

(54) COMPOUNDS AND METHODS FOR THE TREATMENT OF PAIN AND OTHER DISEASES

(75) Inventor: Irving Sucholeiki, Winchester, MA (US)

(73) Assignee: Aquilus Pharmaceuticals, Inc., Winchester, MA (US)

(*) Notice: Subject to any disclaimer, the term of this patent is extended or adjusted under 35 U.S.C. 154(b) by 258 days.

This patent is subject to a terminal disclaimer.

(21) Appl. No.: 13/141,384

(22) PCT Filed: Dec. 21, 2009

(86) PCT No.: PCT/US2009/069005
§ 371 (c)(1),
(2), (4) Date: Jun. 22, 2011

(87) PCT Pub. No.: WO2010/075287
PCT Pub. Date: Jul. 1, 2010

(65) Prior Publication Data
US 2011/0257222 A1    Oct. 20, 2011

Related U.S. Application Data

(60) Provisional application No. 61/203,548, filed on Dec. 23, 2008, provisional application No. 61/214,863, filed on Apr. 29, 2009.

(51) Int. Cl.
*C07D 221/02* (2006.01)
*C07D 209/04* (2006.01)
*C07D 209/20* (2006.01)

(52) U.S. Cl.
USPC .......................... 546/112; 548/469; 548/496

(58) Field of Classification Search
None
See application file for complete search history.

(56) References Cited

U.S. PATENT DOCUMENTS

| | | | |
|---|---|---|---|
| 6,150,394 A | 11/2000 | Watanabe et al. | |
| 6,221,335 B1* | 4/2001 | Foster | 424/1.81 |
| 6,440,710 B1* | 8/2002 | Keinan et al. | 435/148 |
| 6,603,008 B1* | 8/2003 | Ando et al. | 546/269.7 |
| 2006/0025596 A1* | 2/2006 | Ito et al. | 546/184 |
| 2007/0082929 A1* | 4/2007 | Gant et al. | 514/338 |
| 2007/0197695 A1* | 8/2007 | Potyen et al. | 524/110 |
| 2008/0221195 A1 | 9/2008 | Wortmann et al. | |
| 2008/0261994 A1 | 10/2008 | Inaba et al. | |

FOREIGN PATENT DOCUMENTS

| | | |
|---|---|---|
| EP | 1283210 A1 | 4/2001 |
| EP | 12705569 A1 | 1/2003 |
| WO | 00/15213 Z1 | 3/2000 |

OTHER PUBLICATIONS

Gouyette (Biomedical and Environmental Mass Spectrometry, 1988, 15, 243-247).*
Baillie (Pharmacology Rev.1981; 33: 81-132).*
Browne (Journal of Clinical Pharmacology, 1998, 38: 213-220).*
Wolen (Journal of Clinical Pharmacology, 1986, 26: 419-424).*
Haskins (Biomedical Spectrometry, 1982, vol. 9, issue 7, pp. 269-277).*
Tonn (Biological Mass Spectrometry, 1993, vol. 22, issue 11, pp. 633-642).*
International Search Report and Written Opinion dated Aug. 17, 2010 for PCT/US09/69005.
Chiappori, A.A. et al. "A phase I pharmacokinetic and pharmacodynamic study of S-3304, a novel matrix metalloproteinase inhibitor, in patients with advanced and refactory solid tumors." Clin. Cancer Res. 2007, 13(7) 2091-2099.
Mant, T.G.K. et al. "Pharmacokinetics and safety assessments of high-dose and 4-week treatment with S-3304, a novel matrix metalloproteinase inhibitor, in healthy volunteers." Br. J. Clin. Pharmacol. 2006, 63(5) 512-526.
Kushner, D.J. et al. Pharmacological uses and perspectives of heavy water and deuterated compounds. Can J Physiol Pharmacol. 1999;77:79-88.
Extended European Search Report for Application No. EP09835701.5 dated Jun. 6, 2013.
Translation of first Office Action issued in Application No. RU 2011130381 dated Oct. 7, 2013.
Tamura, Y. et al. Highly selective and orally active inhibitors of type IV collagenase (MMP-9 and MMP-2): N-sulfonylamino acid derivatives. J Med Chem. Feb. 12, 1998;41(4):640-9.
Kiyama, R. et al. Homology modeling of gelatinase catalytic domains and docking simulations of novel sulfonamide inhibitors. J Med Chem. May 20, 1999;42(10):1723-38.
Translation of first Office Action dated Jul. 25, 2013 for Chinese Patent Application No. 200980157184X.

* cited by examiner

*Primary Examiner* — Sreeni Padmanabhan
*Assistant Examiner* — Uma Ramachandran
(74) *Attorney, Agent, or Firm* — Burns & Levinson LLP; Jacob N. Erlich

(57) ABSTRACT

The present invention relates generally to alkyne containing pharmaceutical agents, and in particular, to phenylethynyl-thiophene based metalloprotease inhibitor compounds. More particularly, the present invention provides a new class of MMP inhibiting compounds that exhibit increased potency, metabolic stability and/or reduced toxicity in relation to currently known MMP inhibitors for the treatment of pain and other diseases such as cancer. Additionally, the present invention relates to methods for treating pain in a patient comprising administering to the patient a pain-reducing effective amount of a present compound.

2 Claims, 2 Drawing Sheets

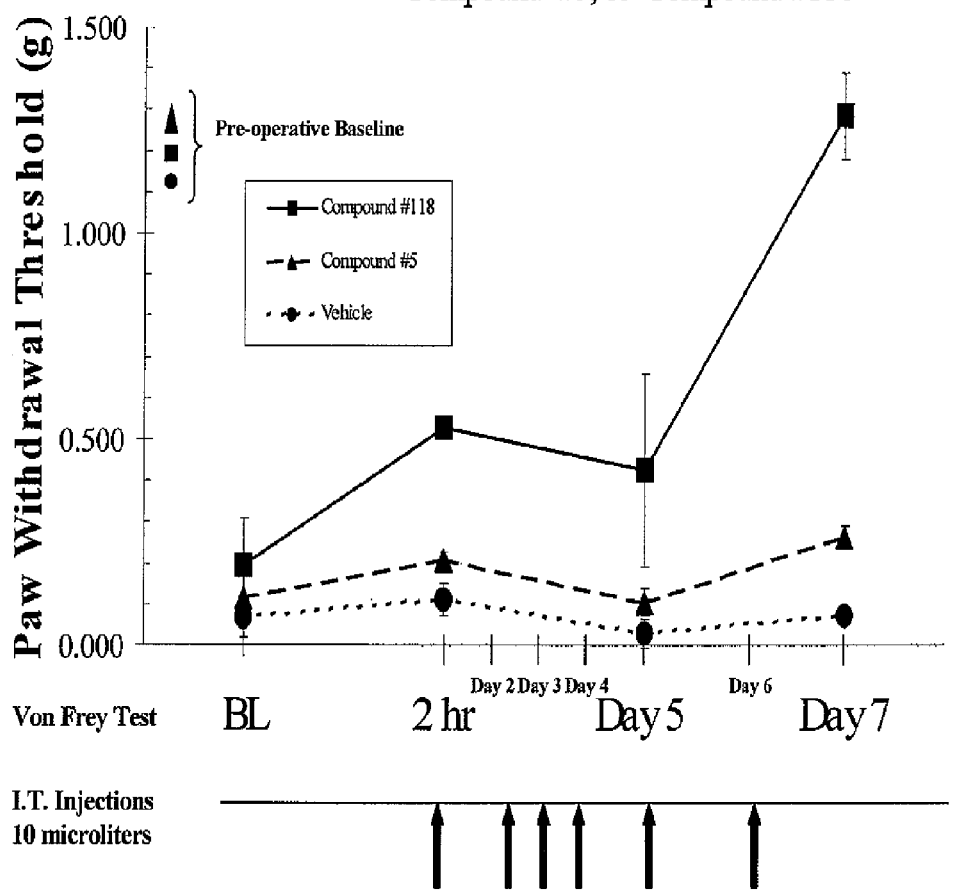

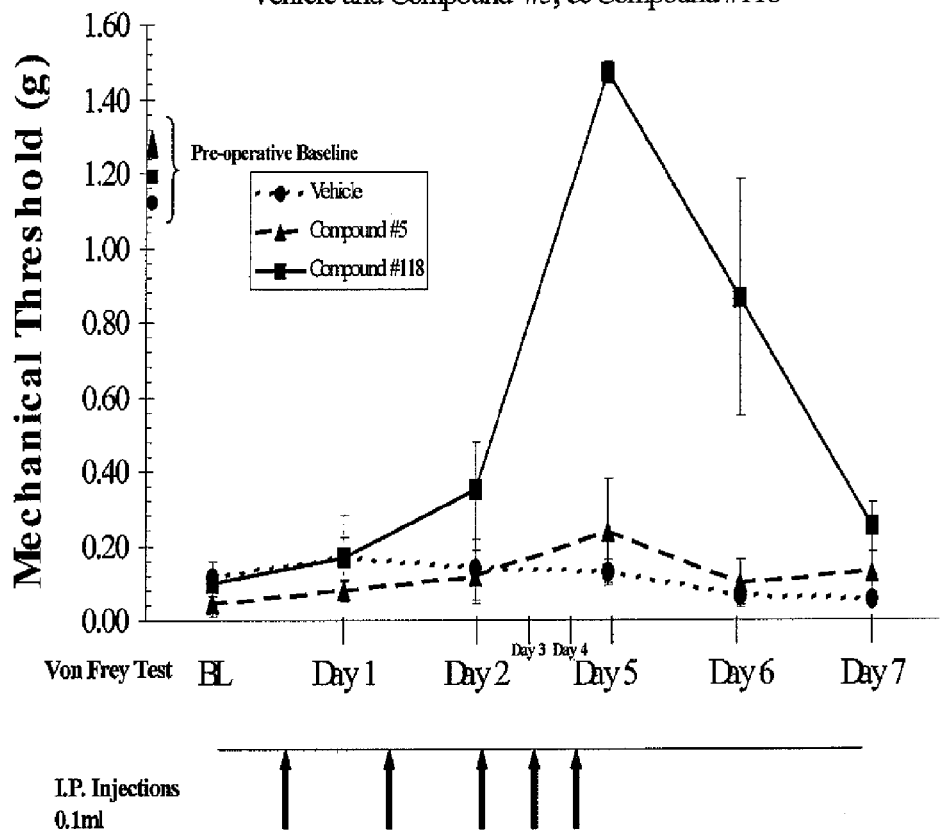
Figure 2. (I.P.)-SNL-Mouse Testing Results Comparing Vehicle and Compound #5, & Compound #118

COMPOUNDS AND METHODS FOR THE TREATMENT OF PAIN AND OTHER DISEASES

CROSS REFERENCE TO RELATED APPLICATIONS

This application is the U.S. national phase entry under 35 U.S.C. §371 of International Application No. PCT/US09/69005 filed Dec. 21, 2009 entitled COMPOUNDS AND METHODS FOR THE TREATMENT OF PAIN AND OTHER DISEASES, which in turn claims priority from U.S. Provisional Application Ser. No. 61/203,548, filed Dec. 23, 2008 and to U.S. Provisional Application Ser. No. 61/214,863, filed Apr. 29, 2009, all of which are incorporated herein by reference herein in their entirety for all purposes.

FIELD OF THE INVENTION

The present invention relates generally to metalloprotease inhibiting compounds, and more particularly to ethynl MMP inhibiting compounds.

BACKGROUND OF THE INVENTION

Inflammation is defined as the complex biological response of vascular tissues to harmful stimuli, such as pathogens, damaged cells, or irritants. It is a protective attempt by the organism to remove the injurious stimuli as well as initiate the healing process for the tissue. Inflammation may be acute (early phase of response) or chronic (occurs over a long time). Acute inflammation involves polymorphonuclear neutrophil leukocytes while chronic inflammation involves monocytes, macrophages, lymphocytes and plasma cells (collectively, mononuclear leukocytes). One affect of both acute and chronic inflammation is the sensation of pain which can be either neuropathic or nociceptive. Some common ailments associated with neuropathic pain are lower back pain, neuralgia/fibromyalgia, diabetic neuropathic pain and pain associated with multiple sclerosis. Common ailments associated with nociceptive pain are arthritic pain, particularly osteoarthritis and rheumatoid arthritis, post-operative pain, cancer-related pain and HIV-related pain.

Matrix metalloproteinases (MMPs) are a family of structurally related zinc-containing enzymes that have been reported to mediate the breakdown of connective tissue in normal physiological processes such as embryonic development, reproduction, and tissue remodelling. Over-expression of MMPs or an imbalance between MMPs has been suggested as factors in inflammatory, malignant and degenerative disease processes characterized by the breakdown of extracellular matrix or connective tissues. MMPs are, therefore, targets for therapeutic inhibitors in several inflammatory, malignant and degenerative diseases such as rheumatoid arthritis, osteoarthritis, osteoporosis, periodontitis, multiple sclerosis, gingivitis, corneal epidermal and gastric ulceration, atherosclerosis, neointimal proliferation (which leads to restenosis and ischemic heart failure) and tumor metastasis. MMP-2 (72 kDa gelatinase/GelatinaseA) degrades the extracelluar matrix components of the basement membrane. Their substrates include types IV and V collagen, fibronectin, elastin, and denatured interstitial collagens. Matrix degradation attributed to this proteinase has been shown to play an important role in the progression of such diseases as atherosclerosis, inflammation, stroke, and tumor growth and metastasis. However there has not been much literature demonstrating the use of MMP inhibitors and specifically inhibitors to MMP-2 to treat pain. For example, Yamamoto and coworkers (Neuroscience Letters, 347(2), (2003), 77-80) showed that injecting MMP-2 intrathecally in the rat formalin test (a model of inflammatory pain) depressed the Phase I agitation behavior but not the phase II behavior and that this analgesic affect was antagonized by the broad spectrum, hydroxamic acid containing, MMP inhibitor ONO-4817 ($K_i$ values are 0.45, 0.73, 1.1, 1.1, 2.1, 42 and 2500 nM for MMP-12, MMP-2, MMP-8, MMP-13, MMP-9, MMP-3 and MMP-7 respectively). When the MMP inhibitor ONO-4817 was given alone it had no affect on the rat formalin test.

Recently, Ji and coworkers (Nature Medicine 14 (13), (2008), 331-336) have found that certain matrix metalloproteinases (MMPs) were upregulated during the early stages of injury via a spinal nerve ligation animal model. Specifically, they found that MMP-9 was upregulated in injured dorsal root ganglion (DRG) primary sensory neurons in the early phase of the L5 spinal nerve ligation (SNL) neuropathic pain model (first day and then declining after $3^{rd}$ day) and that MMP-2 had a delayed response in the model (upregulation starting from day 7 and still present on day 21). They also found that MMP-2 induces neuropathic pain by IL-1β cleavage and astocytic extracellular signal-regulated kinase (ERK) activation. They also found that endogenous matrix metalloproteinase inhibitors (TIMP-1 and TIMP-2) also suppressed neuropathic pain in the model. Kobayashi and coworkers (Molecular and Cellular Neuroscience, 39, (2008), 619-627) also recently demonstrated that MMPs degrade peripheral myelin basic protein (MBP) and that a broad spectrum, hydroxamic acid containing MMP inhibitor (GM6001) was found to attenuate mechanical nociception.

Matrix metalloproteinase have been tested clinically in a few indications. Most predominantly in arthritis and cancer. Inhibitors that have entered clinical trials for an oncologic indication include prinomastat (AG3340; Agouron/Pfizer), BAY 12-9566 (Bayer Corp.), batimistat (BB-94; British Biotech, Ltd,), BMS-275291 (formerly D2163; Celltech/Bristol-Myers Squibb), marimastat (BB 2516; British Biotech, Ltd./Schering-Plough) and MMI270(B) (formerly CGS-27023A; Novartis). Many of the hydroxamic acid containing MMP inhibitors exhibit very broad toxicities in humans. For example, Marimastat, which contains a hydroxamate moiety, exhibited time-dependent and dose-dependent musculoskeletal toxicities (arthralgia, myalgia, tendinitis) in humans. Other toxicities for marimastat include ascites, disseminated carcinoma, chills, cholangitis, dizziness, dyspnea, edema, fatigue, fever, gastrointestinal (anorexia, nausea, vomiting, diarrhea, constipation), gastrointestinal hemorrhage, headache, heartburn, hepatic toxicity, hypercalcemia, hyperglycemia, rash, and shortness of breath. It is not known whether the toxicities exhibited by many of the MMP inhibitors are attributed to the hydroxamic acid moiety, however, it is clear that having an MMP inhibitor that does not contain a hydroxamic acid group could reduce many potential metabolic liabilities. One of the few non-hydroxamic acid containing compounds that have been tested in humans exclusively for the treatment of cancer is the tryptophan based acid S-3304 ((R)-3-(1H-Indol-3-yl)-2-(5-p-tolylethynyl-thiophene-2-sulfonylamino)-propionic acid) and which no evidence of musculoskeletal toxicities has been observed in animals or man. However, S-3304 has been found to give such adverse events in humans as headaches, somnolence, vomiting, nausea and gastrointestinal pain (van Marie, S. et al. Int. J. Clin. Pharmacol. Ther 2005; 43: 282-293). Further analysis of this compound in human blood found the formation of several hydroxylated metabolites (Chiapppori, A. A. et al. Clin. Cancer Res. 2007, 13(7), 2091-2099). Two of the main metabolites involved hydroxylation around the indole ring of the tryptophan moiety. Another metabolite involved hydroxylation of the toluene methyl portion of the molecule. It is clear that reducing the rate of such metabolically induced hydroxylations could reduce the metabolic liabilities of S3304 and/or enhance the overall bioavailability of the compound and possibly lead to an enhancement to the target tissue's exposure.

Kushner and coworkers (Kushner, D. J.; Baker, A.; Dunstall, T. G. Can J. Physiol Pharmacol, 77(2), (1999) p. 79-88) have presented examples of how incorporating deuterium into a drug can often reduce the level of metabolic induced transformations especially those mediated by Cytochrome P450. This reduce rate of Cytochrome P450 induce metabolism can sometimes translate directly to enhanced bioavailability. The reason for this is due to the fact that atomic substitution of a hydrogen by a deuterium in a drug alters the strength of the carbon-deuterium bond of the drug, while keeping it's 3D surface very similar to that of the nondeuterated version. Substitution of deuterium for hydrogen, can give rise to an isotope effect that can alter the pharmacokinetics of the drug. In a reaction in which the cleavage of a C—H bond is rate determining the same reaction of the C-D analogue will be reduced. For example Schneider and coworkers (Scheneider, F.; et al., BIRDS Pharma GmbH, Arzneimittel Forschung (2006), 56(4), p. 295-300) have shown that replacing several of the hydrogen atoms around one of the aromatic rings of the COX-2 inhibitor Refecoxib (4-(4-methylsulfonylphenyl)-3-phenyl-5H-furan-2-one) with deuterium (at positions 2',3',4',5' an 6') enhanced the oral bioavailability of the drug without affecting it's COX-2 selectivity. If one applied this strategy to the tryptophan based acid S-3304 one could reduce its susceptibility to cytochrome P-450 hydroxylation and ultimately enhance its overall bioavailability and possibly it's target tissue compound concentration.

Another possible affect of incorporating deuterium into a drug is on its polymorphic (i.e., different crystalline forms) properties. For example, Hirota and Urushibara (Bulletin of the Chemical Society of Japan, 32(7), (1959), 703-706) have shown that replacing a single vinylic hydrogen for deuterium on Allocinnamic acid can change both the melting point and the intensity of the x-ray diffraction pattern of the molecule. Lin and Guillory (Journal of Pharmaceutical Science, Vol. 59(7), (2006), 972-979) have shown that sulfanilamide-d4 exhibited smaller heats of transition and heats of fusion for its various crystalline states as compared to it's corresponding non-deuterated forms. Finally, Crawford and co-workers (Crawford, S. et al., Angewandte Chemie International Edition, 48(4), (2009), 755-757) recently showed that the crystalline form of fully deuterated pyridine adopts a unique configuration that can only be obtained under high pressure with the non-deuterated parent. Their work clearly showed that replacing hydrogen for deuterium changes the strength of interaction between various atoms in neighboring molecules causing a change in the crystalline arrangement to one that is more energetically favorable. This change in crystalline arrangement or polymorph may allow for improved dissolution properties and enhanced bioavailability.

A series of MMP inhibiting compounds containing a phenylethynyl-thiophene functional group and having no hydroxamic acid functionality is disclosed. Additionally, the invention relates to the present compounds and a method for treating pain in a patient.

SUMMARY OF THE INVENTION

The present invention relates to a new class of alkyne containing pharmaceutical agents. In particular, the present invention provides a new class of MMP inhibiting compounds containing a phenylethynyl-thiophene group that exhibit potent MMP inhibiting activity.

The present invention provides a new class of alkyne inhibiting compounds that are represented by the general Formula (I):

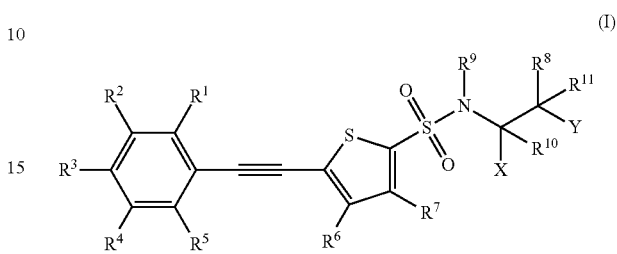

wherein all variables in the preceding Formulas (I) are as defined herein below.

$R^1$, $R^2$, $R^3$, $R^4$, $R^5$, $R^6$, $R^7$, $R^8$, $R^{10}$, and $R^{11}$ is independently selected from the group consisting of hydrogen, deuterium, halo, alkyl, cycloalkyl, heterocycloalkyl, bicycloalkyl, heterobicycloalkyl, spiroalkyl, spiroheteroalkyl, aryl, heteroaryl, cycloalkyl fused aryl, heterocycloalkyl fused aryl, cycloalkyl fused heteroaryl, heterocycloalkyl fused heteroaryl, cycloalkylalkyl, heterocycloalkylalkyl, bicycloalkylalkyl, heterobicycloalkylalkyl, spiroalkylalkyl, spiroheteroalkylalkyl, arylalkyl, heteroarylalkyl, cycloalkyl fused arylalkyl, heterocycloalkyl fused arylalkyl, cycloalkyl fused heteroarylalkyl, heterocycloalkyl fused heteroarylalkyl, hydroxy, alkoxy, alkenyl, alkynyl, $NO_2$, $NR^9R^9$, $NR^9NR^9R^9$, $NR^9N=CR^9R^9$, $NR^9SO_2R^9$, CN, $C(O)OR^9$, and fluoroalkyl; wherein alkyl, cycloalkyl, alkoxy, alkenyl, alkynyl and fluoroalkyl are optionally substituted one or more times and heterocycloalkyl fused heteroarylalkyl are optionally substituted one or more times;

X is independently selected from the group consisting of COOH, PO3H, COOD, and PO3D;

Y is independently selected from the group consisting of hydrogen, alkyl, cycloalkyl, heterocycloalkyl, bicycloalkyl, heterobicyclo, heterobicycloalkyl, spiroalkyl, spiroheteroalkyl, aryl, heteroaryl, cycloalkyl fused aryl, heterocycloalkyl fused aryl, cycloalkyl fused heteroaryl, heterocycloalkyl fused heteroaryl, cycloalkylalkyl, heterocycloalkylalkyl, bicycloalkylalkyl, heterobicycloalkylalkyl, spiroalkylalkyl, spiroheteroalkylalkyl, arylalkyl, heteroarylalkyl, cycloalkyl fused arylalkyl, heterocycloalkyl fused arylalkyl, cycloalkyl fused heteroarylalkyl, heterocycloalkyl fused heteroarylalkyl, fluoroalkyl, fluorobicyclo, and fluoroheterobicylco; and $R^9$ is independently selected from the group consisting of hydrogen, deuterium, alkyl, cycloalkyl, heteroaryl, arylalkyl, and fluoroalkyl; or N-oxides, pharmaceutically acceptable salts, prodrugs, formulations, polymorphs, tautomers, racemic mixtures or stereoisomers thereof.

Additionally, the present invention provides a new class of alkyne inhibiting compounds that are represented by the general Formula (II):

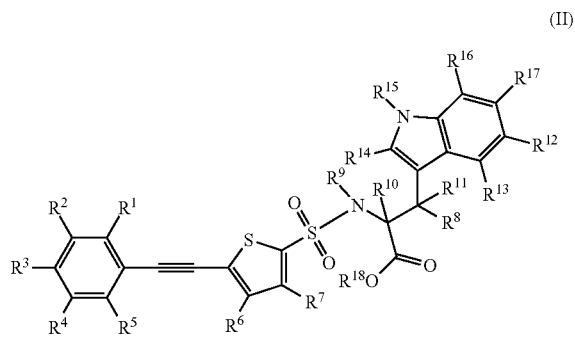

(II)

wherein:

each of $R^1$, $R^2$, $R^3$, $R^4$, $R^5$, $R^6$, $R^7$, $R^8$ $R^9$, $R^{10}$, $R^{11}$, $R^{12}$, $R^{13}$, $R^{14}$, $R^{15}$ $R^{16}$, and $R^{17}$ is independently selected from the group consisting of deuterium, hydrogen, alkyl, and deuteroalkyl; and $R^{18}$ is independently selected from the group consisting of hydrogen, deuterium, alkyl, deuteroalkyl, sodium, potassium; or N-oxides, pharmaceutically acceptable salts, prodrugs, formulations, polymorphs, tautomers, racemic mixtures or stereoisomers thereof.

The MMP inhibiting compounds of the present invention may also be used in the treatment of other metalloprotease mediated diseases, such as rheumatoid arthritis, osteoarthritis, abdominal aortic aneurysm, cancer, inflammation, atherosclerosis, multiple sclerosis, chronic obstructive pulmonary disease, ocular diseases, neurological diseases, psychiatric diseases, thrombosis, bacterial infection, Parkinson's disease, fatigue, tremor, diabetic retinopathy, vascular diseases of the retina, aging, dementia, cardiomyopathy, renal tubular impairment, diabetes, psychosis, dyskinesia, pigmentary abnormalities, deafness, inflammatory and fibrotic syndromes, intestinal bowel syndrome, allergies, Alzheimer's disease, arterial plaque formation, periodontal, viral infection, stroke, cardiovascular disease, reperfusion injury, trauma, chemical exposure or oxidative damage to tissues, wound healing, hemorrhoid, skin beautifying and pain.

In particular the MMP inhibiting compounds of the present invention may be used in the treatment of pain in a patient, said method comprising the step of administering to the patient a pain-treating effective amount of a present compound in combination with a carrier, wherein the patient is suffering from enhanced or exaggerated sensitivity to pain, such as hyperalgesia, causalgia and allodynia; acute pain; mechanical induced pain; burn pain; atypical facial pain; neuropathic pain; back pain; complex regional pain syndromes I and II; arthritic pain; sports injury pain; pain related to viral infection, post-herpetic neuralgia; phantom limb pain; labor pain; cancer pain; post-chemotherapy pain; post-stroke pain; post-operative pain; physiological pain; inflammatory pain; acute inflammatory conditions/visceral pain, e.g., angina, irritable bowel syndrome (IBS), and inflammatory bowel disease; neuropathic pain; neuralgia; painful diabetic neuropathy; traumatic nerve injury; spinal cord injury; and tolerance to narcotics or withdrawal from narcotics.

The present invention also provides MMP and/or other metalloprotease inhibiting compounds that are useful as active ingredients in pharmaceutical compositions for treatment or prevention of metalloprotease—especially MMP-mediated diseases. The present invention also contemplates use of such compounds in pharmaceutical compositions for oral or, parenteral administration, comprising one or more of the MMP inhibiting compounds disclosed herein.

The present invention further provides methods of inhibiting MMP-2 and/or other metalloproteases, by administering formulations, including, but not limited to, oral, rectal, topical, intravenous, parenteral (including, but not limited to, intramuscular, intravenous), ocular (ophthalmic), transdermal, inhalative (including, but not limited to, pulmonary, aerosol inhalation), nasal, sublingual, intrathecal, subcutaneous or intraarticular formulations, comprising the heterobicyclic metalloprotease inhibiting compounds by standard methods known in medical practice, for the treatment of diseases or symptoms arising from or associated with metalloprotease, especially MMP-2 and including prophylactic and therapeutic treatment. Although the most suitable route in any given case will depend on the nature and severity of the conditions being treated and on the nature of the active ingredient. The compounds from this invention are conveniently presented in unit dosage form and prepared by any of the methods well known in the art of pharmacy.

The MMP inhibiting compounds of the present invention may be used in combination with a disease modifying anti-rheumatic drug, a nonsteroidal anti-inflammatory drug, a COX-2 selective inhibitor, a COX-1 inhibitor, an immunosuppressive, a steroid, a biological response modifier or other anti-inflammatory agents.

BRIEF DESCRIPTION OF THE DRAWINGS

FIG. 1 is a graph of an Intrathecal (i.t.) (SNL) mouse experiment. The von Frey monofilament test for mechanical allodynia. Arrows represent injection times. Results are described in paw withdrawal thresholds (g). BL=Post-operative Baseline.

FIG. 2 is a graph of an Intraperitonel (i.p.) (SNL)-mouse experiment. The von Frey monofilament test for mechanical allodynia. Arrows represent injection times. Results are described in paw withdrawal thresholds (g). BL=Post-operative Baseline.

DETAILED DESCRIPTION OF THE INVENTION

The term "D" as used herein alone or as part of a chemical structure or group, denotes deuterium.

The term "deutero" as used herein alone or as part of a group, denote optionally substituted deuterium atoms.

The terms "alkyl" or "alk", as used herein alone or as part of another group, denote optionally substituted, straight and branched chain saturated hydrocarbon groups, preferably having 1 to 10 carbons in the normal chain, most preferably lower alkyl groups. Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl and the like. Exemplary substituents may include, but are not limited to, one or more of the following groups: halo, alkoxy, alkylthio, alkenyl, alkynyl, aryl (e.g., to form a benzyl group), cycloalkyl, cycloalkenyl, hydroxy or protected hydroxy, carboxyl (—COOH), alkyloxycarbonyl, alkylcarbonyloxy, alkylcarbonyl, carbamoyl ($NH_2$—CO—), substituted carbamoyl (($R^{10}$)($R^{11}$)N—CO— wherein $R^{10}$ or $R^{11}$ are as defined below, except that at least one of $R^{10}$ or $R^{11}$ is not hydrogen), amino, heterocyclo, mono- or dialkylamino, or thiol (—SH).

The term "heteroalkyl" and which may be used interchangeably with the term "alkyl" denote optionally substituted, straight and branched chain saturated hydrocarbon groups, preferably having 1 to 10 carbons in the normal chain, most preferably lower alkyl groups. Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl and the like. Exemplary substituents may include, but are not limited to, one or more of the following groups: halo, alkoxy, alkylthio, alkenyl, alkynyl, aryl (e.g., to form a benzyl group), cycloalkyl, cycloalkenyl, hydroxy or protected hydroxy, carboxyl (—COOH), alkyloxycarbonyl, alkylcarbonyloxy, alkylcarbonyl, carbamoyl ($NH_2$—CO—)

The terms "lower alk" or "lower alkyl" as used herein, denote such optionally substituted groups as described above for alkyl having 1 to 4 carbon atoms in the normal chain.

The term "alkoxy" denotes an alkyl group as described above bonded through an oxygen linkage (—O—).

The term "alkenyl", as used herein alone or as part of another group, denotes optionally substituted, straight and branched chain hydrocarbon groups containing at least one carbon to carbon double bond in the chain, and preferably having 2 to 10 carbons in the normal chain. Exemplary unsubstituted such groups include ethenyl, propenyl, isobutenyl, butenyl, pentenyl, hexenyl, heptenyl, octenyl, nonenyl, decenyl, and the like. Exemplary substituents may include, but are not limited to, one or more of the following groups: halo, alkoxy, alkylthio, alkyl, alkynyl, aryl, cycloalkyl, cycloalkenyl, hydroxy or protected hydroxy, carboxyl (—COOH), alkyloxycarbonyl, alkylcarbonyloxy, alkylcarbonyl, carbamoyl ($NH_2$—CO—), substituted carbamoyl.

The term "alkynyl", as used herein alone or as part of another group, denotes optionally substituted, straight and branched chain hydrocarbon groups containing at least one carbon to carbon triple bond in the chain, and preferably having 2 to 10 carbons in the normal chain. Exemplary unsubstituted such groups include, but are not limited to, ethynyl, propynyl, butynyl, pentynyl, hexynyl, heptynyl, octynyl, nonynyl, decynyl, and the like. Exemplary substituents may include, but are not limited to, one or more of the following groups: halo, alkoxy, alkylthio, alkyl, alkenyl, aryl, cycloalkyl, cycloalkenyl, hydroxy or protected hydroxy, carboxyl (—COOH), alkyloxycarbonyl, alkylcarbonyloxy, alkylcarbonyl, carbamoyl ($NH_2$—CO—), substituted carbamoyl.

The term "cycloalkyl", as used herein alone or as part of another group, denotes optionally substituted, saturated cyclic hydrocarbon ring systems, including bridged ring systems, desirably containing 1 to 3 rings and 3 to 9 carbons per ring. Exemplary unsubstituted such groups include, but are not limited to, cyclopropyl, cyclobutyl, cyclopentyl, cyclohexyl, cycloheptyl, cyclooctyl, cyclodecyl, cyclododecyl, and adamantyl. Exemplary substituents include, but are not limited to, one or more alkyl groups as described above, or one or more groups described above as alkyl substituents.

The terms "ar" or "aryl", as used herein alone or as part of another group, denote optionally substituted, homocyclic aromatic groups, preferably containing 1 or 2 rings and 6 to 12 ring carbons. Exemplary unsubstituted such groups include, but are not limited to, phenyl, biphenyl, and naphthyl. Exemplary substituents include, but are not limited to, one or more nitro groups, alkyl groups as described above or groups described above as alkyl substituents.

The term "heterocycle" or "heterocyclic system" denotes a heterocyclyl, heterocyclenyl, or heteroaryl group as described herein, which contains carbon atoms and from 1 to 4 heteroatoms independently selected from N, O and S and including any bicyclic or tricyclic group in which any of the above-defined heterocyclic rings is fused to one or more heterocycle, aryl or cycloalkyl groups. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom.

Examples of heterocycles include, but are not limited to 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolinyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl.

"Heterocyclenyl" denotes a non-aromatic monocyclic or multicyclic hydrocarbon ring system of about 3 to about 10 atoms, desirably about 4 to about 8 atoms, in which one or more of the carbon atoms in the ring system is/are hetero element(s) other than carbon, for example nitrogen, oxygen or sulfur atoms, and which contains at least one carbon-carbon double bond or carbon-nitrogen double bond. Ring sizes of rings of the ring system may include 5 to 6 ring atoms. The designation of the aza, oxa or thia as a prefix before heterocyclenyl define that at least a nitrogen, oxygen or sulfur atom is present respectively as a ring atom. The heterocyclenyl may be optionally substituted by one or more substituents as defined herein. The nitrogen or sulphur atom of the heterocyclenyl may also be optionally oxidized to the corresponding N-oxide, S-oxide or S,S-dioxide. "Heterocyclenyl" as used herein includes by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960), the contents all of which are incorporated by reference herein. Exemplary monocyclic azaheterocyclenyl groups include, but are not limited to, 1,2,3,4-tetrahydrohydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Exemplary oxaheterocyclenyl groups include, but are not limited to, 3,4-dihydro-2H-pyran, dihydrofuranyl, and fluorodihydrofuranyl. An exemplary multicyclic oxaheterocyclenyl group is 7-oxabicyclo[2.2.1]heptenyl.

"Heterocyclyl," or "heterocycloalkyl," denotes a non-aromatic saturated monocyclic or multicyclic ring system of about 3 to about 10 carbon atoms, desirably 4 to 8 carbon atoms, in which one or more of the carbon atoms in the ring system is/are hetero element(s) other than carbon, for example nitrogen, oxygen or sulfur. Ring sizes of rings of the ring system may include 5 to 6 ring atoms. The designation of the aza, oxa or thia as a prefix before heterocyclyl define that at least a nitrogen, oxygen or sulfur atom is present respectively as a ring atom. The heterocyclyl may be optionally substituted by one or more substituents which may be the same or different, and are as defined herein. The nitrogen or sulphur atom of the heterocyclyl may also be optionally oxidized to the corresponding N-oxide, S-oxide or S,S-dioxide.

"Heterocyclyl" as used herein includes by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960). Exemplary monocyclic heterocyclyl rings include, but are not limited to, piperidyl, pyrrolidinyl, piperazinyl, morpholinyl, thiomorpholinyl, thiazolidinyl, 1,3-dioxolanyl, tetrahydrofuranyl, tetrahydrothiophenyl, tetrahydrothiopyranyl, and the like.

"Heteroaryl" denotes an aromatic monocyclic or multicyclic ring system of about 5 to about 10 atoms, in which one or more of the atoms in the ring system is/are hetero element(s) other than carbon, for example nitrogen, oxygen or sulfur. Ring sizes of rings of the ring system include 5 to 6 ring atoms. The "heteroaryl" may also be substituted by one or more substituents which may be the same or different, and are as defined herein. The designation of the aza, oxa or thia as a prefix before heteroaryl define that at least a nitrogen, oxygen or sulfur atom is present respectively as a ring atom. A nitrogen atom of a heteroaryl may be optionally oxidized to the corresponding N-oxide. Heteroaryl as used herein includes by way of example and not limitation those described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960). Exemplary heteroaryl and substituted heteroaryl groups include, but are not limited to, pyrazinyl, thienyl, isothiazolyl, oxazolyl, pyrazolyl, furazanyl, pyrrolyl, 1,2,4-thiadiazolyl, pyridazinyl, quinoxalinyl, phthalazinyl, imidazo[1,2-a]pyridine, imidazo[2,1-b]thiazolyl, benzofurazanyl, azaindolyl, benzimidazolyl, benzothienyl, thienopyridyl, thienopyrimidyl, pyrrolopyridyl, imidazopyridyl, benzoazaindole, 1,2,3-triazinyl, 1,2,4-triazinyl, 1,3,5-triazinyl, benzthiazolyl, dioxolyl, furanyl, imidazolyl, indolyl, indolizinyl, isoxazolyl, isoquinolinyl, isothiazolyl, oxadiazolyl, oxazinyl, oxiranyl, piperazinyl, piperidinyl, pyranyl, pyrazinyl, pyridazinyl, pyrazolyl, pyridyl, pyrimidinyl, pyrrolyl, pyrrolidinyl, quinazolinyl, quinolinyl, tetrazinyl, tetrazolyl, 1,3,4-thiadiazolyl, 1,2,3-thiadiazolyl, 1,2,4-thiadiazolyl, 1,2,5-thiadiazolyl, thiatriazolyl, thiazinyl, thiazolyl, thienyl, 5-thioxo-1,2,4-diazolyl, thiomorpholino, thiophenyl, thiopyranyl, triazolyl and triazolonyl.

The term "amino" denotes the radical —$NH_2$ wherein one or both of the hydrogen atoms may be replaced by an optionally substituted hydrocarbon group. Exemplary amino groups include, but are not limited to, n-butylamino, tert-butylamino, methylpropylamino and ethyldimethylamino.

The term "cycloalkylalkyl" denotes a cycloalkyl-alkyl group wherein a cycloalkyl as described above is bonded through an alkyl, as defined above. Cycloalkylalkyl groups may contain a lower alkyl moiety. Exemplary cycloalkylalkyl groups include, but are not limited to, cyclopropylmethyl, cyclopentylmethyl, cyclohexylmethyl, cyclopropylethyl, cyclopentylethyl, cyclohexylpropyl, cyclopropylpropyl, cyclopentylpropyl, and cyclohexylpropyl.

The term "arylalkyl" denotes an aryl group as described above bonded through an alkyl, as defined above.

The term "heteroarylalkyl" denotes a heteroaryl group as described above bonded through an alkyl, as defined above.

The term "heterocyclylalkyl," or "heterocycloalkylalkyl," denotes a heterocyclyl group as described above bonded through an alkyl, as defined above.

The terms "halogen", "halo", or "hal", as used herein alone or as part of another group, denote chlorine, bromine, fluorine, and iodine.

The term "haloalkyl" denotes a halo group as described above bonded though an alkyl, as defined above. Fluoroalkyl is an exemplary group.

The term "aminoalkyl" denotes an amino group as defined above bonded through an alkyl, as defined above.

The phrase "bicyclic fused ring system wherein at least one ring is partially saturated" denotes an 8- to 13-membered fused bicyclic ring group in which at least one of the rings is non-aromatic. The ring group has carbon atoms and optionally 1-4 heteroatoms independently selected from N, O and S. Illustrative examples include, but are not limited to, indanyl, tetrahydronaphthyl, tetrahydroquinolyl and benzocycloheptyl.

The phrase "tricyclic fused ring system wherein at least one ring is partially saturated" denotes a 9- to 18-membered fused tricyclic ring group in which at least one of the rings is non-aromatic. The ring group has carbon atoms and optionally 1-7 heteroatoms independently selected from N, O and S. Illustrative examples include, but are not limited to, fluorene, 10,11-dihydro-5H-dibenzo[a,d]cycloheptene and 2,2a,7,7a-tetrahydro-1H-cyclobuta[a] indene The term "isotopic enrichment" refers to a process by which the relative abundance of an isotope of a given element are altered, thus producing a form of the element that has been enriched in one particular isotope and depleted in its other isotopic forms.

The term "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as, but not limited to, hydrochloric, hydrobromic, sulfuric, sulfamic, phosphoric, nitric and the like; and the salts prepared from organic acids such as, but not limited to, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. The pharmaceutically acceptable salts include deuterated organic acid salts of basic residues such as amines; alkali or organic salts of acidic residues such as carboxylic acids; and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Organic solvents include, but are not limited to, nonaqueous media like ethers, ethyl acetate, ethanol, isopropanol, or acetonitrile. Lists of suitable salts are found in *Remington's Pharmaceutical Sciences,* 18th ed., Mack Publishing Company, Easton, Pa., 1990, p. 1445, the disclosure of which is hereby incorporated by reference.

The phrase "pharmaceutically acceptable" denotes those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The term "N-oxide" denotes compounds that can be obtained in a known manner by reacting a compound of the present invention including a nitrogen atom (such as in a pyridyl group) with hydrogen peroxide or a peracid, such as 3-chloroperoxy-benzoic acid, in an inert solvent, such as dichloromethane, at a temperature between about −10-80° C., desirably about 0° C.

The term "polymorph" denotes a form of a chemical compound in a particular crystalline arrangement. Certain polymorphs may exhibit enhanced thermodynamic stability and may be more suitable than other polymorphic forms for inclusion in pharmaceutical formulations. Compounds having hydrogens replaced by deuterium may form polymorphs which may enhance their solubility and/or bioavailability properties.

The compounds of the invention can contain one or more chiral centers and/or double bonds and, therefore, exist as stereoisomers, such as double-bond isomers (i.e., geometric isomers), enantiomers, or diastereomers. According to the invention, the chemical structures depicted herein, and therefore the compounds of the invention, encompass all of the corresponding enantiomers and stereoisomers, that is, both the stereomerically pure form (e.g., geometrically pure, enantiomerically pure, or diastereomerically pure) and enantiomeric and stereoisomeric mixtures.

The term "racemic mixture" denotes a mixture that is about 50% of one enantiomer and about 50% of the corresponding enantiomer relative to all chiral centers in the molecule. Thus, the invention encompasses all enantiomerically-pure, enantiomerically-enriched, and racemic mixtures of compounds of Formulas (I) and (II).

Enantiomeric and stereoisomeric mixtures of compounds of the invention can be resolved into their component enantiomers or stereoisomers by well-known methods. Examples include, but are not limited to, the formation of chiral salts and the use of chiral or high performance liquid chromatography "HPLC" and the formation and crystallization of chiral salts. See, e.g., Jacques, J., et al., Enantiomers, Racemates and Resolutions (Wiley-Interscience, New York, 1981); Wilen, S. H., et al., Tetrahedron 33:2725 (1977); Eliel, E. L., Stereochemistry of Carbon Compounds (McGraw-Hill, NY, 1962); Wilen, S. H., Tables of Resolving Agents and Optical Resolutions p. 268 (E. L. Eliel, Ed., Univ. of Notre Dame Press, Notre Dame, Ind., 1972); Stereochemistry of Organic Compounds, Ernest L. Eliel, Samuel H. Wilen and Lewis N. Manda (1994 John Wiley & Sons, Inc.), and Stereoselective Synthesis A Practical Approach, Mihaly Nogradi (1995 VCH Publishers, Inc., NY, N.Y.). Enantiomers and stereoisomers can also be obtained from stereomerically- or enantiomerically-pure intermediates, reagents, and catalysts by well-known asymmetric synthetic methods.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

Unless moieties of a compound of the present invention are defined as being unsubstituted, the moieties of the compound may be substituted. In addition to any substituents provided above, the moieties of the compounds of the present invention may be optionally substituted with one or more groups independently selected from:

$C_1$-$C_4$ alkyl;
$C_2$-$C_4$ alkenyl;
$C_2$-$C_4$ alkynyl;
$CF_3$;
halo;
OH;
O—($C_1$-$C_4$ alkyl);
$OCH_2F$;
$OCHF_2$;
$OCF_3$;
OC(O)—($C_1$-$C_4$ alkyl);
OC(O)—($C_1$-$C_4$ alkyl);
OC(O)NH—($C_1$-$C_4$ alkyl);
OC(O)N($C_1$-$C_4$ alkyl)$_2$;
OC(S)NH—($C_1$-$C_4$ alkyl);
OC(S)N($C_1$-$C_4$ alkyl)$_2$;
SH;
S—($C_1$-$C_4$ alkyl);
S(O)—($C_1$-$C_4$ alkyl);
S(O)$_2$—($C_1$-$C_4$ alkyl);
SC(O)—($C_1$-$C_4$ alkyl);
SC(O)O—($C_1$-$C_4$ alkyl);
$NH_2$;
N(H)—($C_1$-$C_4$ alkyl);
N($C_1$-$C_4$ alkyl)$_2$;
N(H)C(O)—($C_1$-$C_4$ alkyl);
N($CH_3$)C(O)—($C_1$-$C_4$ alkyl);
N(H)C(O)—$CF_3$;
N($CH_3$)C(O)—$CF_3$;
N(H)C(S)—($C_1$-$C_4$ alkyl);
N($CH_3$)C(S)—($C_1$-$C_4$ alkyl);
N(H)S(O)$_2$—($C_1$-$C_4$ alkyl);
N(H)C(O)$NH_2$;
N(H)C(O)NH—($C_1$-$C_4$ alkyl);
N($CH_3$)C(O)NH—($C_1$-$C_4$ alkyl);
N(H)C(O)N($C_1$-$C_4$ alkyl)$_2$;
N($CH_3$)C(O)N($C_1$-$C_4$ alkyl)$_2$;
N(H)S(O)$_2$$NH_2$;
N(H)S(O)$_2$NH—($C_1$-$C_4$ alkyl);
N($CH_3$)S(O)$_2$NH—($C_1$-$C_4$ alkyl);
N(H)S(O)$_2$N($C_1$-$C_4$ alkyl)$_2$;
N($CH_3$)S(O)$_2$N($C_1$-$C_4$ alkyl)$_2$;
N(H)C(O)O—($C_1$-$C_4$ alkyl);
N($CH_3$)C(O)O—($C_1$-$C_4$ alkyl);
N(H)S(O)$_2$O—($C_1$-$C_4$ alkyl);

N(CH$_3$)S(O)$_2$O—(C$_1$-C$_4$ alkyl);
N(CH$_3$)C(S)NH—(C$_1$-C$_4$ alkyl);
N(CH$_3$)C(S)N(C$_1$-C$_4$ alkyl)$_2$;
N(CH$_3$)C(S)O—(C$_1$-C$_4$ alkyl);
N(H)C(S)NH$_2$;
NO$_2$;
CO$_2$H;
CO$_2$—(C$_1$-C$_4$ alkyl);
C(O)N(H)OH;
C(O)N(CH$_3$)OH:
C(O)N(CH$_3$)OH;
C(O)N(CH$_3$)O—(C$_1$-C$_4$ alkyl);
C(O)N(H)—(C$_1$-C$_4$ alkyl);
C(O)N(C$_1$-C$_4$ alkyl)$_2$;
C(S)N(H)—(C$_1$-C$_4$ alkyl);
C(S)N(C$_1$-C$_4$ alkyl)$_2$;
C(NH)N(H)—(C$_1$-C$_4$ alkyl);
C(NH)N(C$_1$-C$_4$ alkyl)$_2$;
C(NCH$_3$)N(H)—(C$_1$-C$_4$ alkyl);
C(NCH$_3$)N(C$_1$-C$_4$ alkyl)$_2$;
C(O)—(C$_1$-C$_4$ alkyl);
C(NH)—(C$_1$-C$_4$ alkyl);
C(NCH$_3$)—(C$_1$-C$_4$ alkyl);
C(NOH)—(C$_1$-C$_4$ alkyl);
C(NOCH$_3$)—(C$_1$-C$_4$ alkyl);
CN;
CHO;
CH$_2$OH;
CH$_2$O—(C$_1$-C$_4$ alkyl);
CH$_2$NH$_2$;
CH$_2$N(H)—(C$_1$-C$_4$ alkyl);
CH$_2$N(C$_1$-C$_4$ alkyl)$_2$;
aryl;
heteroaryl;
cycloalkyl; and
heterocyclyl.

In one embodiment of the present invention, the alkyne containing metalloprotease inhibiting compounds may be represented by the general Formula (I):

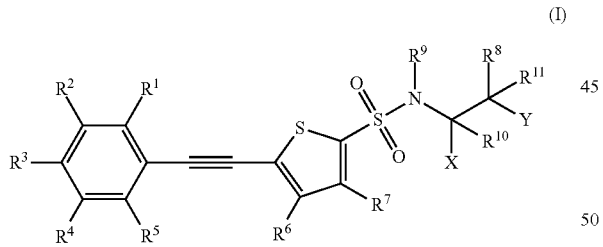

wherein all variables in the preceding Formulas (I) are as defined herein below.

R$^1$, R$^2$, R$^3$, R$^4$, R$^5$, R$^6$, R$^7$, R$^8$, R$^{10}$, and R$^{11}$ is independently selected from the group consisting of hydrogen, deuterium, halo, alkyl, cycloalkyl, heterocycloalkyl, bicycloalkyl, heterobicycloalkyl, spiroalkyl, spiroheteroalkyl, aryl, heteroaryl, cycloalkyl fused aryl, heterocycloalkyl fused aryl, cycloalkyl fused heteroaryl, heterocycloalkyl fused heteroaryl, cycloalkylalkyl, heterocycloalkylalkyl, bicycloalkylalkyl, heterobicycloalkylalkyl, spiroalkylalkyl, spiroheteroalkylalkyl, arylalkyl, heteroarylalkyl, cycloalkyl fused arylalkyl, heterocycloalkyl fused arylalkyl, cycloalkyl fused heteroarylalkyl, heterocycloalkyl fused heteroarylalkyl, hydroxy, alkoxy, alkenyl, alkynyl, NO$_2$, NR$^9$R$^9$, NR$^9$NR$^9$R$^9$, NR$^9$N=CR$^9$R$^9$, NR$^9$SO$_2$R$^9$, CN, C(O)OR$^9$, and fluoroalkyl;

wherein alkyl, cycloalkyl, alkoxy, alkenyl, alkynyl and fluoroalkyl are optionally substituted one or more times and heterocycloalkyl fused heteroarylalkyl are optionally substituted one or more times;

X is independently selected from the group consisting of COOH, PO3H, COOD, and PO3D;

Y is independently selected from the group consisting of hydrogen, alkyl, cycloalkyl, heterocycloalkyl, bicycloalkyl, heterobicyclo, heterobicycloalkyl, spiroalkyl, spiroheteroalkyl, aryl, heteroaryl, cycloalkyl fused aryl, heterocycloalkyl fused aryl, cycloalkyl fused heteroaryl, heterocycloalkyl fused heteroaryl, cycloalkylalkyl, heterocycloalkylalkyl, bicycloalkylalkyl, heterobicycloalkyl alkyl, spiroalkylalkyl, spiroheteroalkylalkyl, arylalkyl, heteroarylalkyl, cycloalkyl fused arylalkyl, heterocycloalkyl fused arylalkyl, cycloalkyl fused heteroarylalkyl, heterocycloalkyl fused heteroarylalkyl, fluoroalkyl, fluorobicyclo, and fluoroheterobicylco; and R$^9$ is independently selected from the group consisting of hydrogen, deuterium, alkyl, cycloalkyl, heteroaryl, arylalkyl, and fluoroalkyl; or N-oxides, pharmaceutically acceptable salts, prodrugs, formulations, polymorphs, tautomers, racemic mixtures or stereoisomers thereof.

In some embodiments of the present invention, Y may include a heteroaryl ring system. In accordance with such embodiments, Y may be:

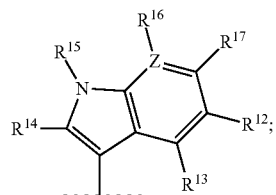

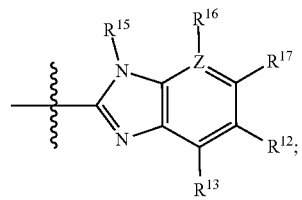

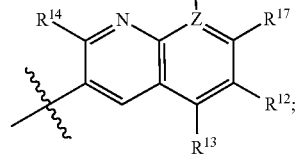

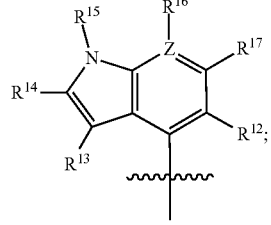

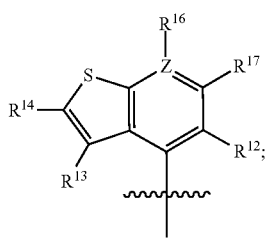

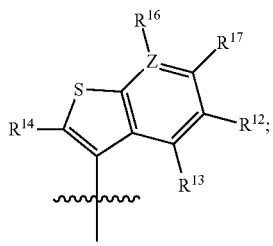

wherein:

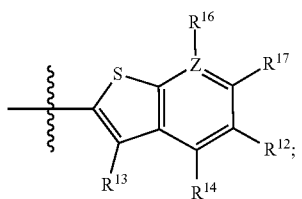

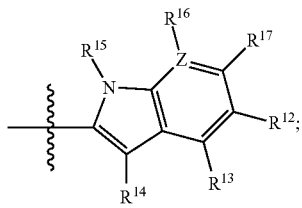

wherein:

each of $R^{12}$, $R^{13}$, $R^{14}$, $R^{15}$, and $R^{17}$ is independently selected from the group consisting of hydrogen, deuterium, halo, alkyl, cycloalkyl, heterocycloalkyl, bicycloalkyl, heterobicycloalkyl, spiroalkyl, spiroheteroalkyl, aryl, heteroaryl, cycloalkyl fused aryl, heterocycloalkyl fused aryl, cycloalkyl fused heteroaryl, heterocycloalkyl fused heteroaryl, cycloalkylalkyl, heterocycloalkylalkyl, bicycloalkylalkyl, heterobicycloalkylalkyl, spiroalkylalkyl, spiroheteroalkylalkyl, arylalkyl, heteroarylalkyl, cycloalkyl fused arylalkyl, heterocycloalkyl fused arylalkyl, cycloalkyl fused heteroarylalkyl, heterocycloalkyl fused heteroarylalkyl, hydroxy, alkoxy, alkenyl, alkynyl, $NO_2$, $NR^9R^9$, $NR^9NR^9R^9$, $NR^9N=CR^9R^9$, $NR^9SO_2R^9$, CN, C(O)OR$^9$, and fluoroalkyl; wherein alkyl, cycloalkyl, alkoxy, alkenyl, alkynyl and fluoroalkyl are optionally substituted one or more times and heterocycloalkyl fused heteroarylalkyl are optionally substituted one or more times;

$R^9$ is independently selected from the group consisting of hydrogen, deuterium, alkyl, cycloalkyl, heteroaryl, arylalkyl, and fluoroalkyl;

$R^{15}$ is independently selected from the group consisting of hydrogen, deuterium, methyl, alkyl, trifluoromethyl, trideuteromethyl, and fluoroalkyl; and Z is independently C or N;

(1) wherein when Z is C, $R^{16}$ is independently selected from the group consisting of hydrogen, deuterium, halo, alkyl, cycloalkyl, heterocycloalkyl, bicycloalkyl, heterobicycloalkyl, spiroalkyl, spiroheteroalkyl, aryl, heteroaryl, cycloalkyl fused aryl, heterocycloalkyl fused aryl, cycloalkyl fused heteroaryl, heterocycloalkyl fused heteroaryl, cycloalkylalkyl, heterocycloalkylalkyl, bicycloalkylalkyl, heterobicycloalkylalkyl, spiroalkylalkyl, spiroheteroalkylalkyl, arylalkyl, heteroarylalkyl, cycloalkyl fused arylalkyl, heterocycloalkyl fused arylalkyl, cycloalkyl fused heteroarylalkyl, heterocycloalkyl fused heteroarylalkyl, alkenyl, alkynyl, $NO_2$, $NR^9R^9$, $NR^9NR^9R^9$, $NR^9N=CR^9R^9$, $NR^9SO_2R^9$, CN, C(O)OR$^9$, and fluoroalkyl, wherein alkyl, cycloalkyl, alkoxy, alkenyl, alkynyl and fluoroalkyl are optionally substituted one or more times and heterocycloalkyl fused heteroarylalkyl are optionally substituted one or more times; or (2) wherein when Z is N, $R^{16}$ is no atom or bond.

N-oxides, pharmaceutically acceptable salts, prodrugs, formulations, polymorphs, tautomers, racemic mixtures or stereoisomers thereof.

In another embodiment of the present invention, the alkyne containing metalloprotease inhibiting compounds may be represented by the general Formula (II):

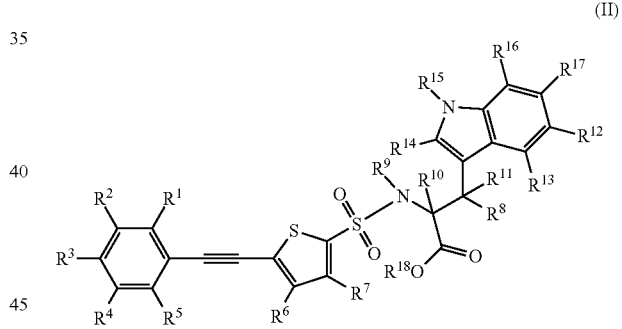

(II)

wherein:

each of $R^1$, $R^2$, $R^3$, $R^4$, $R^5$, $R^6$, $R^7$, $R^8$ $R^9$, $R^{10}$, $R^{11}$, $R^{12}$, $R^{13}$, $R^{14}$, $R^{15}$ $R^{16}$, and $R^{17}$ is independently selected from the group consisting of deuterium, hydrogen, alkyl, and deuteroalkyl;

$R^{18}$ is independently selected from the group consisting of hydrogen, deuterium, alkyl, deuteroalkyl, sodium, and potassium; or N-oxides, pharmaceutically acceptable salts, prodrugs, formulations, polymorphs, tautomers, racemic mixtures or stereoisomers thereof.

It is contemplated that the compounds of the present invention represented by the Formulas described above include all diastereomers and enantiomers, as well as racemic mixtures. Racemic mixtures may be separated by chiral salt resolution or by chiral column HPLC chromatography.

More specifically, the compounds of Formulas (I) & (II) may be selected from, but are not limited to, the following:

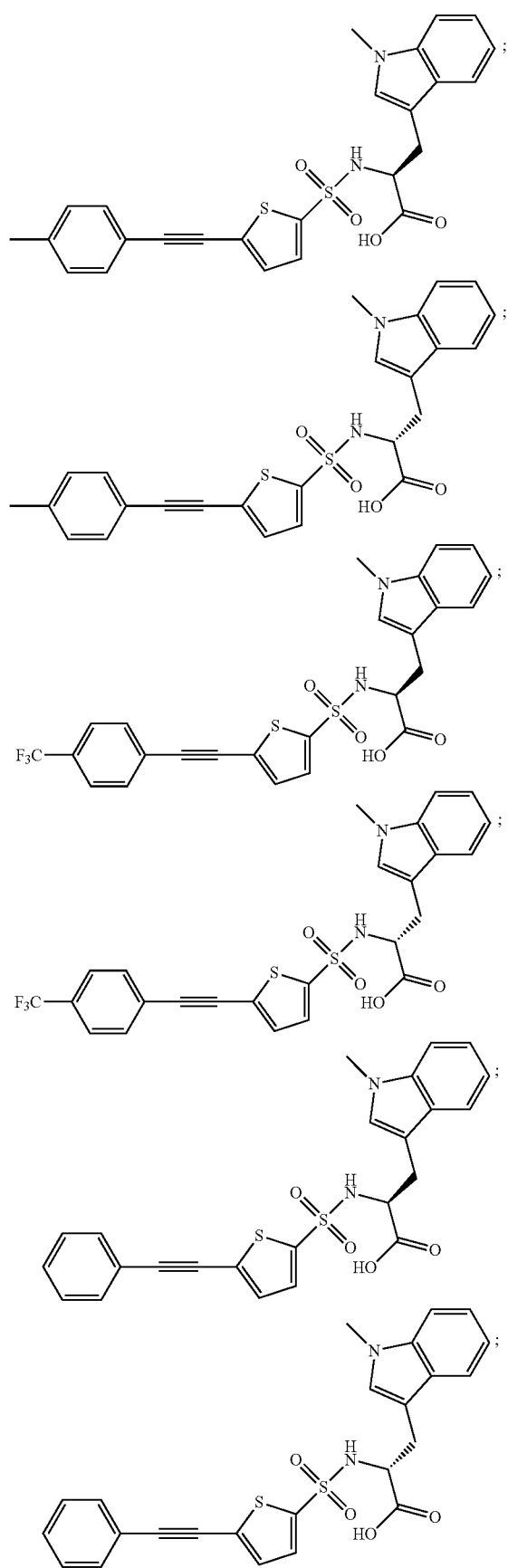
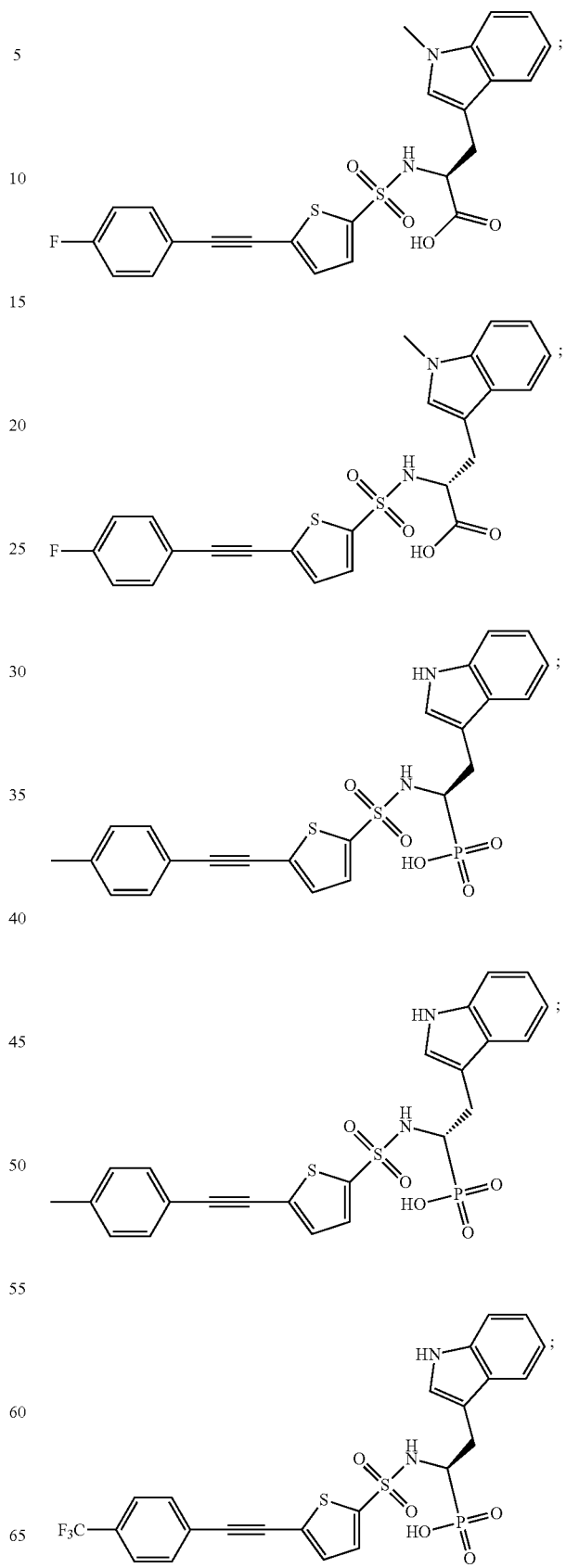

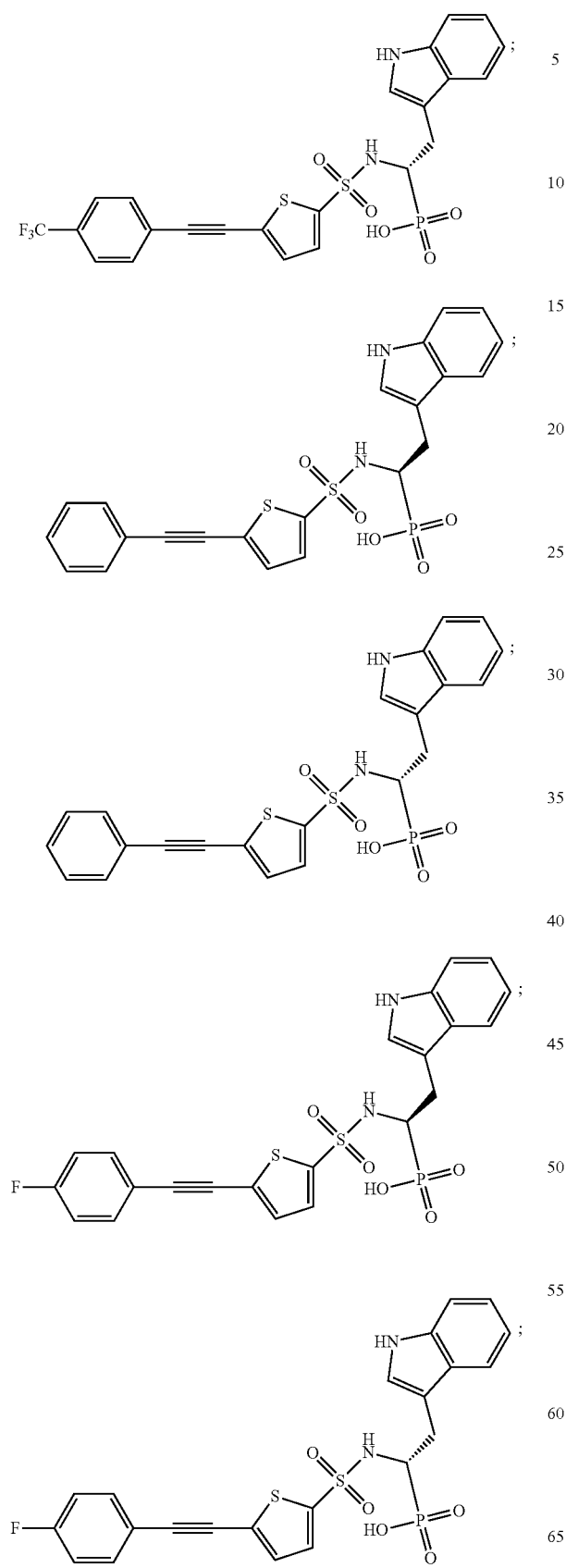
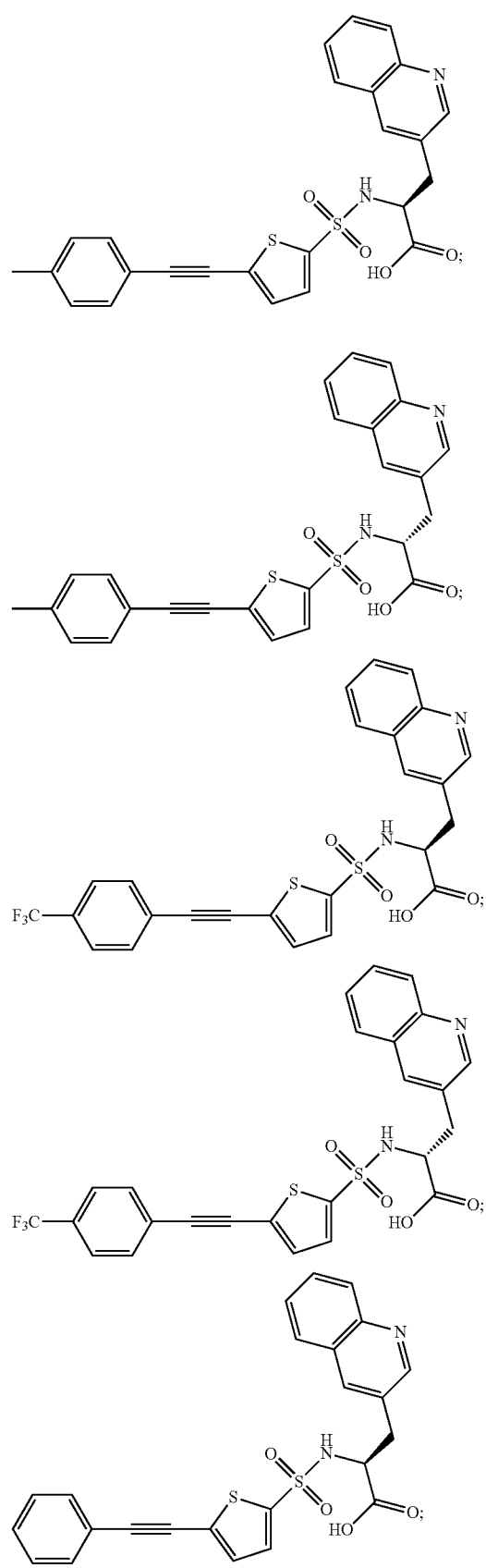

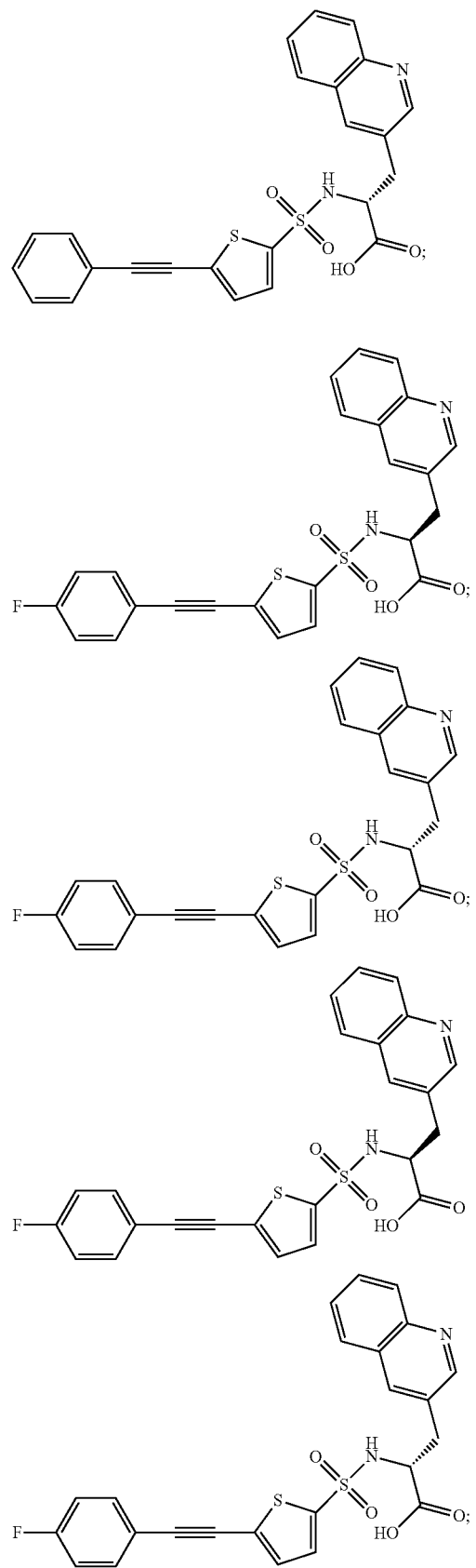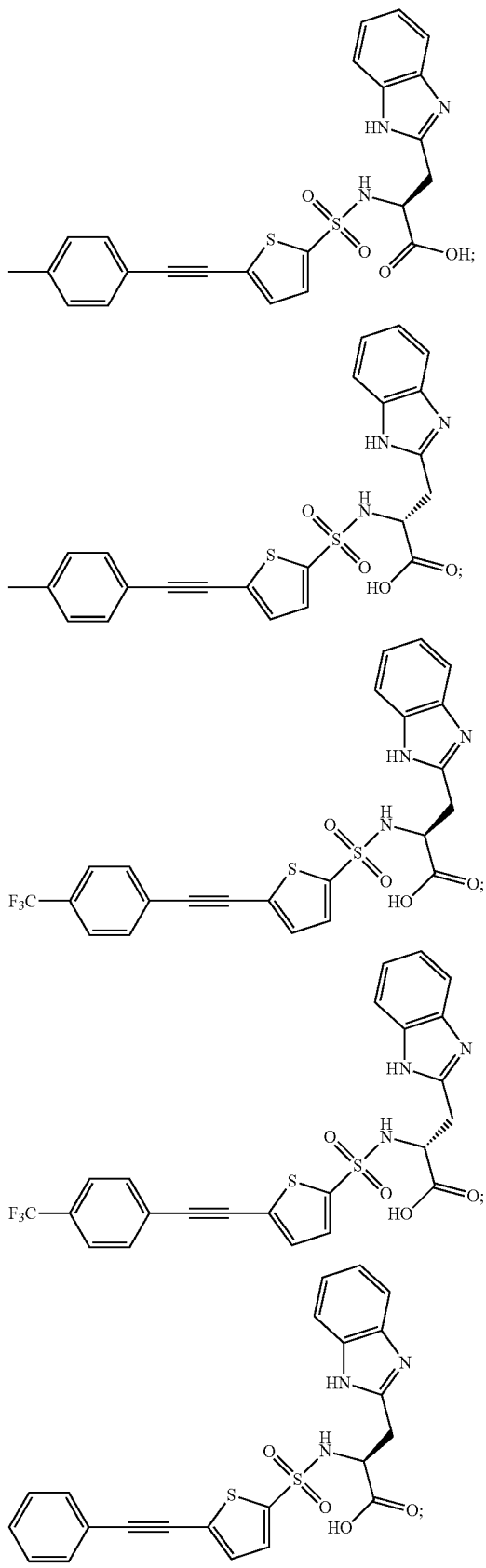

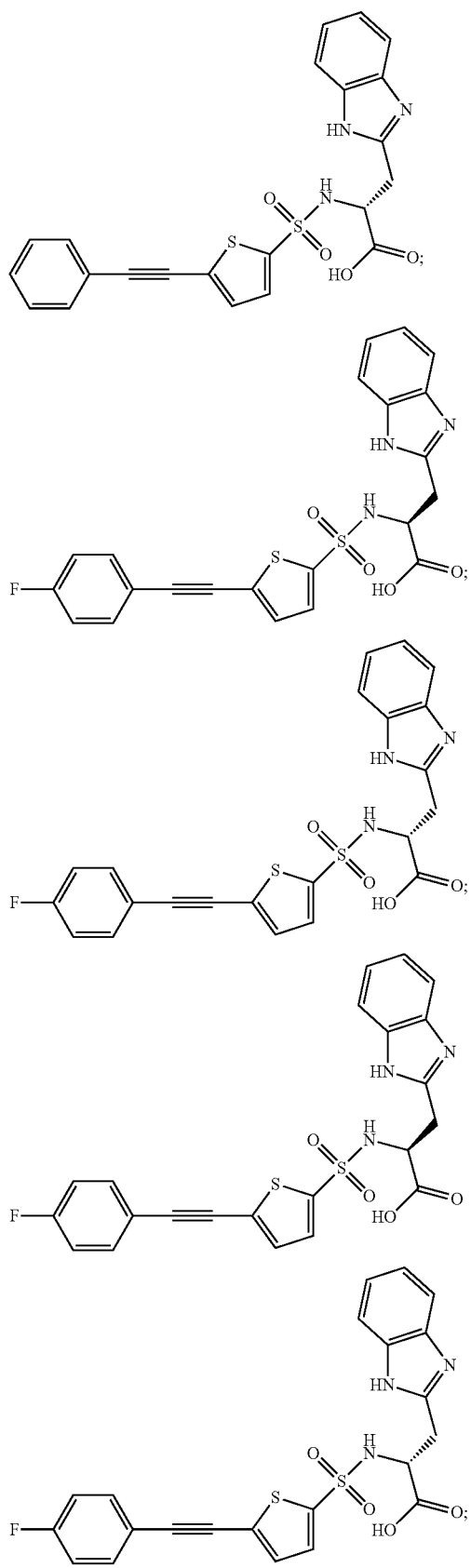 [SMILES: O=C(O)[C@@H](Cc1nc2ccccc2[nH]1)NS(=O)(=O)c1ccc(C#Cc2ccccc2)s1 ; O=C(O)[C@H](Cc1nc2ccccc2[nH]1)NS(=O)(=O)c1ccc(C#Cc2ccc(F)cc2)s1 ; O=C(O)[C@@H](Cc1nc2ccccc2[nH]1)NS(=O)(=O)c1ccc(C#Cc2ccc(F)cc2)s1 ; O=C(O)[C@H](Cc1nc2ccccc2[nH]1)NS(=O)(=O)c1ccc(C#Cc2ccc(F)cc2)s1 ; O=C(O)[C@@H](Cc1nc2ccccc2[nH]1)NS(=O)(=O)c1ccc(C#Cc2ccc(F)cc2)s1]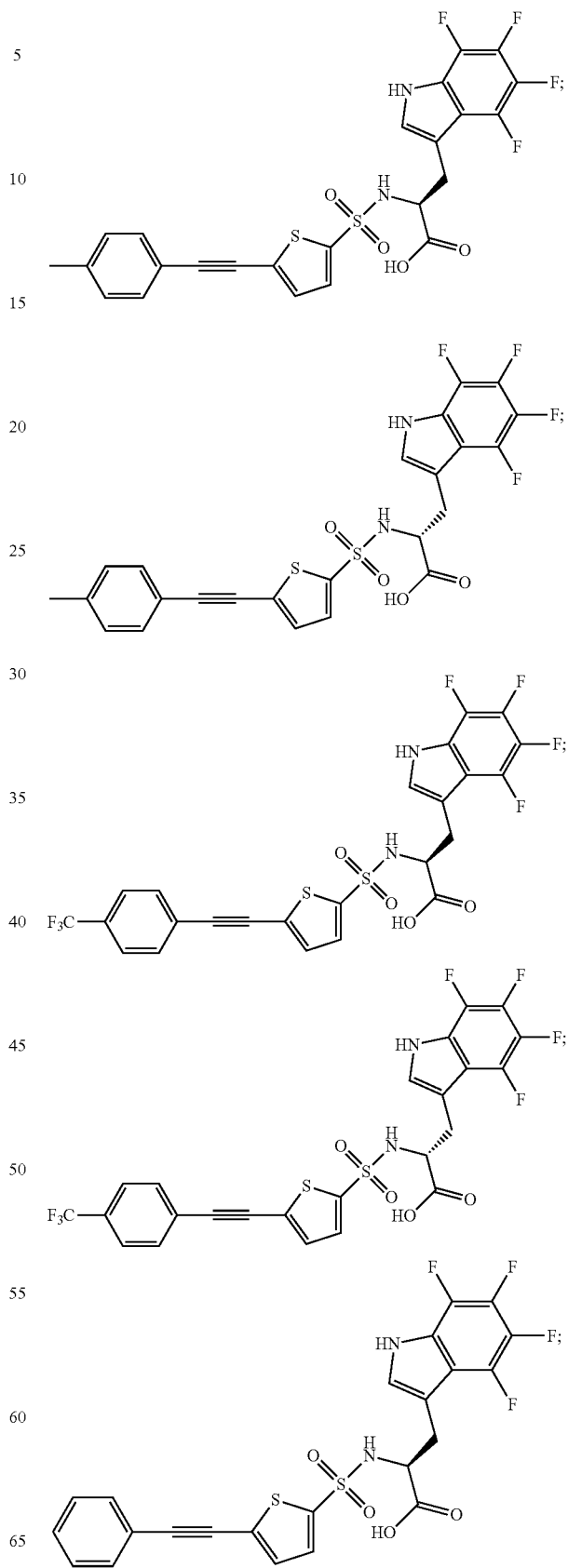

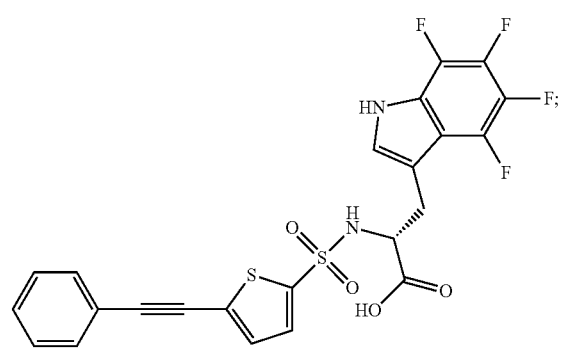
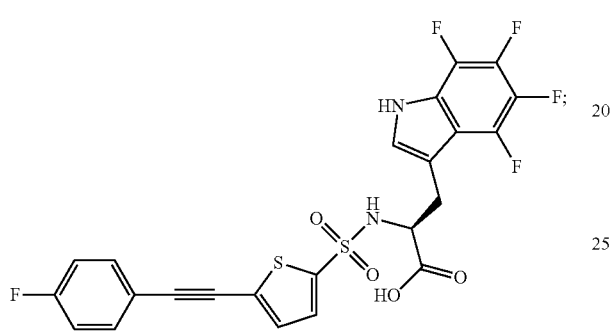
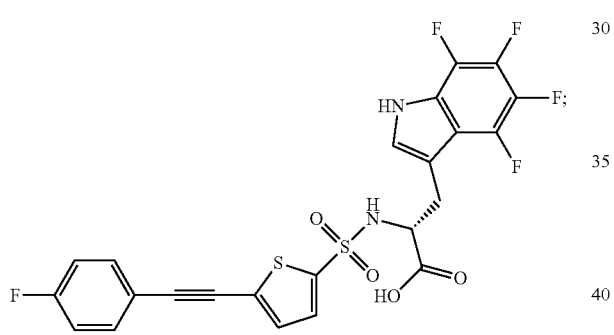
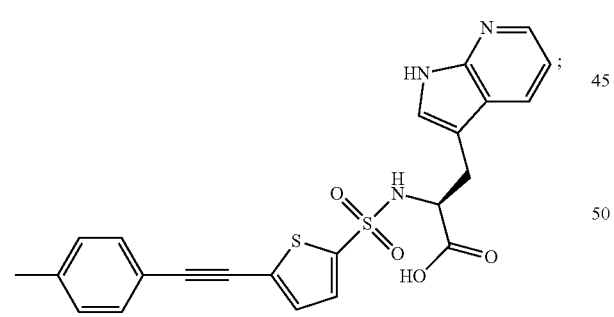
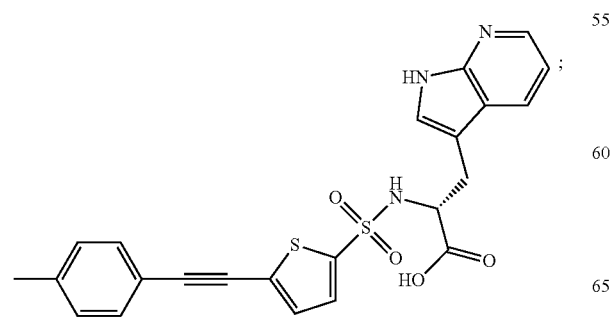
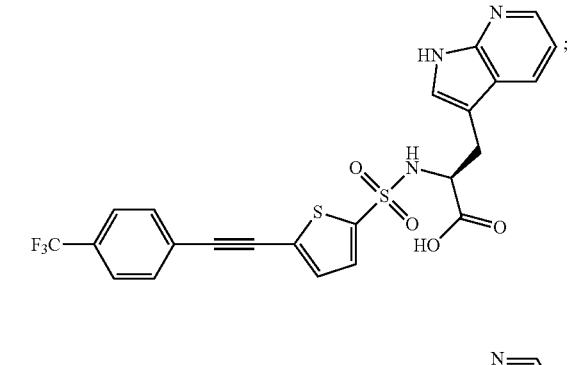
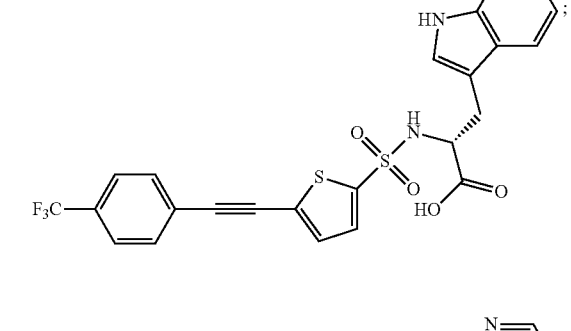
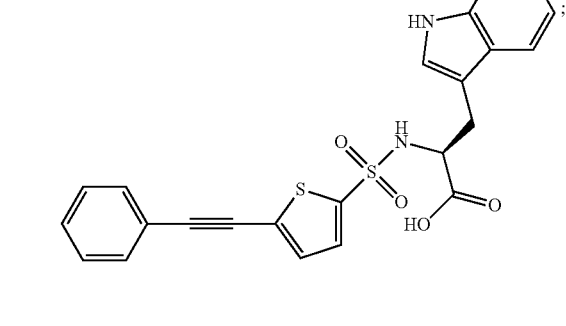
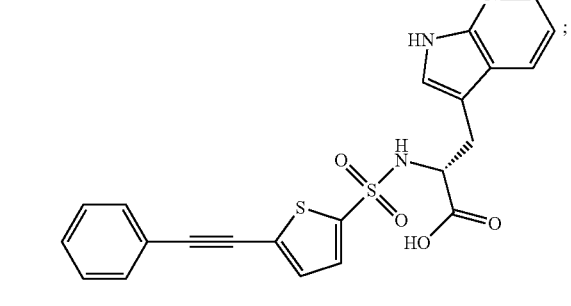
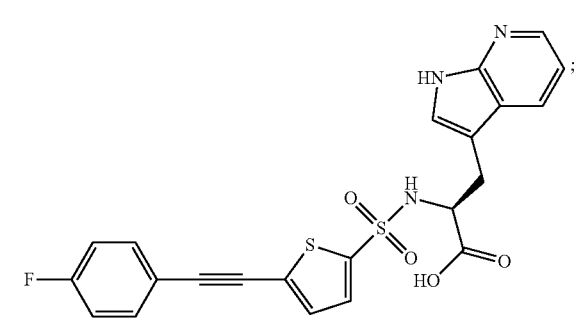

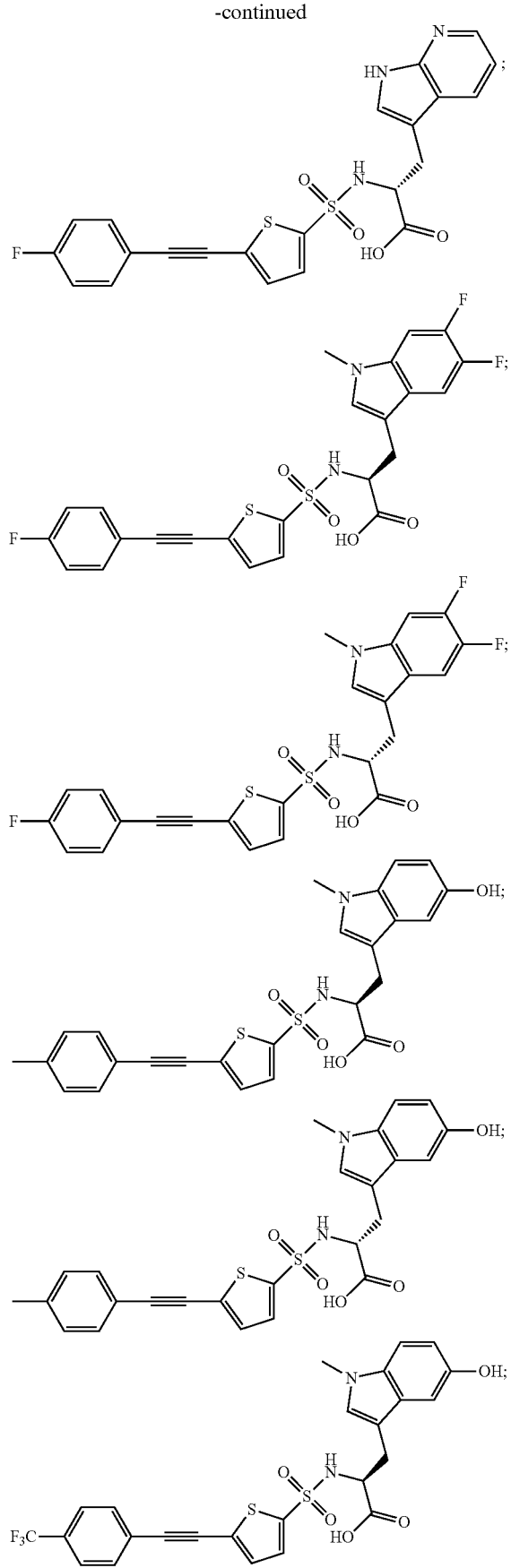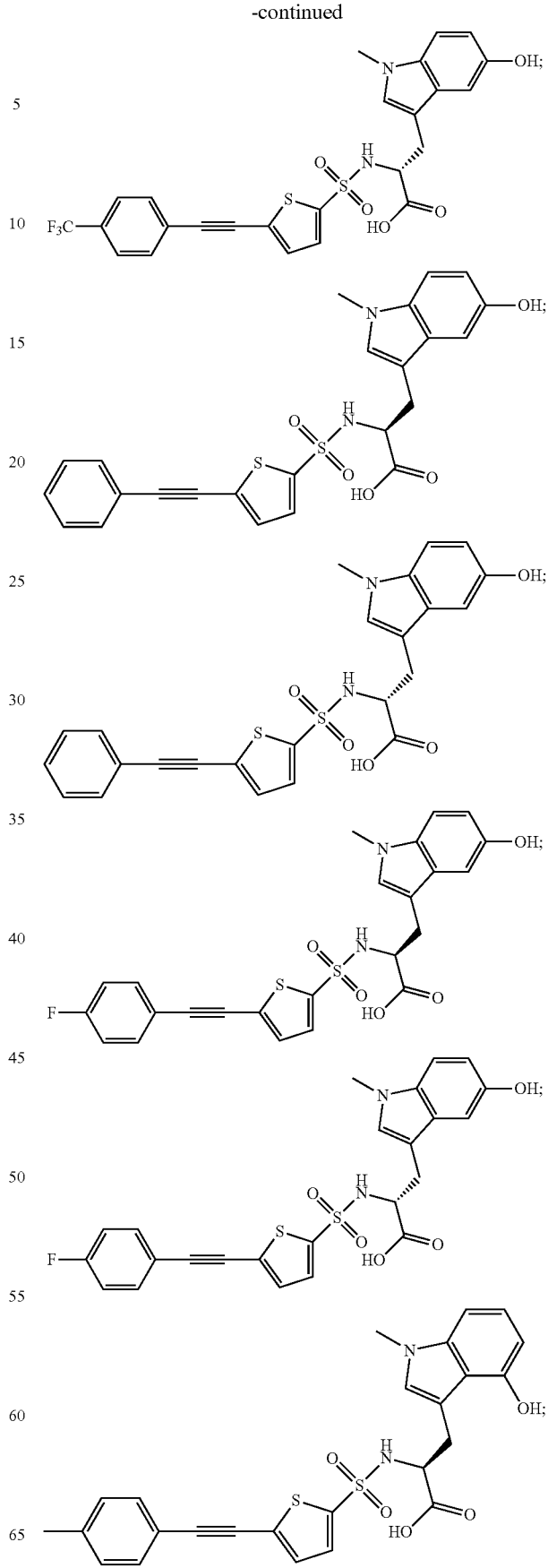

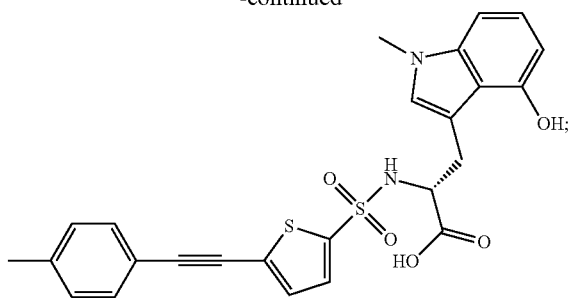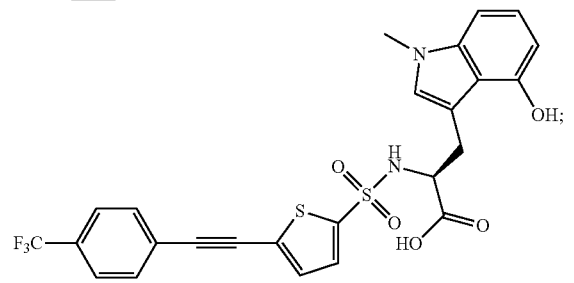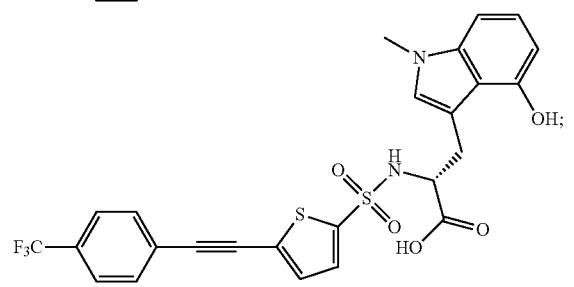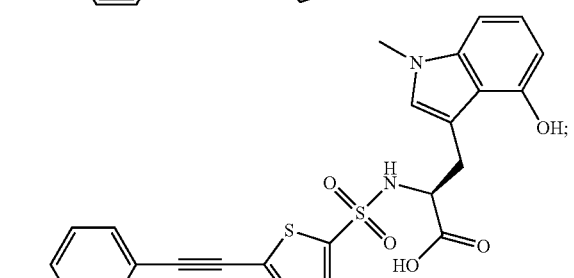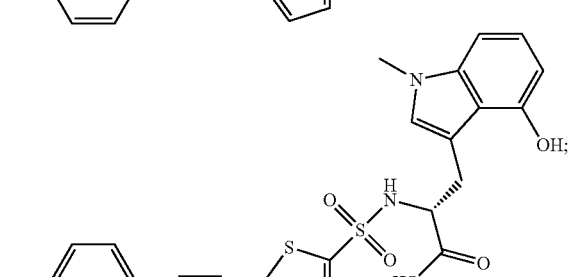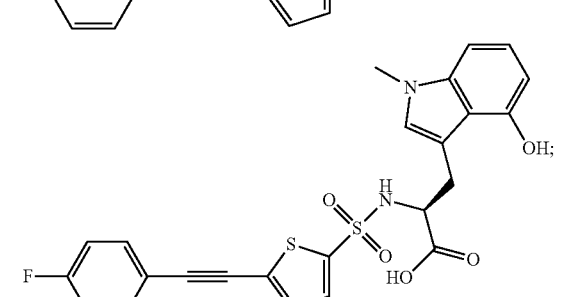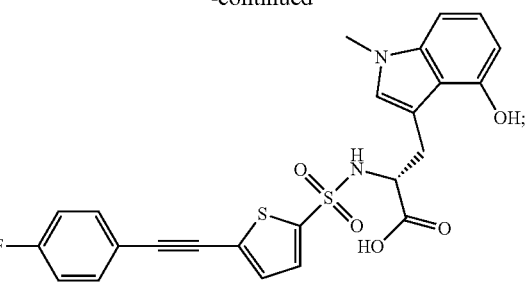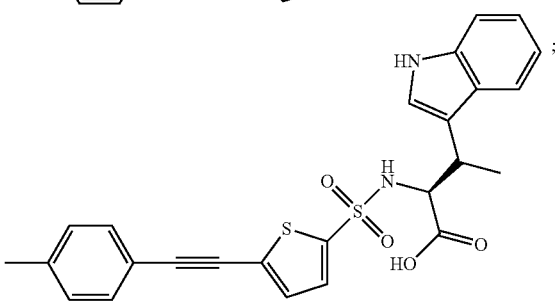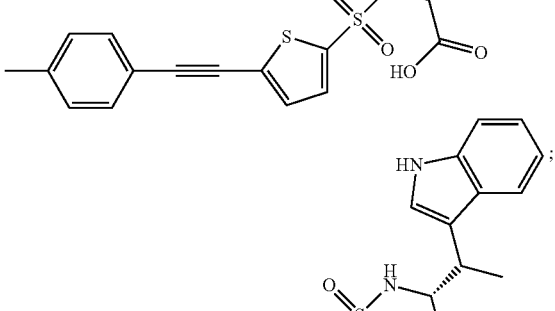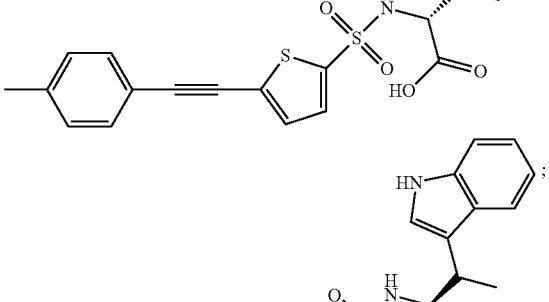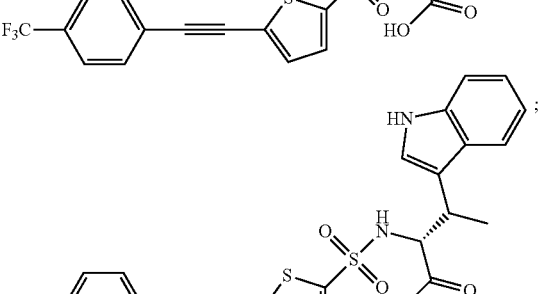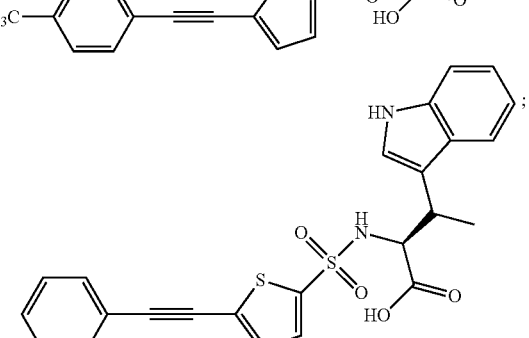

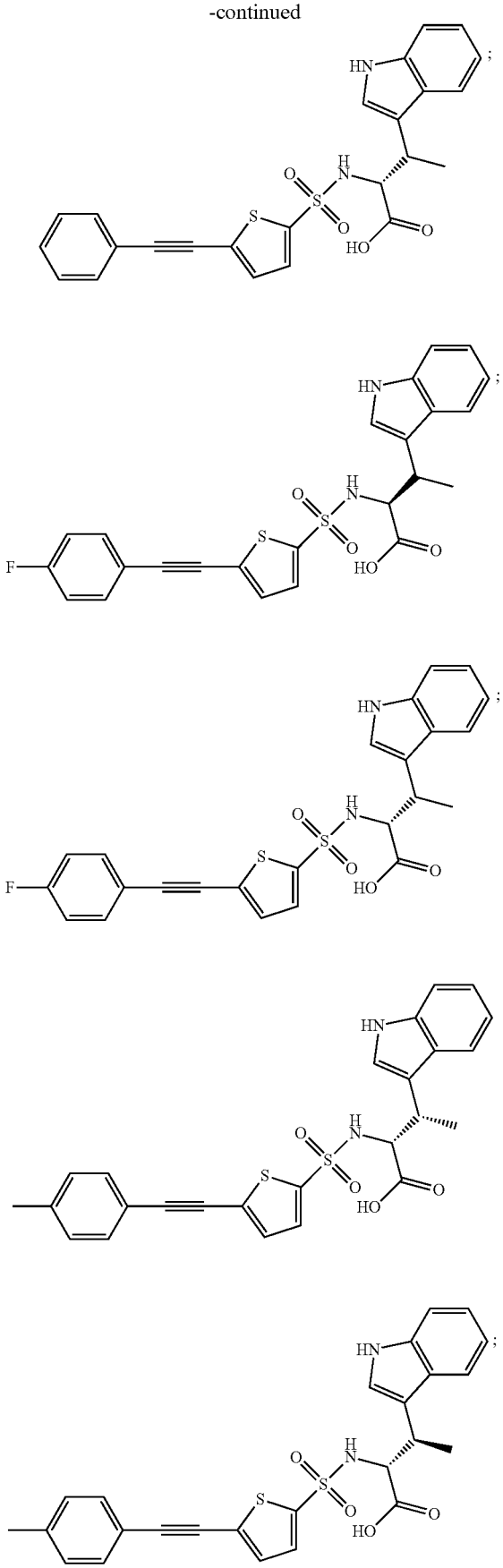
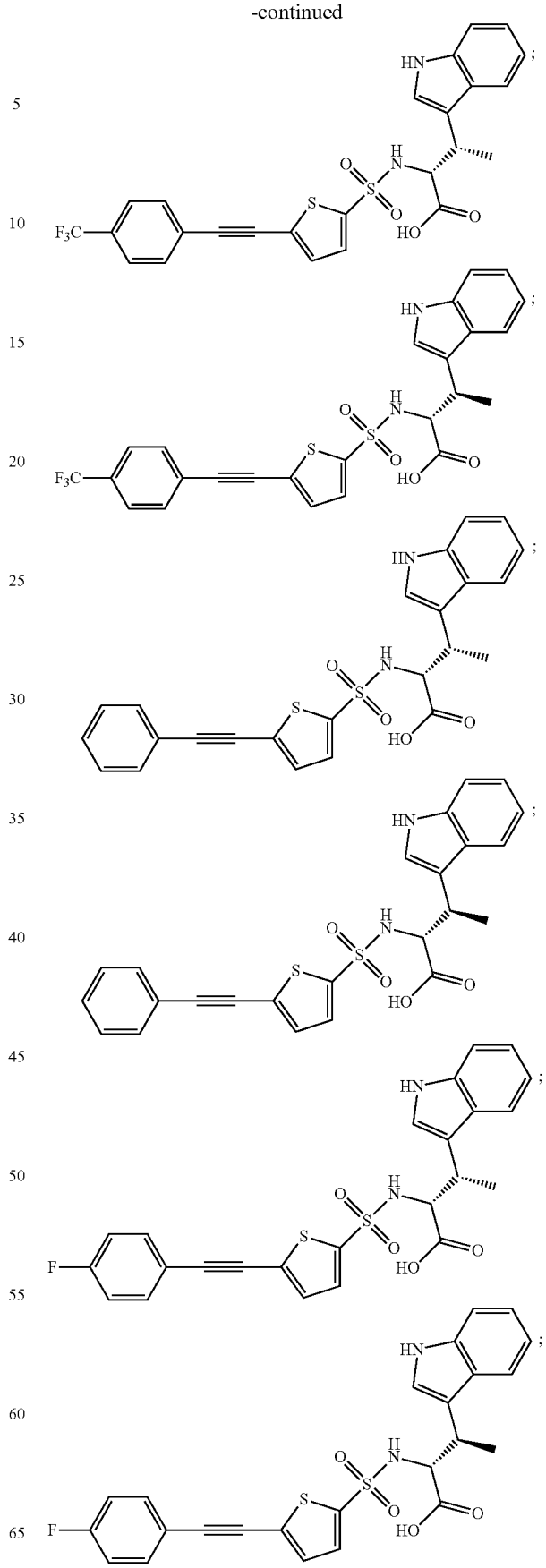

33
-continued
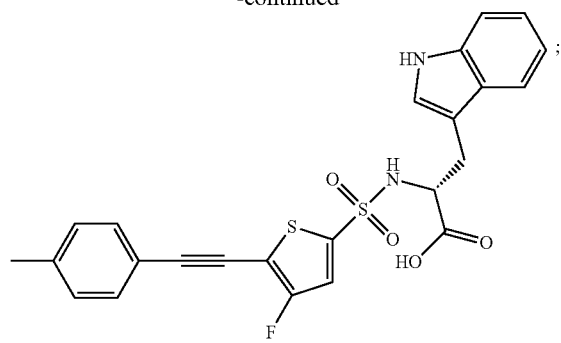
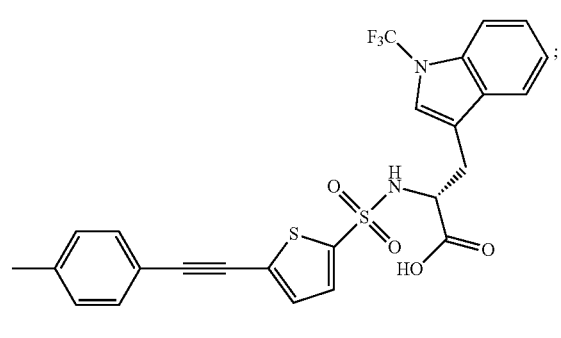
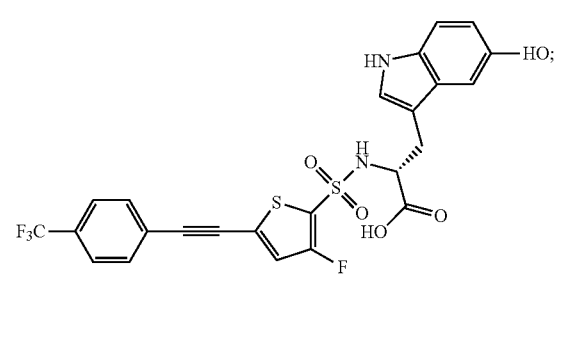
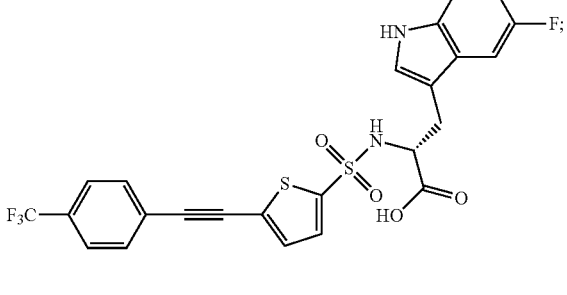
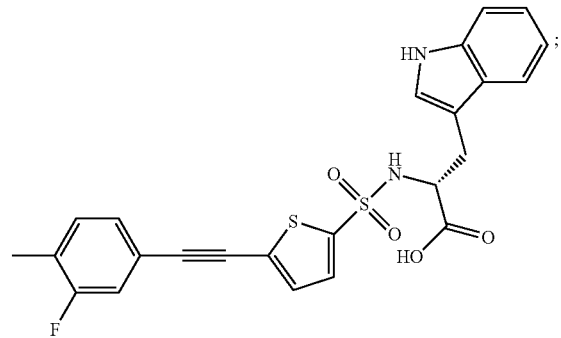
34
-continued
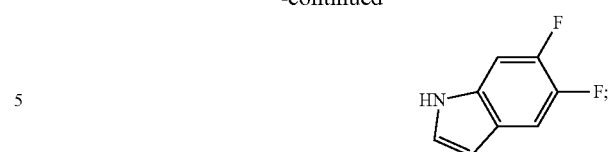
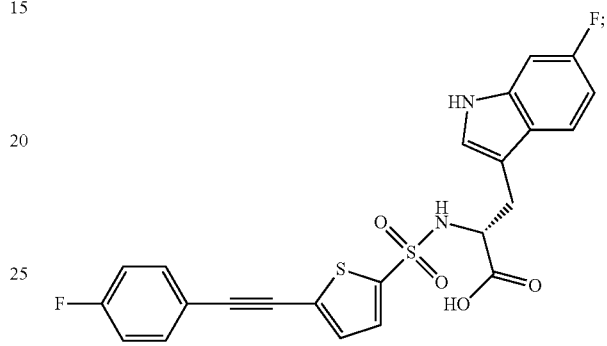
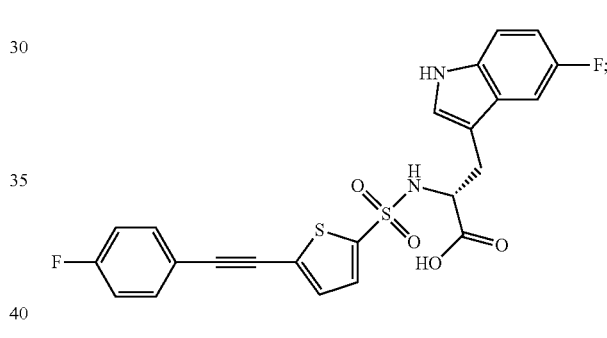
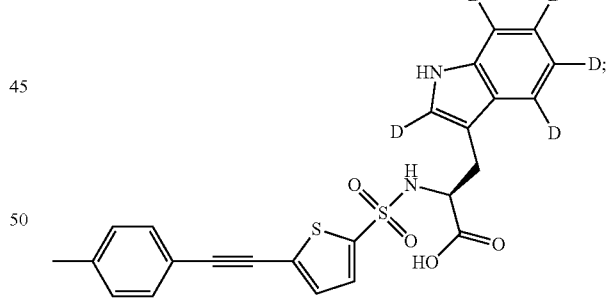
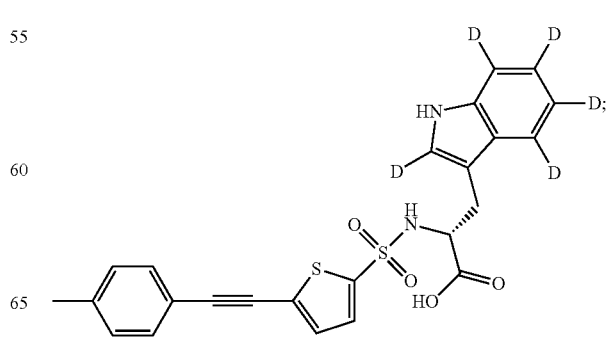

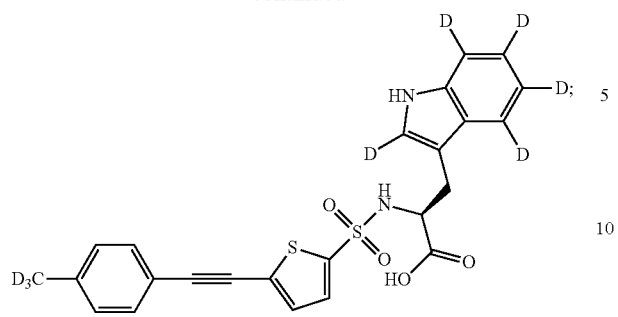
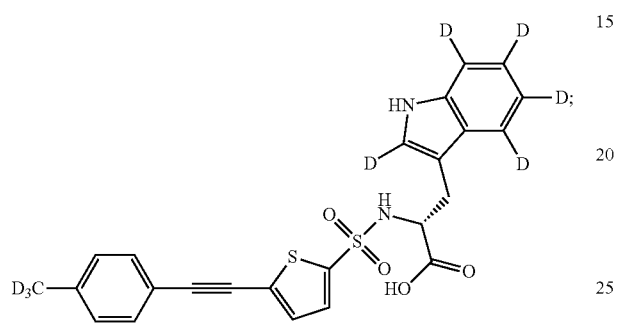
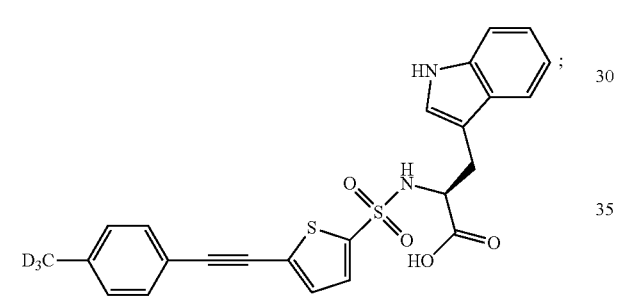
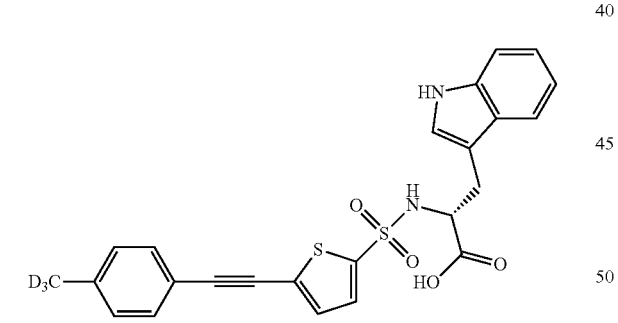
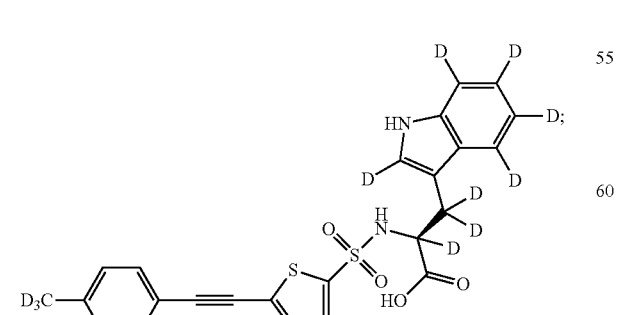
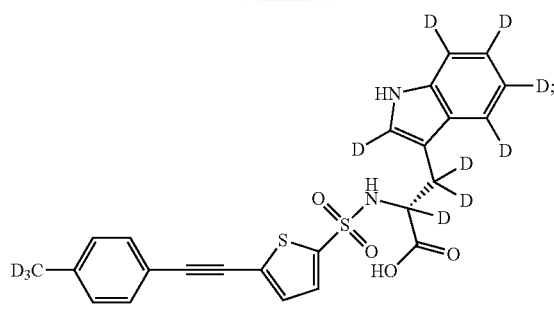
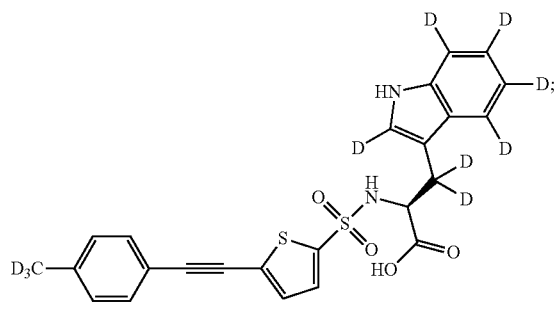
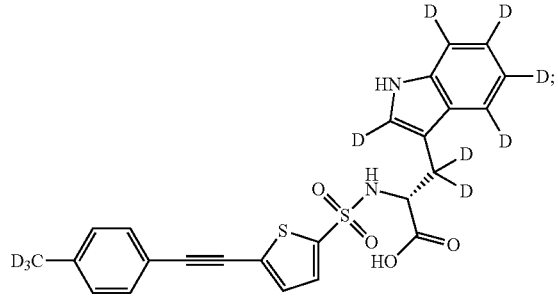
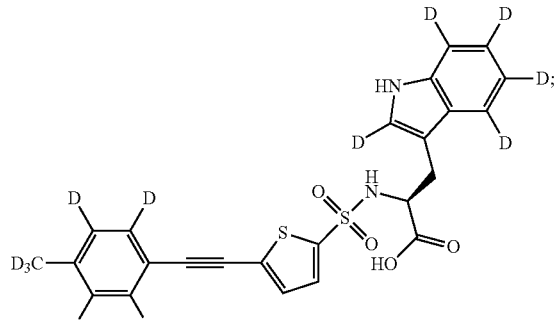
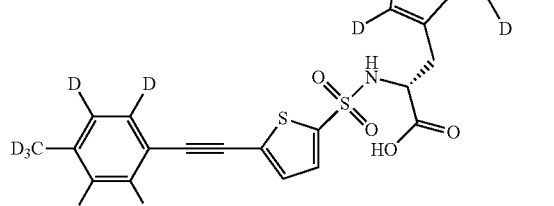

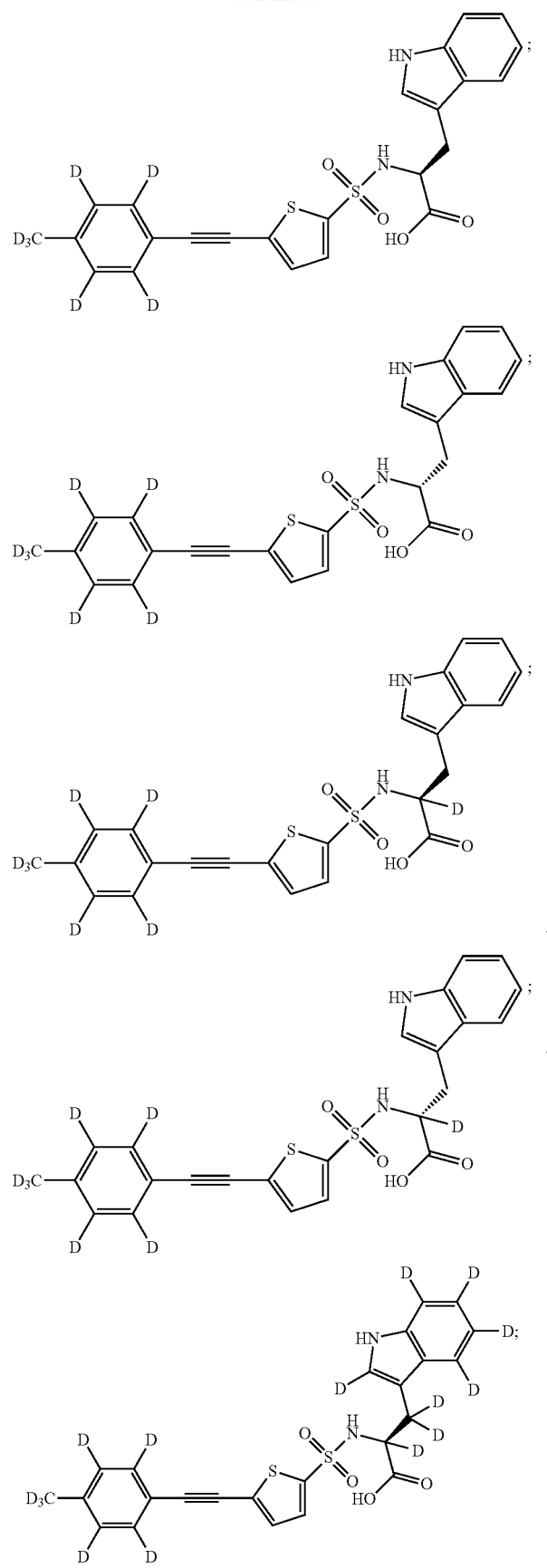
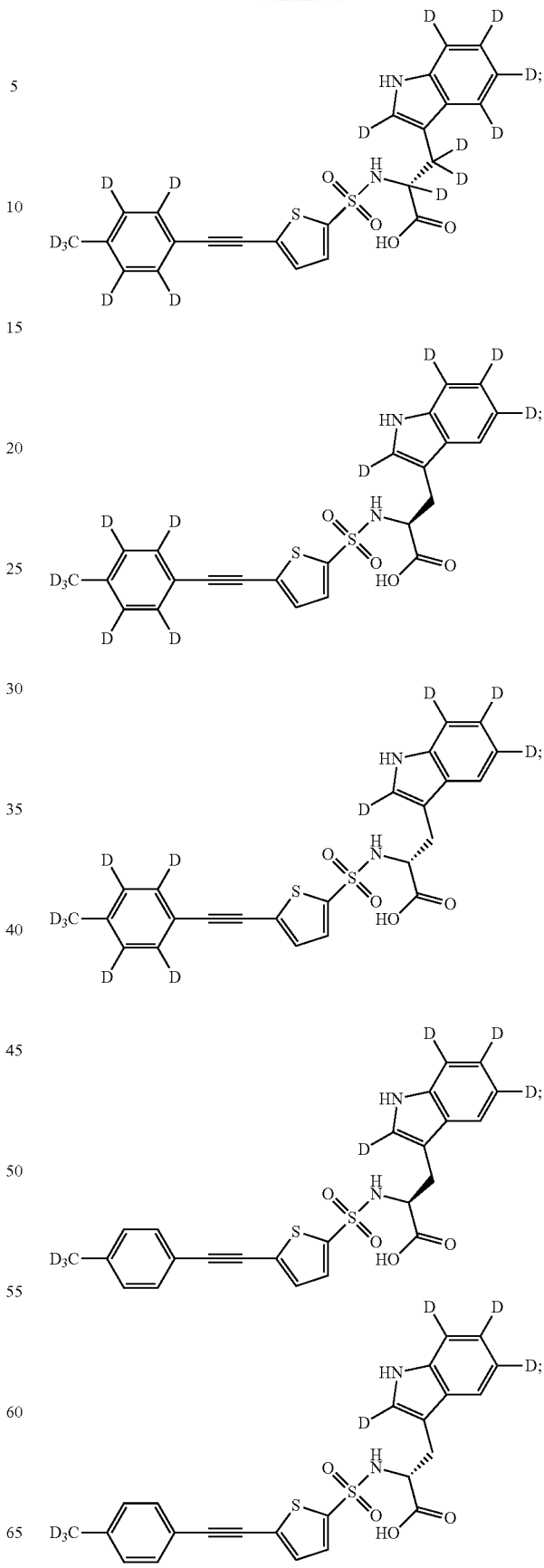

39
-continued
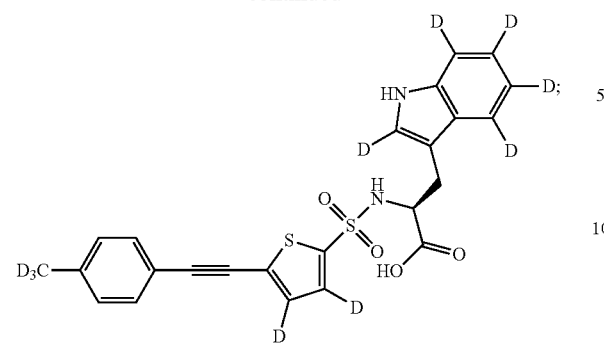
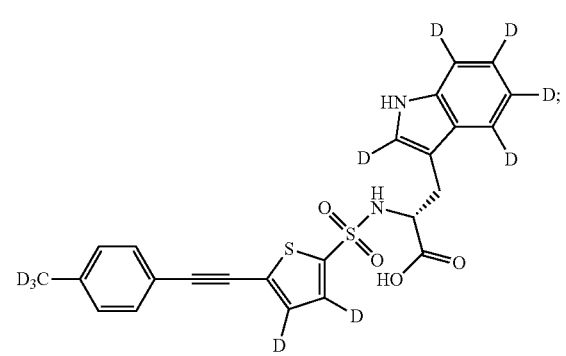
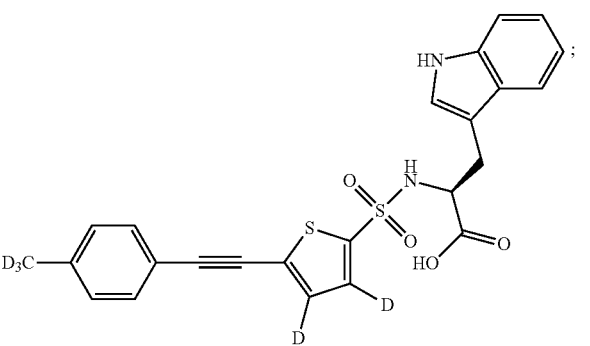
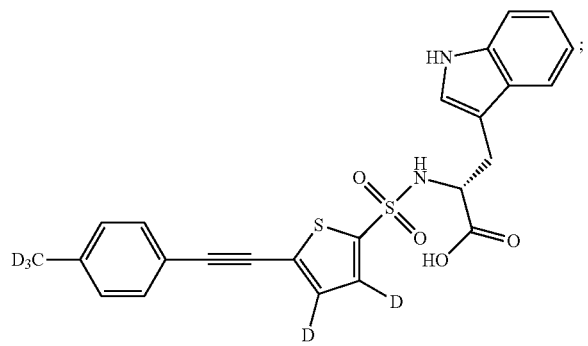
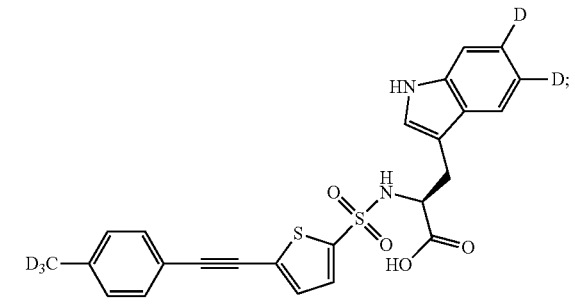
40
-continued
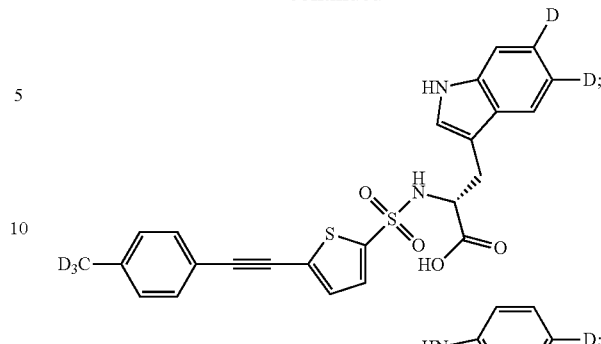
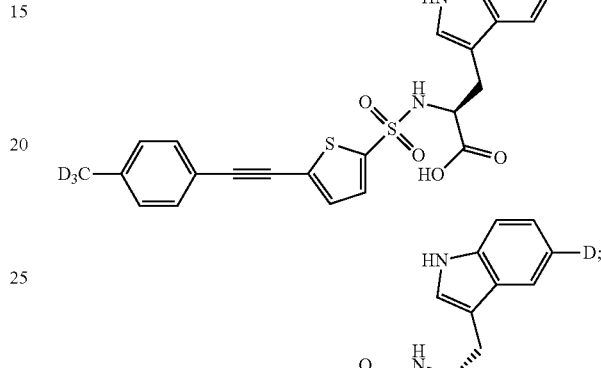
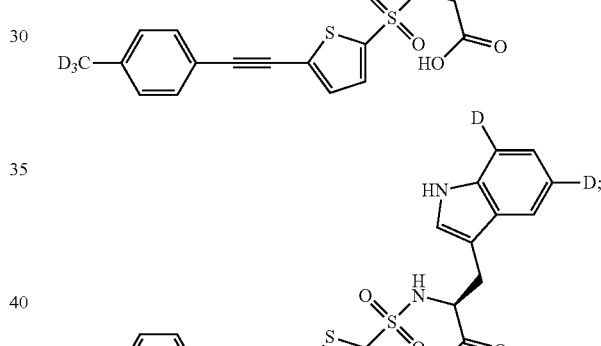
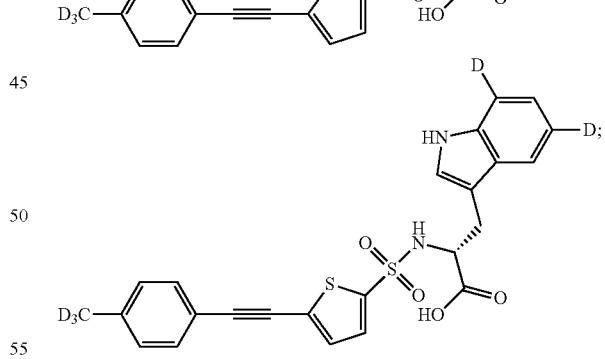
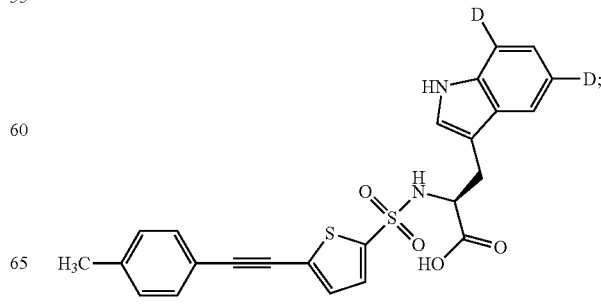

41
-continued
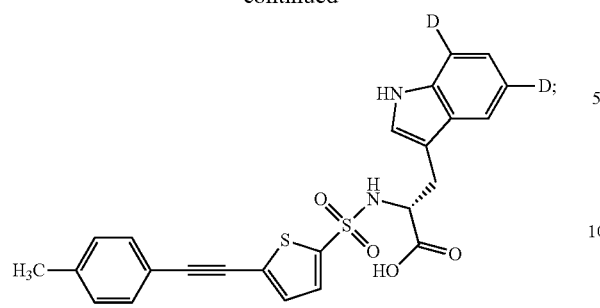
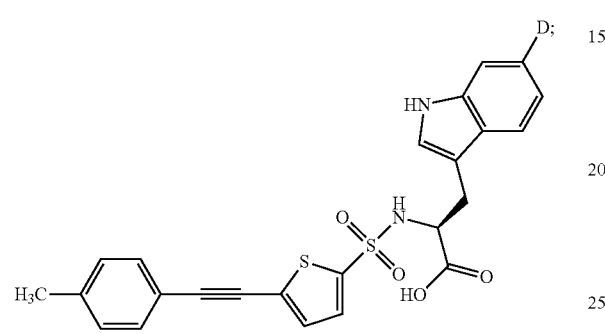
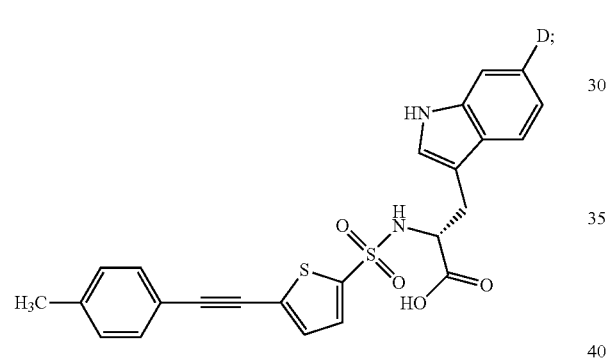
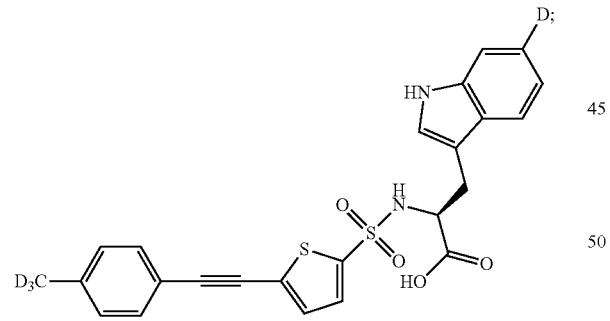
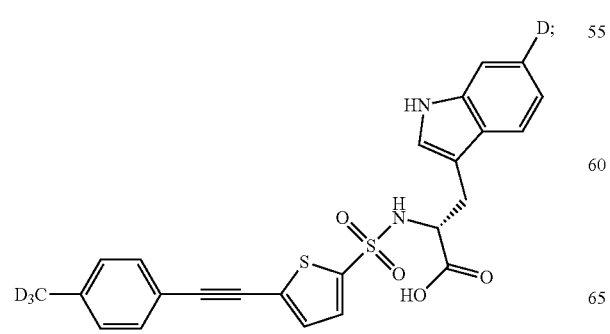
42
-continued
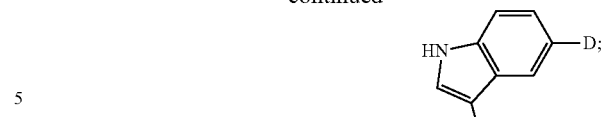
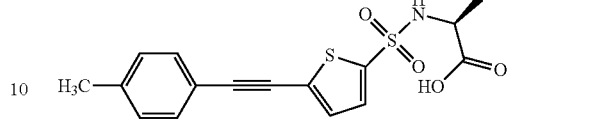
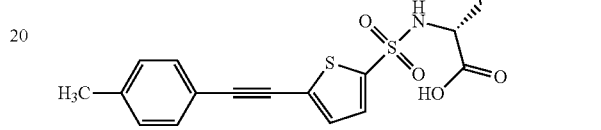
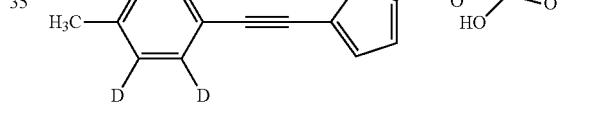

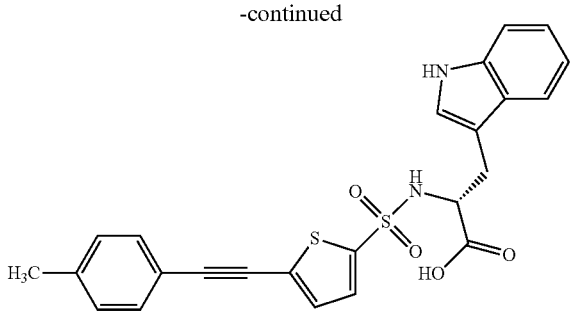

The present invention also is directed to pharmaceutical compositions including any of the MMP inhibiting compounds of the present invention described above. In accordance therewith, some embodiments of the present invention provide a pharmaceutical composition which may include an effective amount of a MMP inhibiting compound of the present invention and a pharmaceutically acceptable carrier.

The present invention also is directed to methods of inhibiting MMP-2 and/or MMP-9 and methods of treating diseases or symptoms mediated by an MMP-2 and/or MMP-9 enzyme. Such methods include administering a MMP-2 and/or MMP-9 inhibiting compound of the present invention, such as a compound of Formula (I) or Formula (II), as defined above, or an N-oxide, pharmaceutically acceptable salt or stereoisomer thereof. Examples of diseases or symptoms mediated by an MMP-2 and/or MMP-9 enzyme include, but are not limited to exaggerated sensitivity to pain, such as hyperalgesia, causalgia and allodynia; acute pain; burn pain; mechanically induced prain; atypical facial pain; neuropathic pain; back pain; complex regional pain syndromes I and II; arthritic joint pain; sports injury pain; pain related to viral infection, and post-herpetic neuralgia; phantom limb pain; labor pain; cancer pain; post-chemotherapy pain; post-stroke pain; post-operative pain; physiological pain; inflammatory pain; acute inflammatory conditions/visceral pain, angina, irritable bowel syndrome (IBS), and inflammatory bowel disease; neuropathic pain; neuralgia; painful diabetic neuropathy; traumatic nerve injury; spinal cord injury; and tolerance to narcotics or withdrawal from narcotics.

In some embodiments of the present invention, the MMP-2 and/or MMP-9 inhibiting compounds defined above are used in the manufacture of a medicament for the treatment of a disease mediated by an MMP-2 and/or MMP-9.

In some embodiments, the MMP-2 inhibiting compounds defined above may be used in combination with a drug, agent or therapeutic such as, but not limited to: (a) a disease modifying antirheumatic drug; (b) a nonsteroidal anti-inflammatory drug; (c) a COX-2 selective inhibitor; (d) a COX-1 inhibitor; (e) an immunosuppressive; (f) a steroid; (g) a biological response modifier; or (h) other anti-inflammatory agents or therapeutics useful for the treatment of chemokine mediated diseases.

Examples of disease modifying antirheumatic drugs include, but are not limited to, methotrexate, azathioptrineluflunomide, penicillamine, gold salts, mycophenolate, mofetil and cyclophosphamide.

Examples of nonsteroidal anti-inflammatory drugs include, but are not limited to, piroxicam, ketoprofen, naproxen, indomethacin, and ibuprofen.

Examples of COX-2 selective inhibitors include, but are not limited to, rofecoxib, celecoxib, and valdecoxib.

An example of a COX-1 inhibitor includes, but is not limited to, piroxicam.

Examples of immunosuppressives include, but are not limited to, methotrexate, cyclosporin, leflunimide, tacrolimus, rapamycin and sulfasalazine.

Examples of steroids include, but are not limited to, p-methasone, prednisone, cortisone, prednisolone and dexamethasone.

Examples of biological response modifiers include, but are not limited to, anti-TNF antibodies, TNF-α antagonists, IL-1 antagonists, anti-CD40, anti-CD28, IL-10 and anti-adhesion molecules.

Examples of anti-inflammatory agents or therapeutics include, but are not limited to, p38 kinase inhibitors, PDE4 inhibitors, TACE inhibitors, chemokine receptor antagonists, thalidomide, leukotriene inhibitors and other small molecule inhibitors of pro-inflammatory cytokine production.

In accordance with another embodiment of the present invention, a pharmaceutical composition may include an effective amount of a compound of the present invention, a pharmaceutically acceptable carrier and a drug, agent or therapeutic selected from: (a) a disease modifying antirheumatic drug; (b) a nonsteroidal anti-inflammatory drug; (c) a COX-2 selective inhibitor; (d) a COX-1 inhibitor; (e) an immunosuppressive; (f) a steroid; (g) a biological response modifier; or (h) other anti-inflammatory agents or therapeutics useful for the treatment of chemokine mediated diseases.

The MMP inhibiting activity of the MMP inhibiting compounds of the present invention may be measured using any suitable assay known in the art. A standard in vitro assay for MMP-2 inhibiting activity is described in Example 130 and for MMP-9 is described in Example 131. Additionally, standard in vitro assays for measuring MMP-1, MMP-7, MMP-3, MMP-12 and MMP-13 are described in Examples 132-136. Standard in vitro assays for measuring human and mouse microsomal stability is presented in Example 105. The in vivo pain inhibiting properties of the MMP inhibiting compounds of the present invention may be measured using any suitable animal model known in the art. A standard in vivo test for measuring neuropathic pain inhibition is described in Examples 110 and 111 and a test for measuring inflammatory pain is described in Example 120.

The MMP inhibiting compounds of the invention may have an inhibition activity ($IC_{50}$ MMP-2 and/or MMP-9) ranging from about 1 nM to about 20 μM, and typically, from about 1 nM to about 2 μM. The synthesis of MMP inhibiting compounds of the present invention and their biological assay are described in the following examples which are not intended to be limiting in any way.

EXAMPLES AND METHODS

Reagents were obtained from commercial sources and used without further purification unless otherwise stated. All reactions were performed using glassware that was oven dried overnight (100° C.). All solvents are of reagent grade. All reactions were carried out under nitrogen atmosphere unless otherwise stated. Organic reaction mixtures were concentrated using a Buchi rotary evaporator. Proton NMR spectra were recorded on a Varian Nuclear Magnetic Resonance spectrometer at 300 MHz.

SAX column was obtained from Luknova Inc (Manfield, Mass.). Procedure for Purification: SAX column was conditioned by addition of dichloromethane:MeOH (1:1). The eluante was dissolved in dichloromethane and loaded on to the SAX column. The column was washed with dichloromethane:MeOH (1:1) (3×50 mL) to remove the non-acidic impurities. The compound was eluted by passing 2N acetic acid in methanol. The solvent was evaporated and the target compound was further purified by reverse phase high pressure liquid chromatography (HPLC).

Liquid chromatography coupled to mass spectrometry (LC-MS): The following Instrument and specifications were used to analyze the various compounds.
Liquid Chromatography:
Instrument: Shimadzu LC-10AD VP
Column: Agilent Zobax 3.5☐ ☐SB-C18
Column internal diameter (ID): 4.6 mm
Column length: 50 mm
Gradient: 5% to 100% Acetonitrile and water both containing 0.1% formic acid.
Run time: 5 minutes
Flow rate: 1.5 ml/minute
High pressure: 4000 psi
Low pressure: 0 psi
Set temperature: 0° C.
Temperature Limit: 25° C.
LC-Mass Spec: Waters Micromass Quatro Ultima LC/MS (triple-quad MS), CTC Analytics PAL autosampler
Preparative, High Pressure Liquid Chromatography (Prep. HPLC): Revered Phase Preparative Purification Condition is as Follows:
Instrument: Waters UPLC system
Column: Waters Sunfire C18 Column
Column internal diameter (ID): 19 mm
Column length: 100 mm
Injection: 1 mL/DMSO
Gradient: 30% to 70% Methanol and water both containing 0.1% TFA.
Run time: 4 minutes
Flow rate: 40 ml/minute Example 1

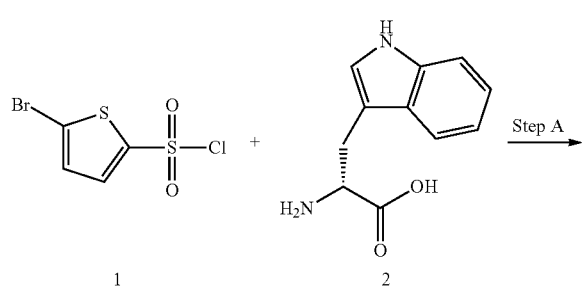

Step A

To a suspension of (R)-2-Amino-3-(1H-indol-3-yl)-propionic acid 2 (0.23 g, 1.12 mmol) (Alfa-Aesar, A-18426) in acetone (3 mL) was added 2M sodium carbonate (1 mL) to stir at room temperature for 30 minutes. To this mixture was added bromosulfonyl chloride 1 (0.13 g, 0.5 mmol) (Alfa-Aesar, A-14677) at 0° C. to stir for 15 minutes. The reaction mixture was stirred further for 1 hour at room temperature. After pouring into water (20 mL), the solution was washed with ether (×3). The aqueous layer was acidified with 1M HCl, followed by extraction with ethyl acetate (×3). The combined organic extracts were then washed with brine and dried (Na₂SO₄) to provide the crude (R)-2-(5-Bromo-thiophene-2-sulfonylamino)-3-(1H-indol-3-yl)-propionic acid product (3) (0.16 g, 74%). LC-MS (ES+) 429, 431; (ES−) 427, 429.

A portion of the crude (R)-2-(5-Bromo-thiophene-2-sulfonylamino)-3-(1H-indol-3-yl)-propionic acid product (3) was taken to the next step without further purification.

Example 2

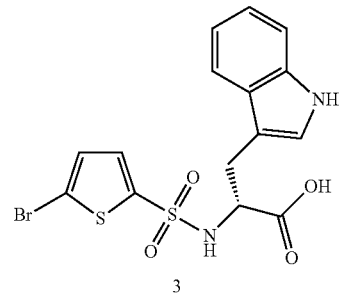

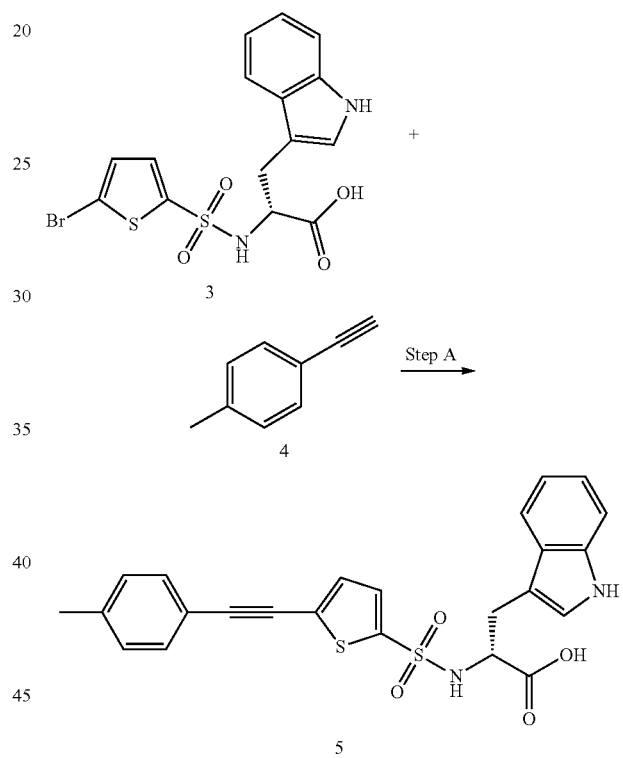

Step A

In a round bottom flask was added crude (R)-2-(5-Bromo-thiophene-2-sulfonylamino)-3-(1H-indol-3-yl)-propionic acid (3) (60 mg, 0.14 mmol), p-tolyl acetylene 4 (480 mg, 0.41 mmol), PdCl₂P(PPh₃)₂ (10 mg, 0.015 mmol), copper(I) iodide (2 mg, 0.01 mmol) and triethylamine (0.025 g, 0.25 mmol) and then dissolved in dry DMF (2 mL) under an atmosphere of nitrogen. The reaction mixture was then heated at 50° C. under a nitrogen atmosphere for 2 hours. The reaction mixture was then cooled to room temperature and diluted with ethyl acetate and washed with a solution composed of NaCl/NaHCO₃/(NH₄)₂CO₃/water (1:1:1:1) (×3), water, and then dried over sodium sulfate (Na₂SO₄). The crude product was purified using a SAX column to provide to give the desired (R)-3-(1H-Indol-3-yl)-2-(5-p-tolylethynyl-thiophene-2-sulfonylamino)-propionic acid 5 (0.036 g, 55%).

Example 2, Reaction A was repeated with same scale as above and then combined with the previous batch. The combined products were then further purified using preparative, reversed-phase-HPLC to give (R)-3-(1H-Indol-3-yl)-2-(5-p-tolylethynyl-thiophene-2-sulfonylamino)-propionic acid 5 having a purity of >95% by HPLC. LC-MS (ES+) 465; (ES−) 463; $^1$H NMR (300 MHz, DMSO-d6) δ 2.35 (s, 3H), 2.86-2.94 (m, 1H), 3.08-3.16 (m, 1H), 3.96-4.40 (m, 1H), 6.93-7.50 (m, 11H), 8.67 (d, 1H, J=8.7 Hz), 10.83 (s, 1H).

Example 3-15

If one were to follow a similar procedure as that described in Example 1, except using the commercially available (i.e. RSP amino acids, Chembridge, Sigma Aldrich, et al.) amino acids indicated in Table 1 below, the following compounds could be prepared.

TABLE 1

| Ex. # | Amino Acid | Sulphonamide Product |
|---|---|---|
| 3 | | |
| 4 | | |
| 5 | | |
| 6 | | |

TABLE 1-continued
| Ex. # | Amino Acid | Sulphonamide Product |
|---|---|---|
| 7 | 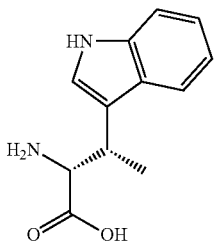 [SMILES: C[C@@H](c1c[nH]c2ccccc12)[C@@H](N)C(=O)O] | 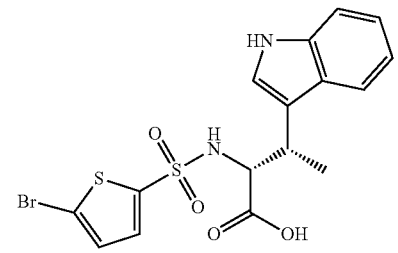 |
| 8 | 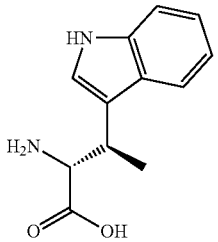 [SMILES: C[C@H](c1c[nH]c2ccccc12)[C@@H](N)C(=O)O] | 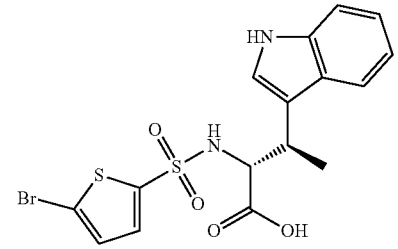 [SMILES: C[C@H](c1c[nH]c2ccccc12)[C@@H](NS(=O)(=O)c1ccc(Br)s1)C(=O)O] |
| 9 | 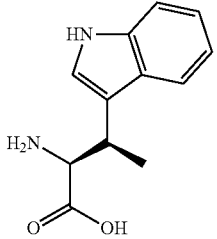 [SMILES: C[C@H](c1c[nH]c2ccccc12)[C@H](N)C(=O)O] | 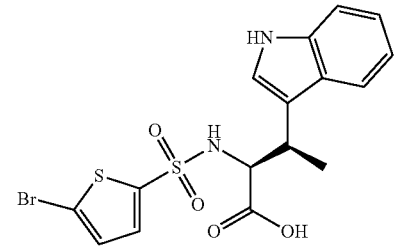 [SMILES: C[C@H](c1c[nH]c2ccccc12)[C@H](NS(=O)(=O)c1ccc(Br)s1)C(=O)O] |
| 10 | 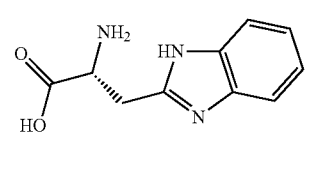 [SMILES: N[C@H](Cc1nc2ccccc2[nH]1)C(=O)O] | 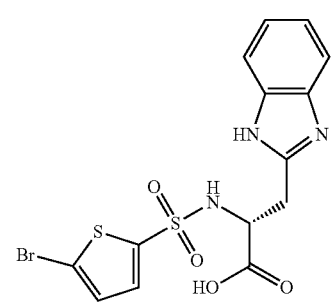 [SMILES: O=C(O)[C@@H](Cc1nc2ccccc2[nH]1)NS(=O)(=O)c1ccc(Br)s1] |
| 11 | 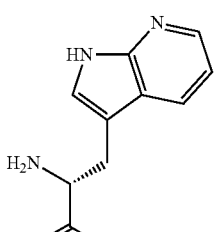 | 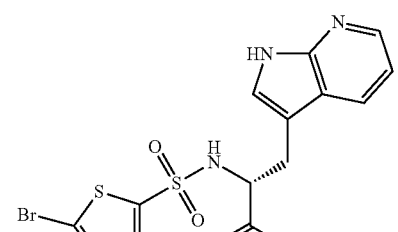 |

TABLE 1-continued
| Ex. # | Amino Acid | Sulphonamide Product |
|---|---|---|
| 12 | 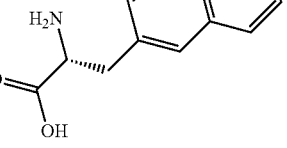 | 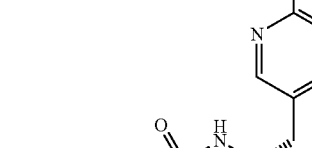 |
| 13 | 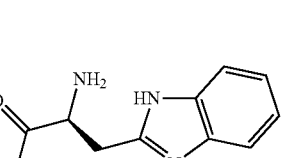 |  |
| 14 |  | 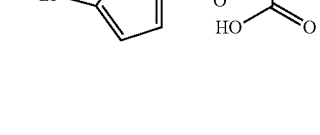 |
| 15 | 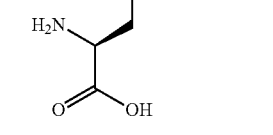 | 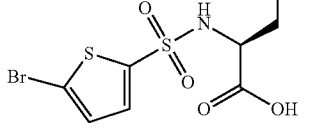 |

Example 16-28
If one were to follow a similar procedure as that described in Example 2, except using the commercially available p-tolylacetylene (Sigma Aldrich) and the sulfonamides (Example 3-15, Table 1) indicated in Table 2 below, the following compounds could be prepared.
TABLE 2
| Ex. # | Sulphonamide | Phenylethynyl-thiophene Coupled Product |
|---|---|---|
| 16 | 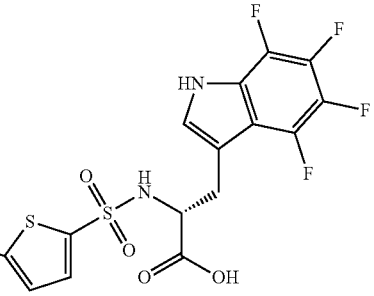 | 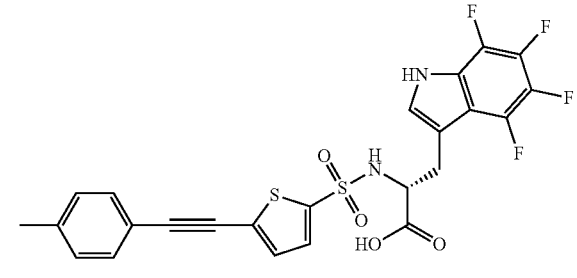 [SMILES: Cc1ccc(C#Cc2ccc(S(=O)(=O)N[C@H](Cc3c[nH]c4c(F)c(F)c(F)c(F)c34)C(=O)O)s2)cc1] |
| 17 | 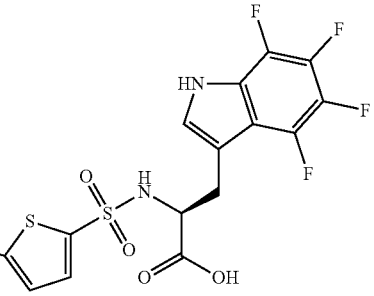 | 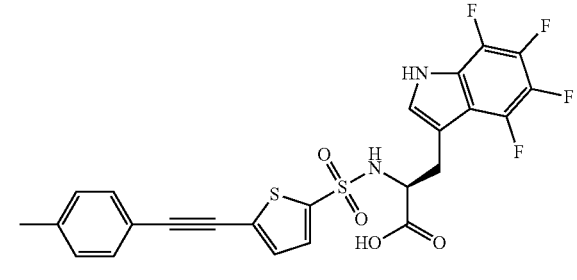 [SMILES: Cc1ccc(C#Cc2ccc(S(=O)(=O)N[C@@H](Cc3c[nH]c4c(F)c(F)c(F)c(F)c34)C(=O)O)s2)cc1] |
| 18 | 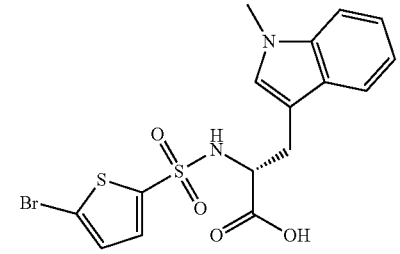 [SMILES: Cn1cc(C[C@@H](NS(=O)(=O)c2ccc(Br)s2)C(=O)O)c2ccccc21] | 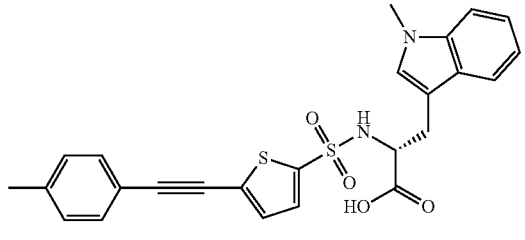 [SMILES: Cc1ccc(C#Cc2ccc(S(=O)(=O)N[C@H](Cc3cn(C)c4ccccc34)C(=O)O)s2)cc1] |
| 19 | 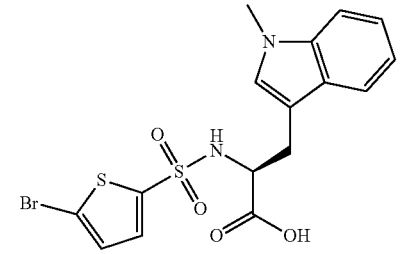 [SMILES: Cn1cc(C[C@H](NS(=O)(=O)c2ccc(Br)s2)C(=O)O)c2ccccc21] | 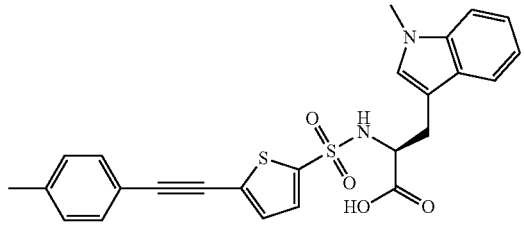 [SMILES: Cc1ccc(C#Cc2ccc(S(=O)(=O)N[C@@H](Cc3cn(C)c4ccccc34)C(=O)O)s2)cc1] |
| 20 | 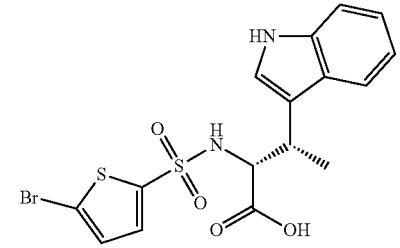 [SMILES: C[C@@H](c1c[nH]c2ccccc12)[C@@H](NS(=O)(=O)c1ccc(Br)s1)C(=O)O] | 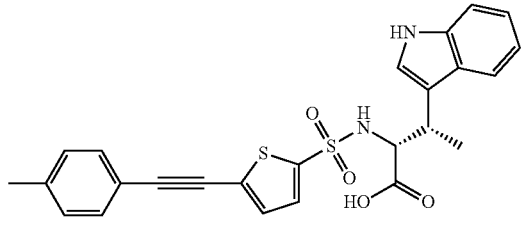 [SMILES: Cc1ccc(C#Cc2ccc(S(=O)(=O)N[C@@H](C(=O)O)[C@@H](C)c3c[nH]c4ccccc34)s2)cc1] |

TABLE 2-continued
| Ex. # | Sulphonamide | Phenylethynyl-thiophene Coupled Product |
|---|---|---|
| 21 | 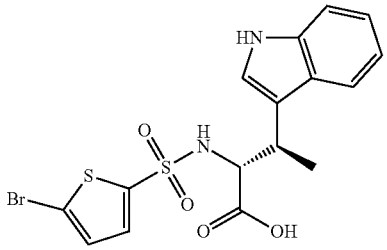 [SMILES: C[C@H](c1c[nH]c2ccccc12)[C@@H](NS(=O)(=O)c1ccc(Br)s1)C(=O)O] | 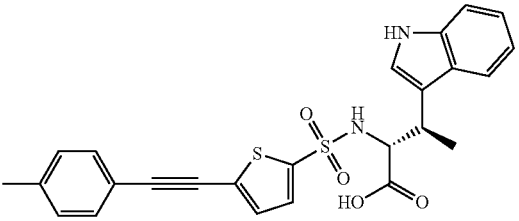 [SMILES: Cc1ccc(C#Cc2ccc(S(=O)(=O)N[C@@H](C(=O)O)[C@H](C)c3c[nH]c4ccccc34)s2)cc1] |
| 22 | 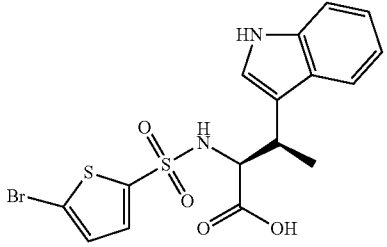 [SMILES: C[C@H](c1c[nH]c2ccccc12)[C@H](NS(=O)(=O)c1ccc(Br)s1)C(=O)O] | 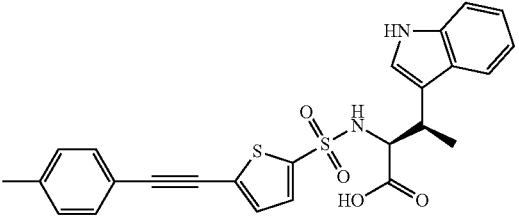 [SMILES: Cc1ccc(C#Cc2ccc(S(=O)(=O)N[C@H](C(=O)O)[C@H](C)c3c[nH]c4ccccc34)s2)cc1] |
| 23 | 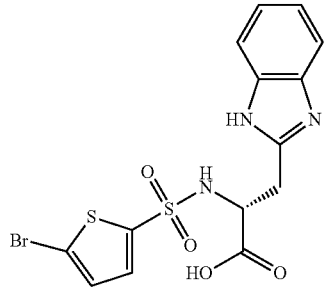 [SMILES: O=C(O)[C@@H](Cc1nc2ccccc2[nH]1)NS(=O)(=O)c1ccc(Br)s1] | 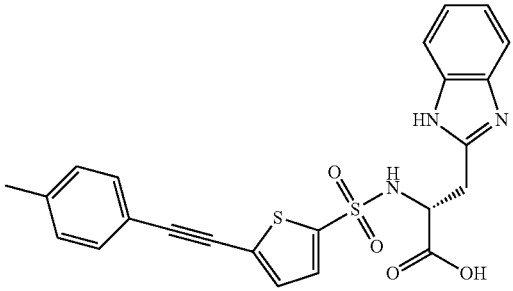 [SMILES: Cc1ccc(C#Cc2ccc(S(=O)(=O)N[C@H](Cc3nc4ccccc4[nH]3)C(=O)O)s2)cc1] |
| 24 | 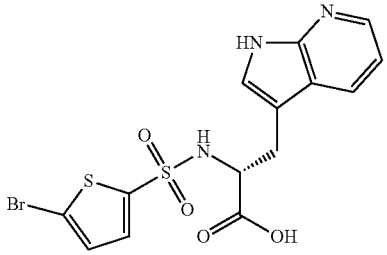 [SMILES: O=C(O)[C@@H](Cc1c[nH]c2ncccc12)NS(=O)(=O)c1ccc(Br)s1] | 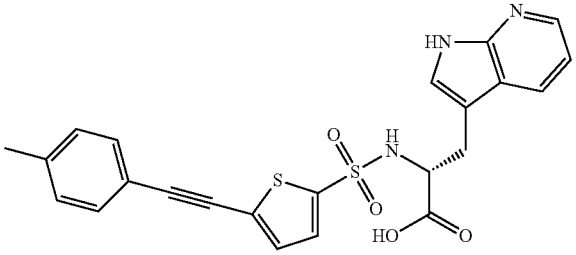 [SMILES: Cc1ccc(C#Cc2ccc(S(=O)(=O)N[C@H](Cc3c[nH]c4ncccc34)C(=O)O)s2)cc1] |
| 25 | 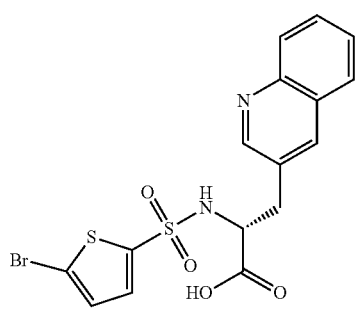 [SMILES: O=C(O)[C@@H](Cc1cnc2ccccc2c1)NS(=O)(=O)c1ccc(Br)s1] | 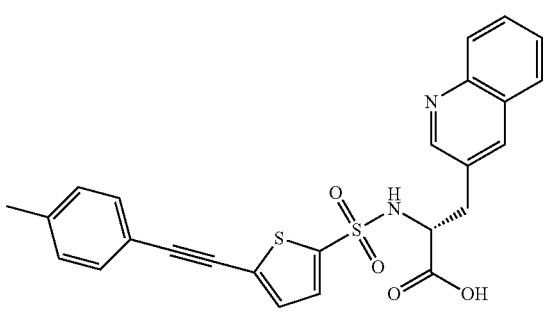 [SMILES: Cc1ccc(C#Cc2ccc(S(=O)(=O)N[C@H](Cc3cnc4ccccc4c3)C(=O)O)s2)cc1] |

TABLE 2-continued

| Ex. # | Sulphonamide | Phenylethynyl-thiophene Coupled Product |
|---|---|---|
| 26 | 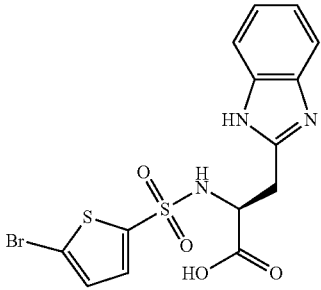 [SMILES: O=C(O)[C@H](Cc1nc2ccccc2[nH]1)NS(=O)(=O)c1ccc(Br)s1] | 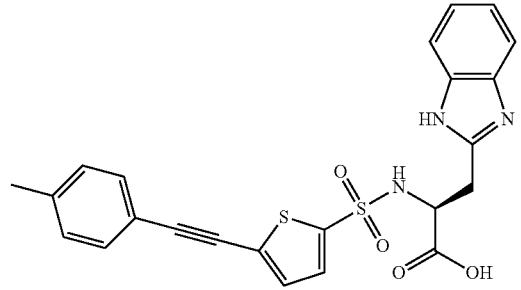 [SMILES: Cc1ccc(C#Cc2ccc(S(=O)(=O)N[C@@H](Cc3nc4ccccc4[nH]3)C(=O)O)s2)cc1] |
| 27 | 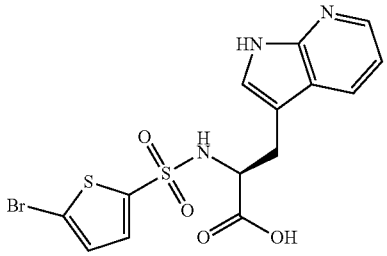 [SMILES: O=C(O)[C@H](Cc1c[nH]c2ncccc12)NS(=O)(=O)c1ccc(Br)s1] | 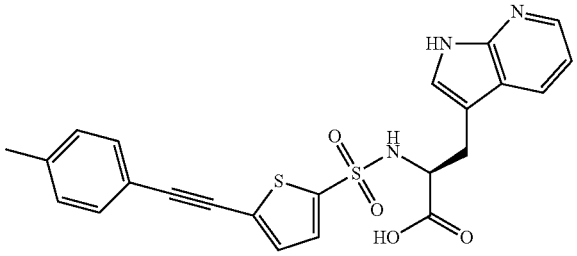 [SMILES: Cc1ccc(C#Cc2ccc(S(=O)(=O)N[C@@H](Cc3c[nH]c4ncccc34)C(=O)O)s2)cc1] |
| 28 | 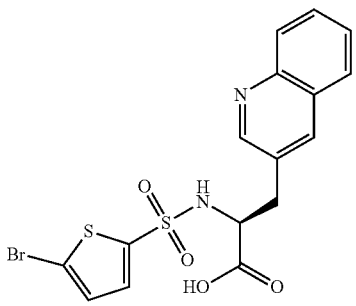 [SMILES: O=C(O)[C@H](Cc1cnc2ccccc2c1)NS(=O)(=O)c1ccc(Br)s1] | 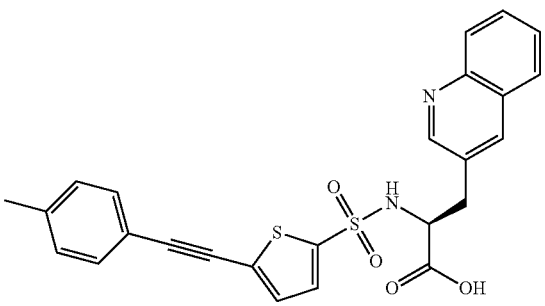 [SMILES: Cc1ccc(C#Cc2ccc(S(=O)(=O)N[C@@H](Cc3cnc4ccccc4c3)C(=O)O)s2)cc1] |

Example 29-41

If one were to follow a similar procedure as that described in Example 2, except using the commercially available p-fluorophenylacetylene (Sigma Aldrich, cat. #404330) and the synthesized sulfonamides (Example 3-15, Table 1) indicated in Table 3 below, the following compounds could be prepared.

TABLE 3

| Ex.# | Sulphonamide | Phenylethynyl-thiophene Coupled Product |
|---|---|---|
| 29 | 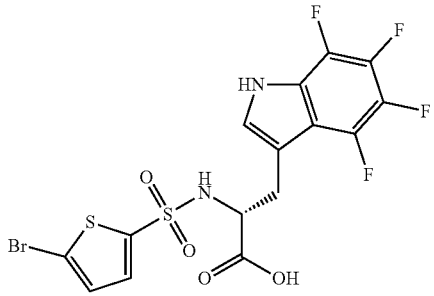 [SMILES: O=C(O)[C@@H](Cc1c[nH]c2c(F)c(F)c(F)c(F)c12)NS(=O)(=O)c1ccc(Br)s1] | 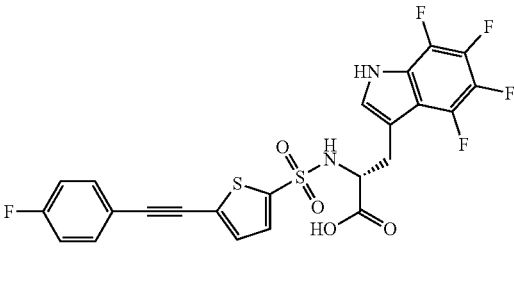 [SMILES: O=C(O)[C@@H](Cc1c[nH]c2c(F)c(F)c(F)c(F)c12)NS(=O)(=O)c1ccc(C#Cc2ccc(F)cc2)s1] |

TABLE 3-continued
| Ex.# | Sulphonamide | Phenylethynyl-thiophene Coupled Product |
|---|---|---|
| 30 | 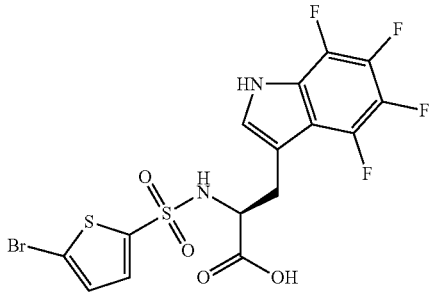 [SMILES: O=C(O)[C@H](Cc1c[nH]c2c(F)c(F)c(F)c(F)c12)NS(=O)(=O)c1ccc(Br)s1] | 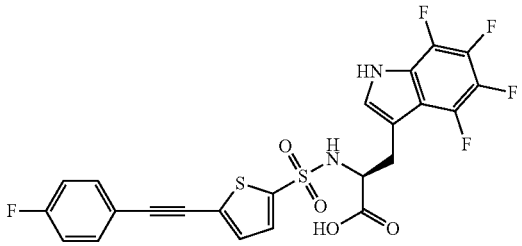 [SMILES: O=C(O)[C@H](Cc1c[nH]c2c(F)c(F)c(F)c(F)c12)NS(=O)(=O)c1ccc(C#Cc2ccc(F)cc2)s1] |
| 31 | 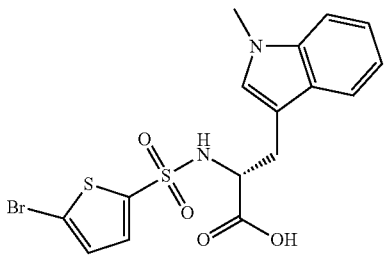 [SMILES: Cn1cc(C[C@@H](NS(=O)(=O)c2ccc(Br)s2)C(=O)O)c2ccccc21] | 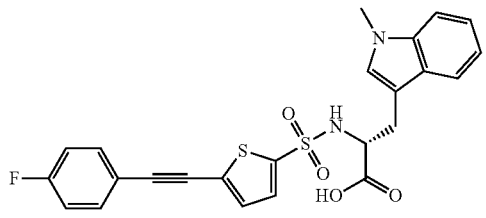 [SMILES: Cn1cc(C[C@@H](NS(=O)(=O)c2ccc(C#Cc3ccc(F)cc3)s2)C(=O)O)c2ccccc21] |
| 32 | 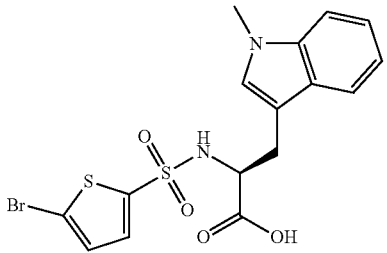 [SMILES: Cn1cc(C[C@H](NS(=O)(=O)c2ccc(Br)s2)C(=O)O)c2ccccc21] | 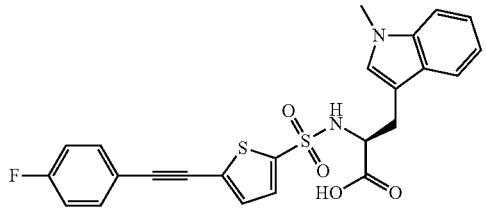 [SMILES: Cn1cc(C[C@H](NS(=O)(=O)c2ccc(C#Cc3ccc(F)cc3)s2)C(=O)O)c2ccccc21] |
| 33 | 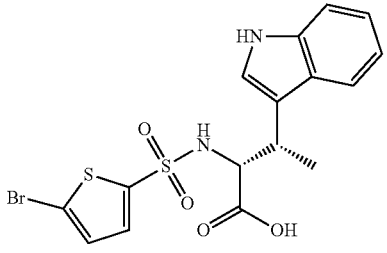 [SMILES: C[C@@H](c1c[nH]c2ccccc12)[C@@H](NS(=O)(=O)c1ccc(Br)s1)C(=O)O] | 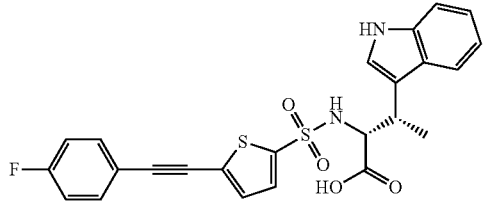 [SMILES: C[C@@H](c1c[nH]c2ccccc12)[C@@H](NS(=O)(=O)c1ccc(C#Cc2ccc(F)cc2)s1)C(=O)O] |
| 34 | 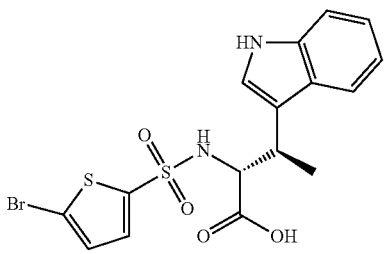 [SMILES: C[C@H](c1c[nH]c2ccccc12)[C@@H](NS(=O)(=O)c1ccc(Br)s1)C(=O)O] | 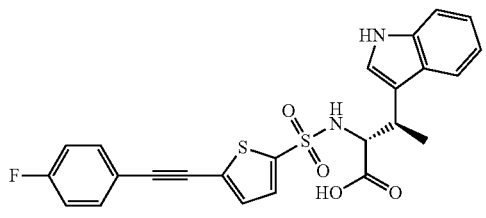 [SMILES: C[C@H](c1c[nH]c2ccccc12)[C@@H](NS(=O)(=O)c1ccc(C#Cc2ccc(F)cc2)s1)C(=O)O] |

TABLE 3-continued

| Ex.# | Sulphonamide | Phenylethynyl-thiophene Coupled Product |
|---|---|---|
| 35 | | |
| 36 | | |
| 37 | | |
| 38 | | |
| 39 | | |

TABLE 3-continued

| Ex.# | Sulphonamide | Phenylethynyl-thiophene Coupled Product |
|---|---|---|
| 40 | | |
| 41 | | |

Example 42-54

If one were to follow a similar procedure as that described in Example 2, except using the commercially available p-trifluoromethylphenylacetylene (Sigma Aldrich, cat. #556432) and the synthesized sulfonamides (Example 3-15, Table 1) indicated in Table 4 below, the following compounds could be prepared.

TABLE 4

| Ex. # | Sulphonamide | Phenylethynyl-thiophene Coupled Product |
|---|---|---|
| 42 | | |
| 43 | | |

TABLE 4-continued
| Ex. # | Sulphonamide | Phenylethynyl-thiophene Coupled Product |
|---|---|---|
| 44 | 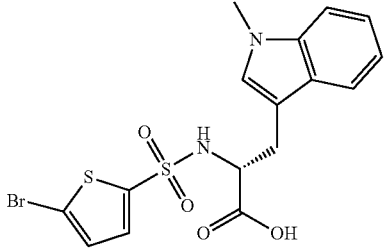 [SMILES: Cn1cc(C[C@@H](NS(=O)(=O)c2ccc(Br)s2)C(=O)O)c2ccccc21] | 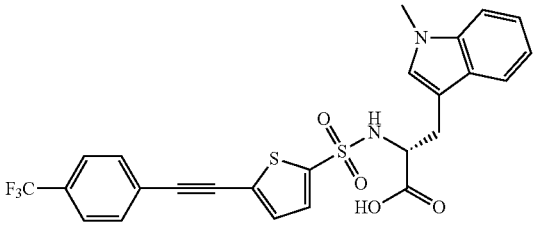 [SMILES: Cn1cc(C[C@@H](NS(=O)(=O)c2ccc(C#Cc3ccc(C(F)(F)F)cc3)s2)C(=O)O)c2ccccc21] |
| 45 | 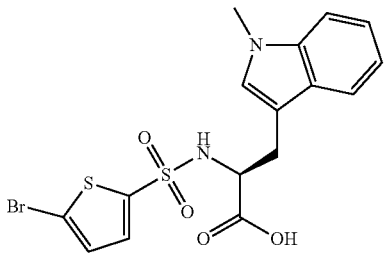 [SMILES: Cn1cc(C[C@H](NS(=O)(=O)c2ccc(Br)s2)C(=O)O)c2ccccc21] | 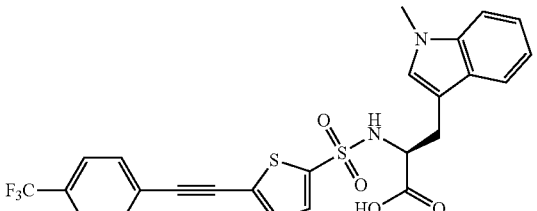 |
| 46 | 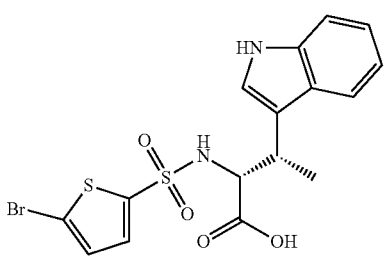 [SMILES: C[C@@H](c1c[nH]c2ccccc12)[C@@H](NS(=O)(=O)c1ccc(Br)s1)C(=O)O] | 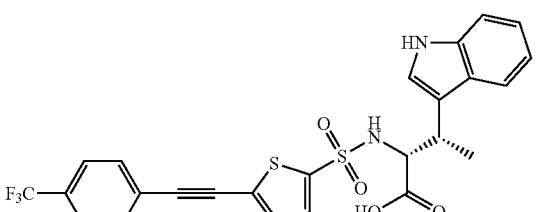 |
| 47 | 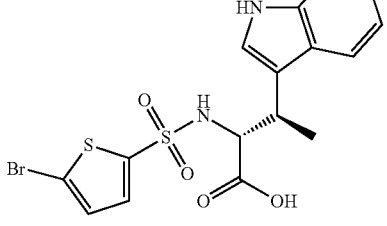 | 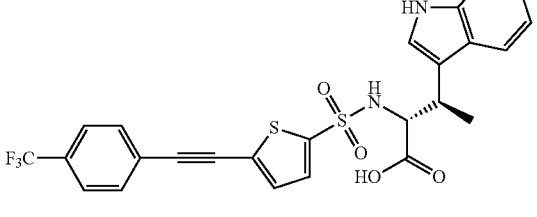 |
| 48 | 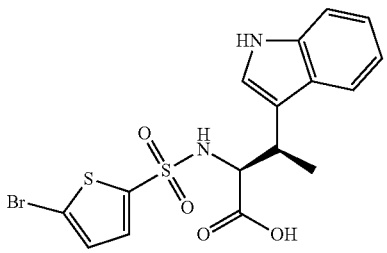 [SMILES: C[C@H](c1c[nH]c2ccccc12)[C@H](NS(=O)(=O)c1ccc(Br)s1)C(=O)O] | 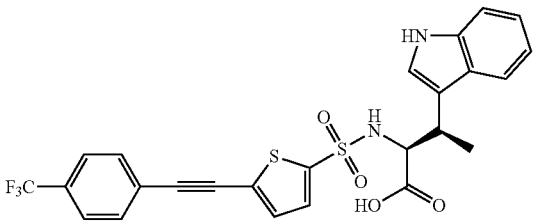 [SMILES: C[C@H](c1c[nH]c2ccccc12)[C@H](NS(=O)(=O)c1ccc(C#Cc2ccc(C(F)(F)F)cc2)s1)C(=O)O] |

TABLE 4-continued
| Ex. # | Sulphonamide | Phenylethynyl-thiophene Coupled Product |
|---|---|---|
| 49 | 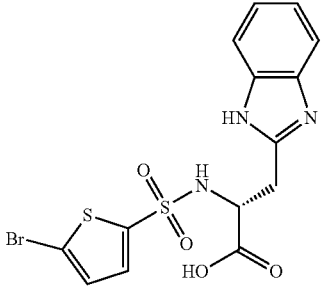 [SMILES: O=C(O)[C@@H](Cc1nc2ccccc2[nH]1)NS(=O)(=O)c1ccc(Br)s1] | 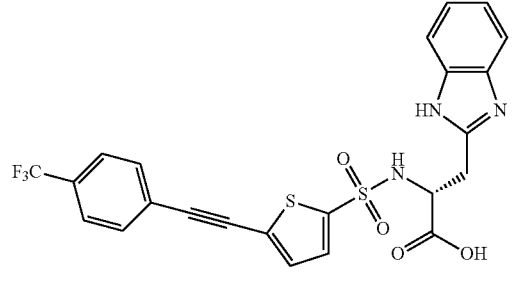 [SMILES: O=C(O)[C@@H](Cc1nc2ccccc2[nH]1)NS(=O)(=O)c1ccc(C#Cc2ccc(C(F)(F)F)cc2)s1] |
| 50 | 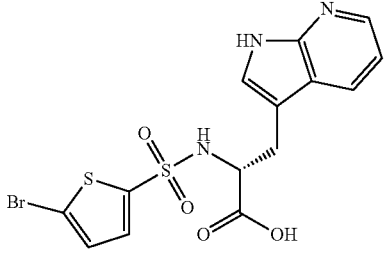 [SMILES: O=C(O)[C@@H](Cc1c[nH]c2ncccc12)NS(=O)(=O)c1ccc(Br)s1] | 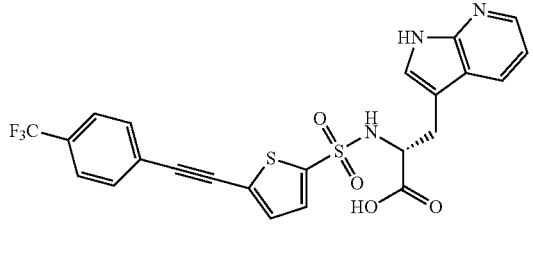 [SMILES: O=C(O)[C@@H](Cc1c[nH]c2ncccc12)NS(=O)(=O)c1ccc(C#Cc2ccc(C(F)(F)F)cc2)s1] |
| 51 | 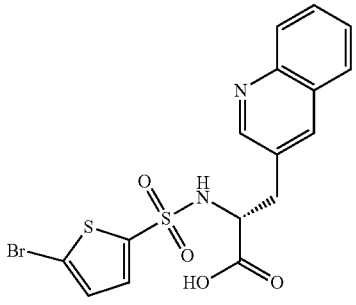 [SMILES: O=C(O)[C@@H](Cc1cnc2ccccc2c1)NS(=O)(=O)c1ccc(Br)s1] | 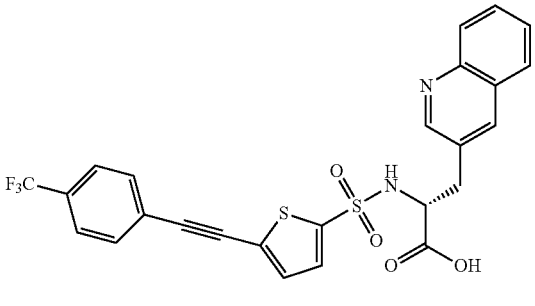 [SMILES: O=C(O)[C@@H](Cc1cnc2ccccc2c1)NS(=O)(=O)c1ccc(C#Cc2ccc(C(F)(F)F)cc2)s1] |
| 52 | 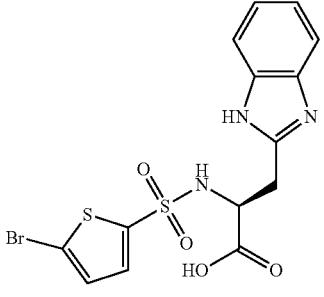 [SMILES: O=C(O)[C@H](Cc1nc2ccccc2[nH]1)NS(=O)(=O)c1ccc(Br)s1] | 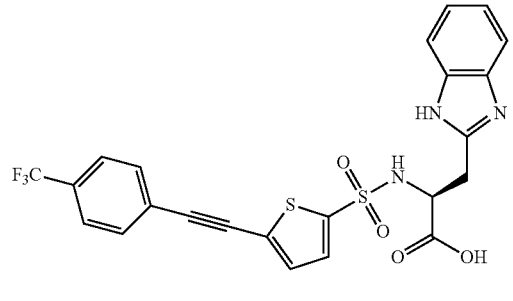 [SMILES: O=C(O)[C@H](Cc1nc2ccccc2[nH]1)NS(=O)(=O)c1ccc(C#Cc2ccc(C(F)(F)F)cc2)s1] |
| 53 | 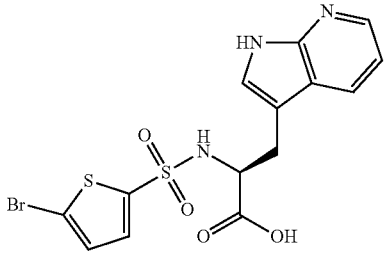 [SMILES: O=C(O)[C@H](Cc1c[nH]c2ncccc12)NS(=O)(=O)c1ccc(Br)s1] | 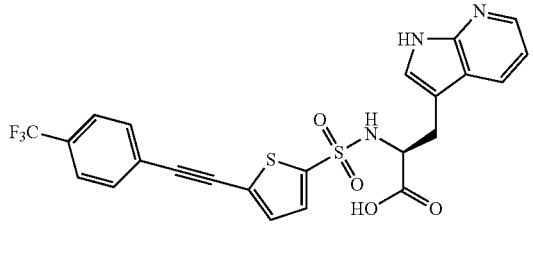 [SMILES: O=C(O)[C@H](Cc1c[nH]c2ncccc12)NS(=O)(=O)c1ccc(C#Cc2ccc(C(F)(F)F)cc2)s1] |

TABLE 4-continued

| Ex. # | Sulphonamide | Phenylethynyl-thiophene Coupled Product |
|---|---|---|
| 54 | | |

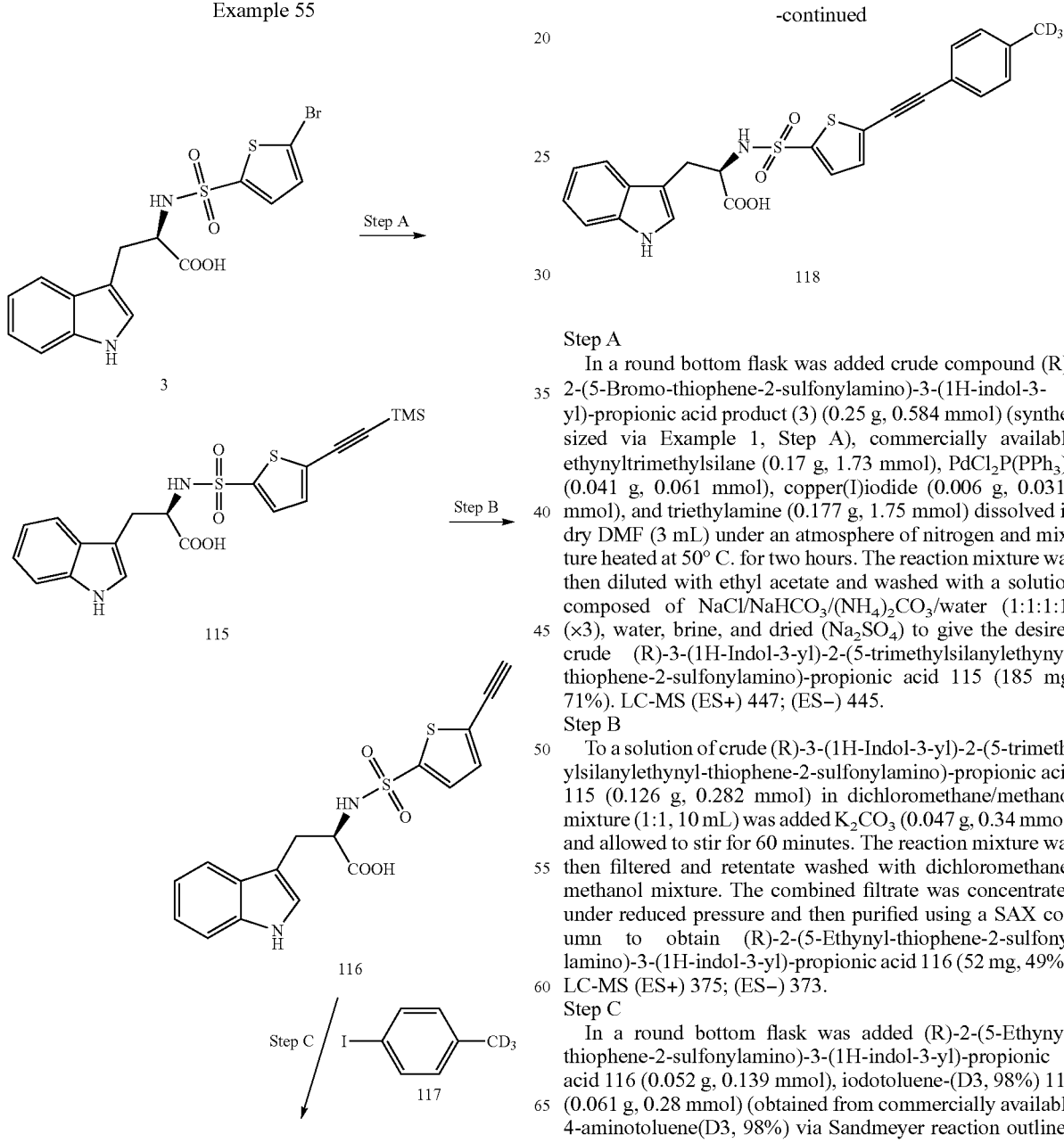

Example 55

Step A

In a round bottom flask was added crude compound (R)-2-(5-Bromo-thiophene-2-sulfonylamino)-3-(1H-indol-3-yl)-propionic acid product (3) (0.25 g, 0.584 mmol) (synthesized via Example 1, Step A), commercially available ethynyltrimethylsilane (0.17 g, 1.73 mmol), PdCl$_2$P(PPh$_3$)$_2$ (0.041 g, 0.061 mmol), copper(I)iodide (0.006 g, 0.0315 mmol), and triethylamine (0.177 g, 1.75 mmol) dissolved in dry DMF (3 mL) under an atmosphere of nitrogen and mixture heated at 50° C. for two hours. The reaction mixture was then diluted with ethyl acetate and washed with a solution composed of NaCl/NaHCO$_3$/(NH$_4$)$_2$CO$_3$/water (1:1:1:1) (×3), water, brine, and dried (Na$_2$SO$_4$) to give the desired crude (R)-3-(1H-Indol-3-yl)-2-(5-trimethylsilanylethynyl-thiophene-2-sulfonylamino)-propionic acid 115 (185 mg, 71%). LC-MS (ES+) 447; (ES−) 445.

Step B

To a solution of crude (R)-3-(1H-Indol-3-yl)-2-(5-trimethylsilanylethynyl-thiophene-2-sulfonylamino)-propionic acid 115 (0.126 g, 0.282 mmol) in dichloromethane/methanol mixture (1:1, 10 mL) was added K$_2$CO$_3$ (0.047 g, 0.34 mmol) and allowed to stir for 60 minutes. The reaction mixture was then filtered and retentate washed with dichloromethane-methanol mixture. The combined filtrate was concentrated under reduced pressure and then purified using a SAX column to obtain (R)-2-(5-Ethynyl-thiophene-2-sulfonylamino)-3-(1H-indol-3-yl)-propionic acid 116 (52 mg, 49%). LC-MS (ES+) 375; (ES−) 373.

Step C

In a round bottom flask was added (R)-2-(5-Ethynyl-thiophene-2-sulfonylamino)-3-(1H-indol-3-yl)-propionic acid 116 (0.052 g, 0.139 mmol), iodotoluene-(D3, 98%) 117 (0.061 g, 0.28 mmol) (obtained from commercially available 4-aminotoluene(D3, 98%) via Sandmeyer reaction outlined in Example 56), PdCl$_2$P[(PPh$_3$)]$_2$ (0.01 g, 0.015 mmol), copper(I)iodide (0.002 g, 0.0105 mmol) and triethylamine (0.025 g, 0.247 mmol) and dissolved in dry DMF (3 mL) under an atmosphere of nitrogen and mixture heated at 50° C. for 2 hours. The reaction mixture was cooled, diluted with ethyl acetate and washed with a solution composed of NaCl/NaHCO$_3$/(NH$_4$)$_2$CO$_3$/water (1:1:1:1) (×3), water, brine, and then dried over sodium sulfate (Na$_2$SO$_4$). The mixture was filtered and the filtrate was evaporated under reduced pressure to give crude 118 which was purified via SAX Column chromatography to give purified 118 (0.025 g, 38%). The product was further purified by preparative, reversed-phase-HPLC to obtain the desired product 118 (R)-3-(1H-Indol-3-yl)-2-[5-(4-trideuteromethyl-phenylethynyl)-thiophene-2-sulfonylamino]-propionic acid-(D3, 98%) in >95% purity by HPLC. LC-MS (ES+) 468; (ES−) 466;

$^1$H NMR (300 MHz, MeOH-d4) δ 3.17-3.25 (m), 4.32-4.35 (m), 5.60-5.66 (m), 7.05-7.68 (m), 10.4 (br s).

Example 56

Synthesis of 4-Iodotoluine (D3, 98%) Starting Material

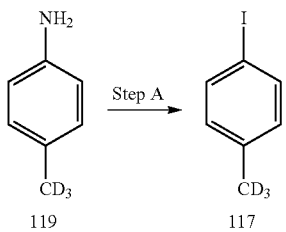 [SMILES: [2H]C([2H])([2H])c1ccc(N)cc1 ; [2H]C([2H])([2H])c1ccc(I)cc1]

119    117

Step A

Following the classic method of Griess (Practical Organic Chemistry, Richard Clay & Sons, page 144, Preparation #60, (1900)) in which 0.2 grams (1.8 mmoles) of toluidine (D3, 98%), commercially obtained from C/D/N Isotopes (Quebec, Canada) (119) is combined with 0.4 ml D$_2$SO$_4$ (obtained commercially from Cambridge Isotope Laboratories, Andover, Mass.) and the resulting mixture cooled until the temperature of the stirred mixture reaches 0° C. and then 160 mg (2.32 mmole) of sodium nitrite was slowly added in three portions over 10 minutes making sure that the temperature does not rise above 10° C. After the sodium nitrite has been added, a solution composed of 48 mg (2.9 mmole) of KI in 1 ml D$_2$O (obtained commercially from Cambridge Isotope Laboratories) was then added and the reaction mixture was allowed to warm to room temperature and stirred for 1 hour. The reaction mixture was then diluted with D$_2$O (10 mL) and extracted with ether (×2). The ether layer was then washed with 10% Na$_2$S$_2$O$_3$ in D$_2$O (×2) and dried over anhydrous sodium sulphate. The crude product (117) was then purified by column chromatography using hexane as the eluent to obtain the desired pure 4-Iodotoluene (D3, 98%) product (117) (0.16 g, 40%). $^1$H NMR (300 MHz, CDCl$_3$): δ, 6.93 (d, 2H, J=7.8 Hz), 7.56 (d, 2H, J=7.8 Hz).

When the D$_2$SO$_4$ was replaced by DCl (obtained commercially from Cambridge Isotope Laboratories, Andover, Mass.) only a 20% yield of 117 was obtained.

Example 57

Synthesis of 1-Ethynyl-4-methyl-benzene (D3, 98%)(Method 1)

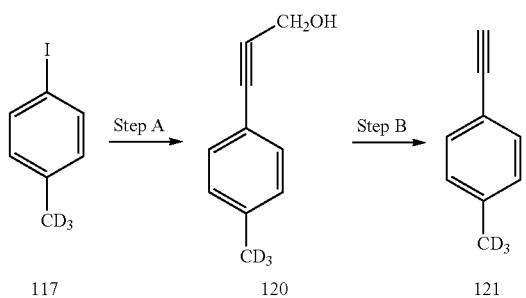

117    120    121

Step A

If one were to follow the method of Godt (Godt, A.; J. Org. Chem. 62(21), 7471-7472 and supplementary section), then if to a cooled (0° C.) and stirred mixture composed of 4-Iodotoluene(D3) (117) (obtained from Example 56), Pd(PPh3)$_2$C12 (2.2 mmole), CuI (3.5 mmole) in tetrahydrofuran (150 ml) and piperidine (70 ml) were to be added to commercially available Prop-2-yn-1-ol (252 mmole) over the course of 30 minutes under nitrogen one would obtain the crude acetylene coupled product (120). The crude product (120) could then be purified via column chromatography (ether-hexane) to give pure 3-p-Tolyl-prop-2-yn-1-ol (D3)(120)

Step B

If one were to continue to follow the method of Godt and added 535 mmoles of powdered KOH and 1.0 Moles of MnO2 to a stirred solution composed of the 3-p-Tolyl-prop-2-yn-1-ol (D3) (120) (109 mmole) in diethyl ether (500 ml) one would obtain after 5 hours the resulting crude 1-Ethynyl-4-methyl-benzene (D3) (121) which could be purified by distillation under reduced pressure to give the pure 1-Ethynyl-4-methyl-benzene (D3) product (121).

Example 58

Alternate synthesis of 1-Ethynyl-4-methyl-benzene (D3, 98%)(Method 2)

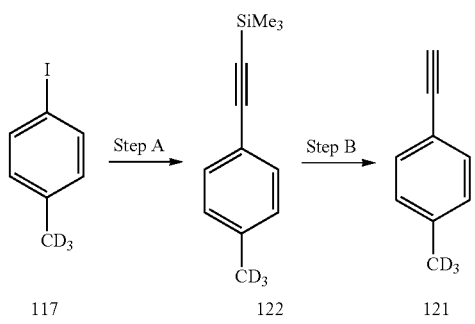 [SMILES: [2H]C([2H])([2H])c1ccc(I)cc1 ; [2H]C([2H])([2H])c1ccc(C#C[Si](C)(C)C)cc1 ; [2H]C([2H])([2H])c1ccc(C#C)cc1]

117    122    121

Step A

If one were to follow the method of Zhang and Coworkers (Zhang, W.; et al. Org. Synth. 84, 177-191, (2007)) then one could take 38 mmole of the Iodotoluene (D3)(117) product (obtained via Experiment 56) and add it to a round bottom flask containing CuI (0.77 mmole), Pd(PPH$_3$)$_2$Cl$_2$ (1.9 mmole) and place it under vacuum then nitrogen. To the solid can then be added tetrahydrofuran (90 ml) and piperidine (55 ml) and to the resulting mixture can be added in two portions over 5 minutes, commercially available 1-trimethylsilly-lacetylene (380 mmoles) and mixture allowed to stir under nitrogen for 24 hours which after filtering through a medium porosity fitted, glass funnel and concentrating the resulting solution one would then obtain the crude coupled acetylene product (122) which one can then purify via column chromatography to give pure acetylene coupled product (122).

Step B

Compound 122 from Step A above could then be treated with NaOD/D2O and Ethanol(D) (all obtained from Cambridge Isotope laboratories) to give the deprotected acetylene product (117) which could then be purified via column chromatography to give the resulting 1-Ethynyl-4-methyl-benzene (D3, 98%) (117) product.

Example 59

Synthesis of 1-Ethynyl-4-methyl-benzene (D7, 98%)

Example 60

Method 1, Synthesis of (R)-Tryptophan (2,3,5,6,7-D5)

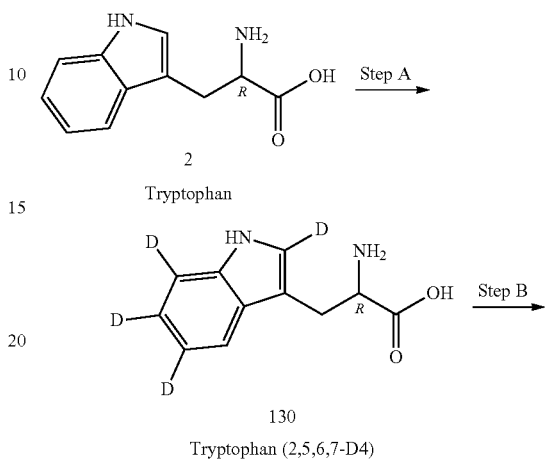

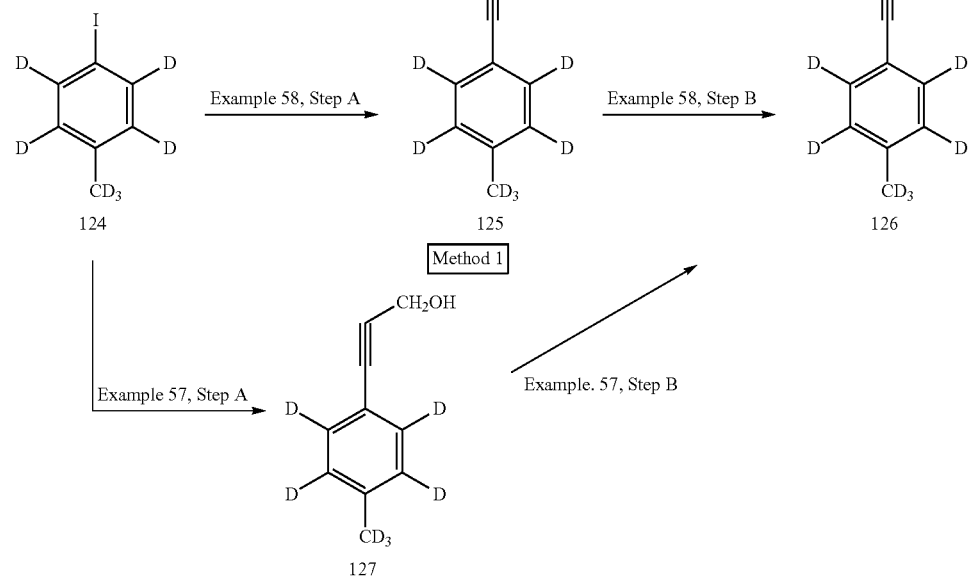

To make 1-Ethynyl-4-methyl-benzene (D7, 98%) 126 one could start with commercially available 4-iodotoluene (D7, 98%) (C/D/N/Isotopes, Inc. Quebec Canada, cat#D-6325) following Method 1 as represented in Example 57 or one could follow Method 2 as represented in Example 58 to produce after column purification 1-Ethynyl-4-methyl-benzene (D7, 98%) (126).

-continued

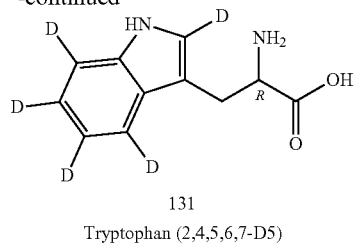

131
Tryptophan (2,4,5,6,7-D5)

To make the fully indole deuterated Tryptophan 131 one could follow the method of Wishart and Coworkers (Wishart, D. S.; et al. Biochemica et Biophysica Acta., 1164, 34-46, (1993) starting with 0.5 grams of reduced Adams catalyst (Pt°, made as per Wishart et al.) in a 250 ml round bottom flask containing 2.0 grams of Tryptophan (with alpha carbon having (R) chirality and obtained from Alfa-Aesar or Sigma Aldrich). To the mixture could then be added 30 ml of 99.9% $D_2O$ and then 1.2 ml of a 40% NaOD solution (both obtained from Cambridge Isotope Laboratories) and mixture refluxed under nitrogen and in the dark for 24 hours to obtain the crude partially deuterated Tryptophan (2,5,6,7-D4) (130) which could be isolated and purified at this step by the addition of HCl and worked up. If one requires the indole to be fully deuterated one could take the crude Tryptophan (2,5,6,7-D4) (130) product and add another 100 ml of $D_2O$ with 2.0 ml of 40% NaOD and reflux again for another 24 hours to isolate the resulting Tryptophan (2,4,5,6,7-D5) (131) product which could then be purified by recrystallization from water or alcohol after acidification with HCl.

Example 61

Method 1, Synthesis of (S)-Tryptophan (2,3,5,6,7-D5)

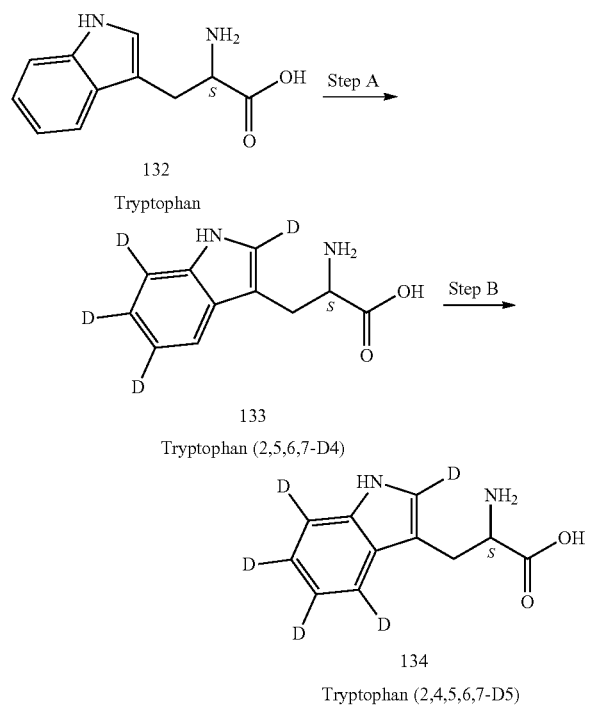

To make the fully indole deuterated Tryptophan have an S-chiral configuration one could follow the method as outlined in Experiment 60, Method 1 (Wishart, D. S.; et al. Biochemica et Biophysica Acta., 1164, 34-46, (1993)) starting with 0.5 grams of reduced Adams catalyst (Pt°, made as per Wishart et al.) in a 250 ml round bottom flask containing 2.0 grams of Tryptophan (with alpha carbon having (S) chirality and obtained from Sigma Aldrich or Alfa-Aesar) (132). To the mixture could then be added 30 ml of 99.9% $D_2O$ and then 1.2 ml of a 40% NaOD solution (both obtained from Cambridge Isotope Laboratories) and mixture refluxed under nitrogen and in the dark for 24 hours to obtain the crude partially deuterated Tryptophan (2,5,6,7-D4) (133) which could be isolated and purified at this step by the addition of HCl and worked up. If one requires the indole to be fully deuterated one could take the crude Tryptophan (2,5,6,7-D4) (133) product and add another 100 ml of $D_2O$ with 2.0 ml of 40% NaOD and reflux again for another 24 hours to isolate the resulting Tryptophan (2,4,5,6,7-D5) (134) product which could then be purified by recrystallization from water or alcohol after acidification with HCl.

Example 62

Method 2, Synthesis of (R)-Tryptophan (2,3,5,6,7-D5)

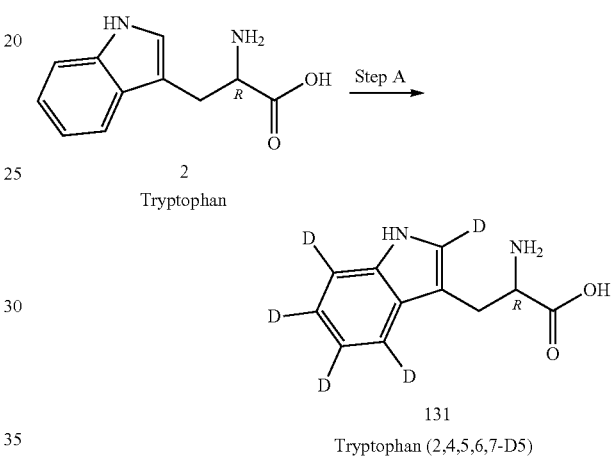

Another route for making the fully indole deuterated Tryptophan is via acid catalysis deuterium exchange reaction using Raney Nickel. Before using the Raney Nickel one must first remove the hydrogens this can be done by following the method of Pathak and co-workers (Pathak, et al. Tetrahedron Letters, 43(18), 4227-4234, (1987)). 100 ml (settled volume) of commercially obtained Raney Nickel (Sigma-Aldrich) can be washed (20×30 ml) with $D_2O$ (99.9%) (Cambridge Isotope Laboratories) making sure that the catalyst is allowed to stand in the water for at least 30 minutes between each washing. One could also include a wash with anhydrous Dioxane in the beginning to enhance the removal of the initial H2O. The method of Badenoch-Jones (Badenoch-Jones, J.; et al. Journal of Labeled Compounds and Radiopharmaceuticals-Vol. XX, No. 12, 1325-1330, (1983)) could then be used to perform the actual exchange of the Indole hydrogens. One could take 0.5 grams of (R)-Tryptophan (Sigma-Aldrich, Milwaukee, Wis. or from Alfa-Aesar) and dissolve it in 500 ml of $D_2O$ (Obtained from Cambridge Isotope laboratories, Andover, Mass.) and 100 ml of DCl (obtained from Cambridge Isotope Laboratories) and 50 ml (settled volume) of Raney Nickel and mixture heated at 100° C. with stirring for 10 days. The $D_2O$ can then be removed under reduced pressure and the procedure repeated once more to ensure maximum incorporation of deuterium. The product could then be purified by ion-exchange column chromatography or reversed phase HPLC to give purified (R)-tryptophan (D5) (131). This procedure can also be done on the (S)-tryptophan (132) to give the resulting (S)-tryptophan (D5) (134) compound.

Example 63

Synthesis of (R) and (S)-Tryptophan (D8)

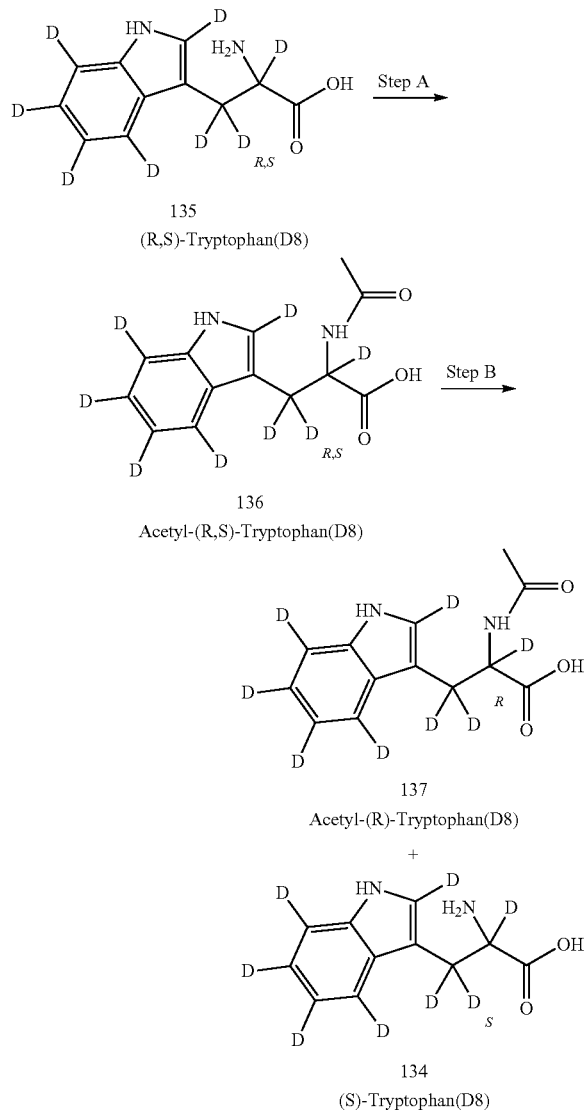

135
(R,S)-Tryptophan(D8)

Step A

136
Acetyl-(R,S)-Tryptophan(D8)

Step B

137
Acetyl-(R)-Tryptophan(D8)

+

134
(S)-Tryptophan(D8)

If one were interested in synthesizing the fully deuterated Tryptophan (D8) one could purchase commercially available racemic (R,S), deuterated Tryptophan (D8) (From C/D/N, Quebec, Canada, cat#D-1648) (135). One would then have to separate the two enantiomers. One could then follow the method of Bommarius and coworkers (Bommarius, A. S.; et al. Tetrahedron Asymmetry, 8(19), 3197-3200, (1997)) whereby one could take one gram of the deuterated racemic mixture (135) and place into a 100 ml round bottom flask containing 25 ml of dimethylformamide and then one could add 1.2 equivalents of acetic anhydride and 1.5 equivalents of pyridine stir the mixture overnight. After removing the volatile components of the reaction mixture under reduce pressure would could then purify the resulting acetylated Tryptophan (D8) mixture by column chromatography. One could then take the Acetylated Tryptophan racemic mixture (136) and enzymatically hydrolyze the Acetylated (S)-Tryptophan selectively using the Acylase *Aspergillus oryzae* (purchased from Amano Enzymes, Inc. and using their provided protocols) at a concentration of 30 g/l and using a solution of 0.3M acetylated racemic mixture (136) at pH=7, temp. 37° C. to give deacetylated (S)-Tryptophan (D8) (134). The Acetylated (R)-Tryptophan (D8) (137) could then be either hydrolyzed chemically or enzymatically (i.e. via a Lipase) to give the resulting free amine.

Example 70-77

Following a similar procedure as that described in Example 1, except using the deuterated Tryptophans from Exp. 60-63 (and/or commercially available Tryptophan derivatives obtained from Cambridge Isotope Laboratories, C/D/N and Sigma-Aldrich) indicated in Table 5 below and bromosulfonyl chloride 1, the following compounds could be prepared.

TABLE 5

| Ex. # | Amino Acid | Sulphonamide Product |
|---|---|---|
| 70 | | |

TABLE 5-continued

| Ex. # | Amino Acid | Sulphonamide Product |
|---|---|---|
| 71 | Tryptophan with indole ring deuterated at 2,4,5,6,7 positions (D5-Trp) | 5-Bromothiophene-2-sulfonamide of D5-Trp |
| 72 | D5-Trp additionally deuterated at both β-CH2 positions (β,β-D2) | 5-Bromothiophene-2-sulfonamide of the same D7-Trp |
| 73 | D5-Trp additionally deuterated at α-CH and both β-CH2 positions | 5-Bromothiophene-2-sulfonamide of the same D8-Trp |
| 74 | Trp deuterated at indole 2,4,5,7 positions (H at 6) | 5-Bromothiophene-2-sulfonamide of the same Trp |
| 75 | Trp deuterated at indole 2,4,6,7 positions (H at 5) | 5-Bromothiophene-2-sulfonamide of the same Trp |

TABLE 5-continued

| Ex. # | Amino Acid | Sulphonamide Product |
|---|---|---|
| 76 | (deuterated tryptophan, D at 5,6-positions of indole) | (5-bromothiophene-2-sulfonamide of deuterated tryptophan, D at 5,6-positions) |
| 77 | (deuterated tryptophan, D at 2,5,6-positions of indole) | (5-bromothiophene-2-sulfonamide of deuterated tryptophan, D at 2,5,6-positions) |

Example 78-91

Following a similar procedure, as that described in Example 2, except using the previously prepared p-tolylacetylenes (Example 57-59) and the synthesized sulfonamides (Example 1 and Examples 70-77, Table 1) indicated in Table 6 below, the following compounds could be prepared. (Example 78 is an alternative route to the synthesis of compound 118 which was synthesized via the route in Example 55).

TABLE 6

| Ex. # | Sulphonamide | Phenylethynyl-thiophene Coupled Product |
|---|---|---|
| 78 | (5-bromothiophene-2-sulfonamide of tryptophan) | (D$_3$C-phenyl-ethynyl-thiophene-2-sulfonamide of tryptophan) 118 |
| 79 | (5-bromothiophene-2-sulfonamide of tryptophan) | (D$_3$C-phenyl-ethynyl-thiophene-2-sulfonamide of tryptophan) |

TABLE 6-continued
| Ex. # | Sulphonamide | Phenylethynyl-thiophene Coupled Product |
|---|---|---|
| 80 | 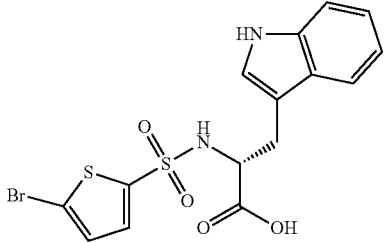 [SMILES: O=C(O)[C@@H](Cc1c[nH]c2ccccc12)NS(=O)(=O)c1ccc(Br)s1] | 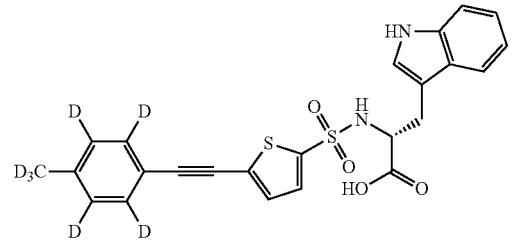 [SMILES: [2H]c1c([2H])c(C([2H])([2H])[2H])c([2H])c([2H])c1C#Cc1ccc(S(=O)(=O)N[C@H](Cc2c[nH]c3ccccc23)C(=O)O)s1] |
| 81 | 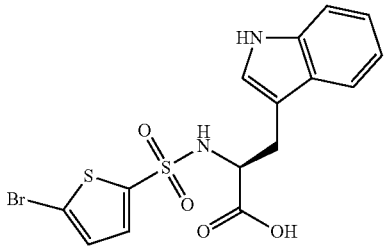 [SMILES: O=C(O)[C@H](Cc1c[nH]c2ccccc12)NS(=O)(=O)c1ccc(Br)s1] | 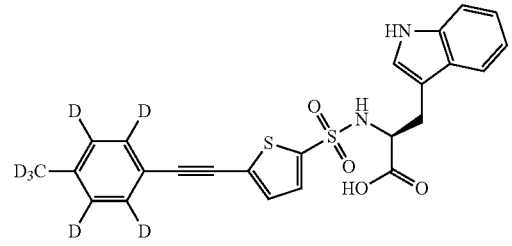 [SMILES: [2H]c1c([2H])c(C([2H])([2H])[2H])c([2H])c([2H])c1C#Cc1ccc(S(=O)(=O)N[C@@H](Cc2c[nH]c3ccccc23)C(=O)O)s1] |
| 82 | 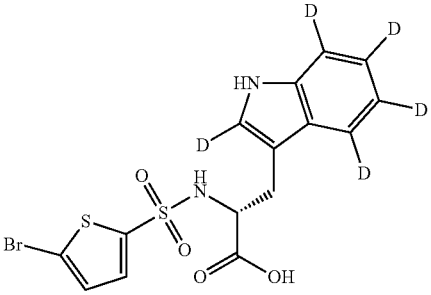 [SMILES: [2H]c1[nH]c2c([2H])c([2H])c([2H])c([2H])c2c1C[C@@H](NS(=O)(=O)c1ccc(Br)s1)C(=O)O] | 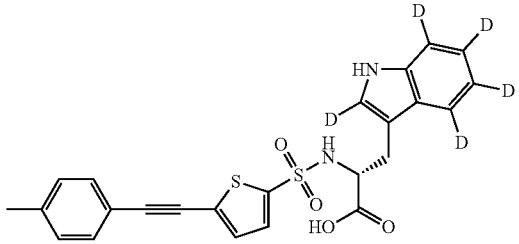 [SMILES: [2H]c1[nH]c2c([2H])c([2H])c([2H])c([2H])c2c1C[C@@H](NS(=O)(=O)c1ccc(C#Cc2ccc(C)cc2)s1)C(=O)O] |
| 83 | 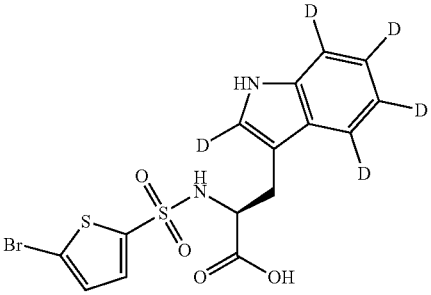 [SMILES: [2H]c1[nH]c2c([2H])c([2H])c([2H])c([2H])c2c1C[C@H](NS(=O)(=O)c1ccc(Br)s1)C(=O)O] | 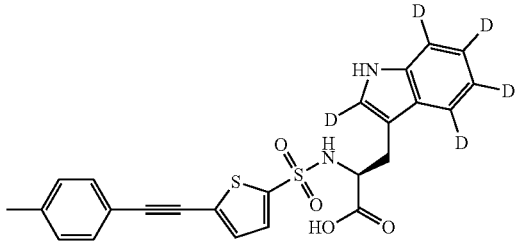 [SMILES: [2H]c1[nH]c2c([2H])c([2H])c([2H])c([2H])c2c1C[C@H](NS(=O)(=O)c1ccc(C#Cc2ccc(C)cc2)s1)C(=O)O] |
| 84 | 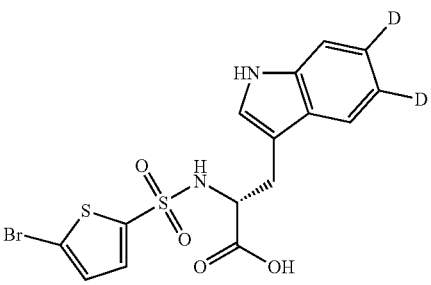 [SMILES: [2H]c1cc2[nH]cc(C[C@@H](NS(=O)(=O)c3ccc(Br)s3)C(=O)O)c2cc1[2H]] | 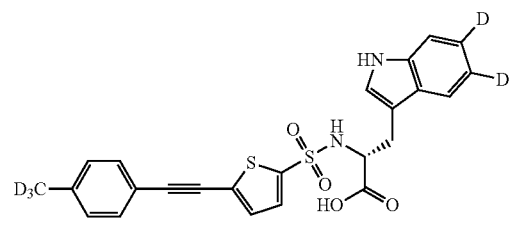 [SMILES: [2H]c1cc2[nH]cc(C[C@@H](NS(=O)(=O)c3ccc(C#Cc4ccc(C([2H])([2H])[2H])cc4)s3)C(=O)O)c2cc1[2H]] |

TABLE 6-continued
| Ex. # | Sulphonamide | Phenylethynyl-thiophene Coupled Product |
|---|---|---|
| 85 | 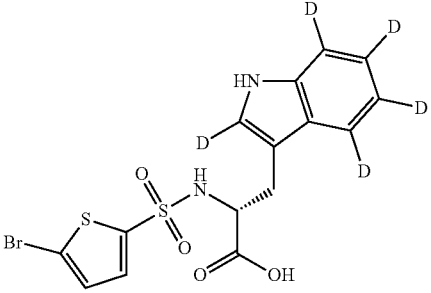 [SMILES: [2H]c1[nH]c2c([2H])c([2H])c([2H])c([2H])c2c1C[C@@H](NS(=O)(=O)c1ccc(Br)s1)C(=O)O] | 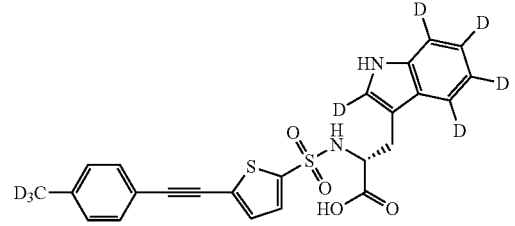 [SMILES: [2H]c1[nH]c2c([2H])c([2H])c([2H])c([2H])c2c1C[C@@H](NS(=O)(=O)c1ccc(C#Cc2ccc(C([2H])([2H])[2H])cc2)s1)C(=O)O] |
| 86 | 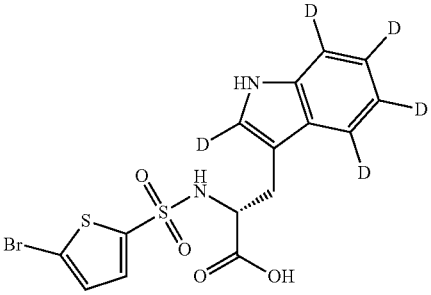 [SMILES: [2H]c1[nH]c2c([2H])c([2H])c([2H])c([2H])c2c1C[C@@H](NS(=O)(=O)c1ccc(Br)s1)C(=O)O] | 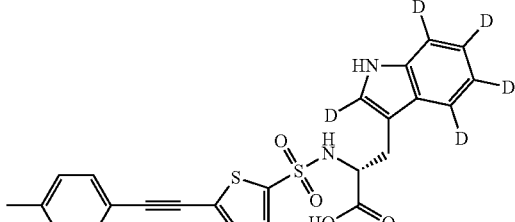 |
| 87 | 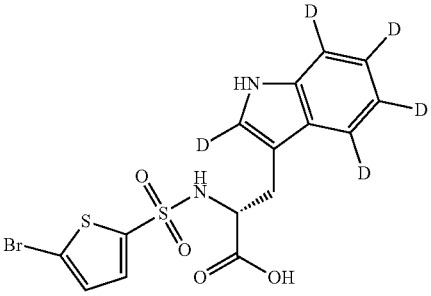 [SMILES: [2H]c1[nH]c2c([2H])c([2H])c([2H])c([2H])c2c1C[C@@H](NS(=O)(=O)c1ccc(Br)s1)C(=O)O] | 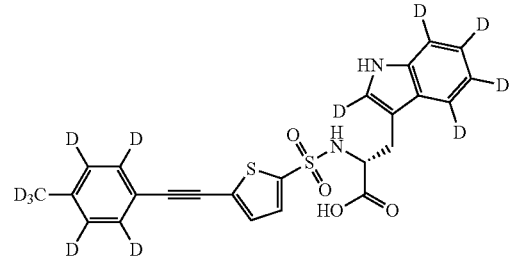 [SMILES: [2H]c1[nH]c2c([2H])c([2H])c([2H])c([2H])c2c1C[C@@H](NS(=O)(=O)c1ccc(C#Cc2c([2H])c([2H])c(C([2H])([2H])[2H])c([2H])c2[2H])s1)C(=O)O] |
| 88 | 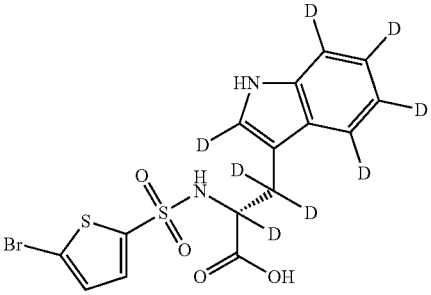 [SMILES: [2H]c1[nH]c2c([2H])c([2H])c([2H])c([2H])c2c1C([2H])([2H])[C@@]([2H])(NS(=O)(=O)c1ccc(Br)s1)C(=O)O] | 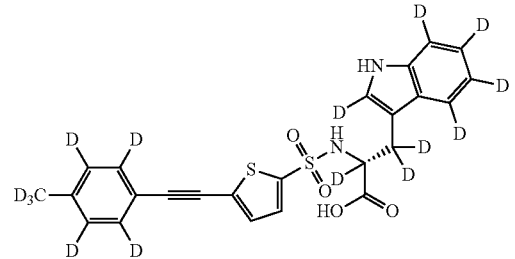 [SMILES: [2H]c1[nH]c2c([2H])c([2H])c([2H])c([2H])c2c1C([2H])([2H])[C@]([2H])(NS(=O)(=O)c1ccc(C#Cc2c([2H])c([2H])c(C([2H])([2H])[2H])c([2H])c2[2H])s1)C(=O)O] |
| 89 | 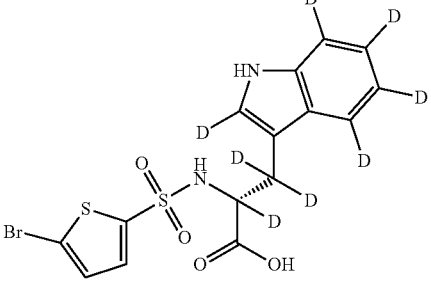 | 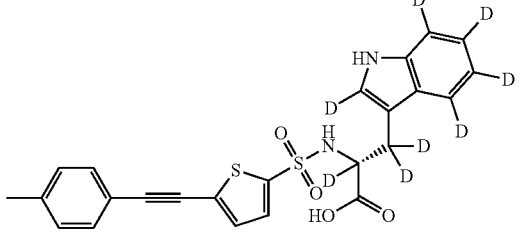 |

TABLE 6-continued

| Ex. # | Sulphonamide | Phenylethynyl-thiophene Coupled Product |
|---|---|---|
| 90 | (structure: 5-bromothiophene-2-sulfonyl-D4-tryptophan) | (structure: 4-methylphenylethynyl-thiophene-2-sulfonyl-D4-tryptophan) |
| 91 | (structure: 5-bromothiophene-2-sulfonyl-D4-tryptophan) | (structure: D3C-phenylethynyl-thiophene-2-sulfonyl-D4-tryptophan) |

Example 105

In-Vitro Assay for Determining Microsomal Stability of Select Compounds in Human and Mouse Microsomes Human and mouse microsomal stability was determined for select compounds following the method of Houston (Houston, J. B; Biochem. Pharmacol. 47, (1994),1469).

1 µM concentration of compound and separate human and mouse microsomes (0.3 mg/mL, BD bioscience) were used in the in-vitro assay. To ensure proper energy supply for microsomal degradation of compound, an energy regenerating system comprised of 100 mM potassium phosphate, 2 mM NADPH, 3 mM $MgCl_2$, pH=7.4. and the microsomal protein is added to each sample and the resulting suspension is then incubated in duplicate for 60 min at 37° C. in a rotary shaker. A control is run for each test agent in duplicate omitting NADPH to detect NADPH-free degradation. At T=0 and T=60 min., an aliquot is removed from each experimental and control reaction and then mixed with an equal volume of ice-cold Stop Solution (consisting of 0.3% acetic acid in acetonitrile containing haloperidol and diclofenac as internal standards). Stopped reactions are then incubated for at least ten minutes at −20° C., and an additional volume of water is then added. The samples are then centrifuged to remove precipitated protein, and the supernatants are then analyzed by LC-MS/MS to determine the percentage of compound remaining. The LC-MS/MS system used was an Agilent 6410 mass spectrometer coupled with an Agilent 1200 HPLC and a CTC PAL chilled autosampler, all controlled by MassHunter software (Agilent), or an ABI2000 mass spectrometer coupled with an Agilent 1100 HPLC and a CTC PAL chilled autosampler, all controlled by Analyst software (ABI). After separation on a C18 reverse phase HPLC column (Agilent, Waters, or equivalent) using an acetonitrile-water gradient system, peaks were analyzed by mass spectrometry (MS) using ESI ionization in MRM mode.

Table 7 and 8 below show the microsomal stability of select compounds in both human and mouse microsomes.

TABLE 7

In-vitro Human Microsomal Stability Of Select Compounds

| Compound ID # | Compound Concentration (microMoles) | Test Species | Mean Remaining Parent with NADPH (%)[1] | Mean Remaining Parent without NADPH (%)[1] |
|---|---|---|---|---|
| 5 | 1 | Human | 86 | 89 |
| 118 | 1 | Human | 88 | 97 |

[1] at T = 60 minutes

TABLE 8

In-vitro Mouse Microsomal Stability Of Select Compounds

| Compound ID # | Compound Concentration (microMoles) | Test Species | % Mean Remaining Parent with NADPH (%)[1] | % Mean Remaining Parent without NADPH (%)[1] |
|---|---|---|---|---|
| 5 | 1 | Mouse | 83 | 88 |
| 118 | 1 | Mouse | 85 | 91 |

[1] at T = 60 minutes

Measuring Neuropathic Pain Inhibition-(SNL)-Mouse Animal Model:.

Background and Description of the Animal Model

To measure the neuropathic pain inhibiting affects of the MMP inhibitors of the present invention, the spinal nerve ligation (SNL) mouse model was run on a select number of compounds. This model which began with the work of Bennet and coworkers (Bennet, G. J. et al. Pain, 33, (1988), 87-107) and was optimized by Kim and Chung (Kim, S. H.; Chung, J.

M. Pain, 50, (1992), 355-363) entails first, under magnification, the removal of one-third of the transverse process and then identifying and then dissecting free the L5 spinal nerve from the adjacent L4 spinal nerve in the mouse. The L5 spinal nerve is then tightly ligated using 6.0 silk suture. The nerve injury leads to hyperalgesia which manifests itself by enhanced responses to mechanical, heat and/or cooling stimuli. In this case, mechanical hyperalgesia is tested via Von Frey monofilaments in which filaments of varying thicknesses and bending force are individually applied to the plantar surface of the foot of the mouse. The threshold force necessary for paw withdrawal decreases dramatically after the nerve surgery. Potent pain inhibitors will reverse this affect resulting in greater force needing to be applied to cause the rodent paw to withdrawal.

Example 110

Intrathecal (i.t.) Administration of MMP Inhibitors in the (SNL)-Mouse Model of Pain Following preoperative baseline (Day −2) paw threshold measurement, FVB male mice were subjected to SNL injury (Day −1). The next day (Day 0) after SNL surgery, the animals were tested for post-operative baseline threshold measurements for mechanical allodynia; and the animals were then randomly assigned to one of 3 treatment groups (see Table 9). Over the course of the study, paw withdrawal threshold of these animals was measured in response to mechanical stimulation using the von Frey Monofilament Test.

To avoid systemic effects of the MMP inhibitors, the MMP inhibitors of the present invention were delivered into the cerebral spinal fluid (CSF) space around lumbosacral spinal cord via intrathecal (i.t.) administration, with the idea of targeting MMPs in the DRG, spinal cord, and spinal CSF. Intrathecal MMP inhibitor administration could then target not only spinal cord cells but also DRG cells. Each intrathecal (i.t.) injection was carried out according to the technique of Hylden and Wilcox (Hylden J L, Wilcox G L. Eur. J. Pharmacol., 67, (1980), 313-6) 5.2 mg of each of the MMP inhibitors were first dissolved in 140 microliters of DMSO and then put into 1260 microliters of 0.5% hydroxypropyl cellulose (HPC) in water to make a fine suspension composed of compound in 10% DMSO-0.5% hydroxypropyl cellulose. 10 microliters of the mixture was injected into the intrathecal space of male FVB mice (weighing 22-25 grams each and obtained from the Jackson Laboratories, Bar Harbor, Me.), by lumbar puncture in a volume of 10 μl/mouse using a Hamilton microsyringe via a 30 gauge needle inserted between lumbar vertebrae 5 and 6. In brief, each animal was held firmly by the pelvic girdle in one hand, while the needle was inserted into the tissue on the right side of the L5 or L6 spinous process. The needle was moved forward and slipped into the groove between the spinous process and transverse process and gently moved forward to the intervertebral space at ~10° angle. As the needle was inserted (~0.5 cm) within the vertebral column a tail flick was evident, and the solution was then injected. Table 9 summarizes the various treatment groups and frequency of administration.

TABLE 9

Animal i.t. Treatment Groups & Compounds Tested

| Treatment | # of Mice | Dose | Route of Administration And Frequency |
| --- | --- | --- | --- |
| Vehicle | 8 | Group 1, 10 μl/mouse | i.t, daily injections, from day 1-6, starting day 1 |
| Compound # 5 | 4 | Group 2, 10 μl/mouse | i.t, daily injections, from day 1-6, starting day 1 |
| Compound # 118 | 5 | Group 3, 10 μl/mouse | i.t, daily injections, from day 1-6, starting day 1 |

*Vehicle = 10% DMSO, 0.5% hydroxypropyl cellulose in water

Tactile Allodynia Test. Mechanical allodynia was measured using the calibrated von Frey filaments (Semmes-Weinstein monofilaments; Stoelting, Wood Dale, Ill., U.S.A.). The plantar surface of the left injured paw of each animal was tested as described by Chaplan et al. (Journal of Neuroscience Methods, 53, (1994), 55-63). The Fifty percent paw withdrawal threshold response was determined by sequentially increasing or decreasing the stimulus strength according to the "up-down method" of Dixon (Annual Review Pharmacology Toxicology, 20, (1980), 441-462). For mice, eight von Frey filaments were used, with approximately equal logarithmic incremental bending forces (von Frey number: 1.65, 2.36, 2.44, 2.83, 3.22, 3.61, 3.84, 4.08, and 4.17; equivalent to 0.005, 0.02, 0.03, 0.07, 0.17, 0.41, 0.69, 1.20, and 1.48 g force, respectively).

Prior to testing, each animal was placed in a suspended clear plastic chamber with a wire mesh bottom and acclimated for 15 minutes. Testing was initiated with the 0.07 g (handle marking of 2.83) applied perpendicularly to the plantar surface of the affected hind paw; each filament was applied with enough pressure to cause a buckle effect. The absence of a paw lifting/withdrawal response after 6 s prompted the use of the next higher weight filament. Paw withdrawal, indicating a positive response, prompted the use of a weaker filament. After the initial positive response (i.e., paw withdrawal), the testing continued for four additional measurements, and was used to calculate the response threshold. Four consecutive positive responses received a score of 0.001 g, and five consecutive negative responses (i.e., no paw withdrawal) received a score of 1.5 g.

Analyses for Tactile Allodynia Testing. The 50% paw withdrawal threshold was calculated (PWT; Luo and Calcutt, J. Pharmacology Experimental Therapeutics, 303(3), (2002), 1199-1205; Chaplan et al. Journal of Neuroscience Methods, 53, (1994), 55-63) using the formula:

$$10^{(Xf+\kappa\delta)}/10,000$$

where Xf is the final von Frey filament used (log units), κ is a value that analyzes the response pattern (taken from the table published by Chaplan et al., 1994), and δ is the mean difference between stimuli (log units).

Control of Bias. To prevent bias in the results of the study, the technical staff was not aware of the treatment history of each animal while evaluating the behavioral responses of the animals.

The results of the behavior testing which is presented in Table 10 clearly show the almost complete reversal of allodynia by compound #118 as compared to vehicle and compound #5. This is more easily seen in FIG. 1 which shows a plot of the days of injection/von Frey testing (time) versus the Paw Withdrawal Threshold (g) for each of the treatment groups.

TABLE 10

(i.t.)-SNL-Mouse Behavioral Testing Results For Vehicle, Compounds #5 and #118 (units in grams).

| | Day(-2) Pre-operative Baseline [1] | Day 0 Postoperative Baseline [2] | Day 1 [3] | Day 5 | Day 7 |
|---|---|---|---|---|---|
| Group 1: Vehicle | | | | | |
| Mean | 1.130 | 0.068 | 0.110 | 0.026 | 0.071 |
| Std. Dev. | 0.418 | 0.112 | 0.102 | 0.025 | 0.056 |
| Group 2: Compound #5 | | | | | |
| Mean | 1.265 | 0.050 | 0.098 | 0.079 | 0.190 |
| Std. Dev. | 0.271 | 0.048 | 0.100 | 0.055 | 0.230 |
| Group 3: Compound #118 | | | | | |
| Mean | 1.268 | 0.077 | 0.321 | 0.320 | 1.024 |
| Std. Dev. | 0.327 | 0.072 | 0.660 | 0.297 | 0.521 |

[1] Testing prior to SNL injury (pre-operative baseline)
[2] Testing 2 days after SNL injury (post operative injury baseline)
[3] Testing conducted 2 hr after first i.t. injection.

Example 111

Intraperitoneal (i.p.) Administration of MMP Inhibitors in the (SNL)-Mouse Model of Pain In order to better ascertain the bioavailability of the MMP compounds of the present invention when compound is administered outside of the spinal cord area, the SNL-mouse model was repeated with compounds #5 and #118 via intraperitoneal administration. Except for the mode of administration, number of mice/group and the number of injections and amount of compound per injection, the rest of the study was done in the same manner (in regards to the surgeries and tactile allodynia testing and analysis) as Experiment 110. 3.2 mg of each of the MMP inhibitors #5 and #118 were dissolved in 320 microliters of DMSO. To the solution was then added 32 microliters of Tween 80, followed by 2850 microliters of phosphate buffered saline (PBS). This gave a final concentration of 10% DMSO, 1% Tween and 1 mg/ml compound. 0.1 ml of this solution was then injected per mouse/day (for five consecutive days) to give an approximate dose of 3.3 mg/Kg. The treatment groups are outlined in Table 11. The results of the behavior tests can be seen in Table 12. It is clear that compound #118 shows a complete reversal of mechanical alodynia by day 5. FIG. 2 shows a plot of the days of injection/von Frey testing (time) versus the Paw Withdrawal Threshold (g) for each of the treatment groups. It is interesting to point out the rather prolonged affect exerted by compound #118 even after 48 hours (day 6) from the last injection (day 4).

TABLE 11

Animal IP Treatment Groups

| Treatment | # of mice | Dose | Route of Administration And Frequency |
|---|---|---|---|
| Vehicle | 3 | Group 1, 100 μl/mouse | IP daily injections day 1-5 |
| Compound # 5 | 3 | Group 2, 100 μl/mouse | IP daily injections day 1-5, starting day 1 |
| Compound #118 | 3 | Group 3, 100 μl/mouse | IP daily injections day 1-5, starting day 1 |

*Vehicle = 10% DMSO, 1% Tween 80, in PBS.

TABLE 12

(i.p.)-SNL-Mouse Behavioral Testing Results For Vehicle, Compounds #5 and #118 (units in grams).

| | Day 0 Postoperative Baseline | Day 1 | Day 2 | Day 5 | Day 6 | Day 7 |
|---|---|---|---|---|---|---|
| Group 1: Vehicle | | | | | | |
| Mean | 0.112 | 0.167 | 0.137 | 0.130 | 0.065 | 0.056 |
| Std.Dev. | 0.078 | 0.098 | 0.142 | 0.056 | 0.048 | 0.019 |
| Group 2: Compound #5 | | | | | | |
| Mean | 0.046 | 0.078 | 0.117 | 0.238 | 0.099 | 0.128 |
| Std.Dev. | 0.065 | 0.046 | 0.127 | 0.246 | 0.113 | 0.098 |
| Group 3: Compound #118 | | | | | | |
| Mean | 0.096 | 0.170 | 0.350 | 1.470 | 0.867 | 0.250 |
| Std.Dev. | 0.059 | 0.192 | 0.226 | 0.052 | 0.553 | 0.118 |

Example 120

Measuring Inflammatory Pain Inhibition-carrageena (CARR)-induced Inflammation in Rats If one were to measure the inflammatory pain inhibiting affects of the MMP inhibitors of the present invention, one could use the Carrageenan model for measuring neuropathic pain as presented in LaBuda, C. J., and Fuchs, P. N. Neuroscience Letters, 304, (2001), 137-140.

Acute Model: Subcutaneous injection into the hindpaw of a rat: An acute inflammatory condition is produced by a subcutaneous injection of 3% lambda Carrageenan (0.12 ml) into the plantar surface of one hindpaw under light isoflurane anesthesia. Usually, there is an additional control group that receives an equal volume of saline. Animals would then receive the MMP inhibitors of the present invention 3½ hours after the CARR injection, Quantification of pain behavior could then be performed via the paw withdrawal animal model using the same procedures as outlined in Experiment 110 & 111.

Chronic Model: Intra-articular injection. A longer lasting state of inflammation is produced by performing intra-articular injection of CARR (0.1 ml, 3%) into the tibial joint under isoflurane anesthesia. This route of administration induces an inflammatory condition that can last for up to 7 days following injection and is an established model of arthritic inflammatory pain. Quantification of pain behavior could then be performed using the same procedures as outlined in Experiments 110 & 111.

Example 130

Assay for Determining MMP-2 Inhibition

MMP-2 inhibitor activity was carried out via the method of Knight (Knight, C. G. et. al, *FEBS LETT.* 296 (3), (1992), 263-266), using an assay buffer comprised of 50 mM Tris-HCl, pH 7.6, 200 mM NaCl, 5 mM $CaCl_2$ and 1 μM $ZnSO_4$. A concentration of MMP inhibitor of the present invention was tested (1 microMolar) in duplicate runs. Catalytic domain of MMP-2 (human recombinant) enzyme (10 nanoMolar) was added to the compound solution. The mixture of enzyme and compound in assay buffer was then thoroughly mixed and incubated for 60 minutes at 37° C. Upon the completion of incubation, the assay was then started by the addition of 10 μM of fluorescent substrate Mca-P-L-G-L-Dpa-A-R-NH2 (Kd ~8 microMolar). The fluorescent product, McaPLG, was then measured at excitation of 355 nm and emission 405 nm by an automatic plate multireader at 37° C. A positive control was separately run using the broad spectrum MMP inhibitor GM6001 as a control compound (MMP-2 IC50=0.5 nanoMolar). Table 13 summarizes the results of the inhibition study.

TABLE 13

Percent MMP-2 Inhibition

| Compound ID# | Compound Concentration | Substrate | Substrate Concentration | Average Percent Inhibition |
|---|---|---|---|---|
| 5 | 1 microMolar | Mca-P-L-G-L-Dpa-A-R-NH2 | 10 microMolar | 97% |
| 118 | 1 microMolar | Mca-P-L-G-L-Dpa-A-R-NH2 | 10 microMolar | 96% |

Example 131

Assay for Determining MMP-9 Inhibition

MMP-9 inhibitor activity was carried out via the method of Bickett, D. M.; (Bickett, D. M., et al *Analytical Biochemistry* 212, (1993), 58-64), using an assay buffer comprised of 50 mM Tris-HCl, pH 7.6, 200 mM NaCl, 5 mM CaCl$_2$ and 1 μM ZnSO4. A concentration of MMP inhibitor of the present invention was tested (1 microMolar) in duplicate runs. Catalytic domain of MMP-9 (human recombinant) enzyme (10 nanoMolar) was added to the compound solution. The mixture of enzyme and compound in assay buffer was then thoroughly mixed and incubated for 60 minutes at 37° C. Upon the completion of incubation, the assay was started by the addition of 10 μM of fluorescent substrate DNP-Pro-Cha-Gly-Cys(Me)-His-Ala-Lys(N-Me-Abz)-NH2 [Cha=β-cyclohexylalanyl; Abz=2-aminobenzoyl (anthraniloyl)] (Kd ~7 microMolar). The fluorescent product, DnpPChaG, was then measured at excitation of 365 nm and emission 450 nm by an automatic plate multireader at 37° C. A positive control was separately run using the broad spectrum MMP inhibitor GM6001 as a control compound (MMP-9 IC50=0.2 nanoMolar). Table 14 summarizes the results of the inhibition study.

TABLE 14

Percent MMP-9 Inhibition

| Compound ID# | Compound Concentration | Substrate | Substrate Concentration | Average Percent Inhibition |
|---|---|---|---|---|
| 5 | 1 microMolar | DNP-Pro-Cha-Gly-Cys(Me)-His-Ala-Lys(N-Me-Abz)-NH2 | 10 microMolar | 82% |
| 118 | 1 microMolar | DNP-Pro-Cha-Gly-Cys(Me)-His-Ala-Lys(N-Me-Abz)-NH2 | 10 microMolar | 78% |

Example 132

Assay for Determining MMP-1 Inhibition

If one were interested in measuring the MMP-1 inhibitor activity of the MMP inhibitors of the present invention one could use the method of Knight (Knight, C. G. et. al, *FEBS LETT.* 296 (3), (1992), 263-266), in which an assay buffer comprising of 50 mM Tris-HCl, pH 7.6, 200 mM NaCl, 5 mM CaCl$_2$ and 1 μM ZnSO4 is used. A single concentration could be tested (i.e., 1 microMolar) in duplicate runs. Catalytic domain of MMP-1 (human recombinant) enzyme could then be added to the compound solution. The mixture of enzyme and compound in assay buffer would then be thoroughly mixed and incubated for 60 minutes at 37° C. Upon the completion of incubation, the assay would then be started by the addition of 10 μM of fluorescent substrate DNP-Pro-Cha-Gly-Cys(Me)-His-Ala-Lys(N-Me-Abz)-NH2 [Cha=β-cyclohexylalanyl; Abz=2-aminobenzoyl (anthraniloyl)] (10 μM). The fluorescent product, DnpPChaG, could then be measured at an excitation wavelength of 365 nm and emission wavelength of 450 nm using an automatic plate multireader at 37° C. A positive control could also be run separately using the broad spectrum MMP inhibitor Tyr-hydroxamic acid as a control compound.

Example 133

Assay for Determining MMP-7 Inhibition

If one were interested in measuring the MMP-7 inhibitor activity of the MMP inhibitors of the present invention one could use the method of Knight (Knight, C. G. et. al, *FEBS LETT.* 296 (3), (1992), 263-266), in which an assay buffer comprising of 50 mM Tris-HCl, pH 7.6, 200 mM NaCl, 5 mM CaCl$_2$ and 1 μM ZnSO4 is used. A single concentration could be tested (i.e., 1 microMolar) in duplicate runs. Catalytic domain of MMP-7 (human recombinant) enzyme could then be added to the compound solution. The mixture of enzyme and compound in assay buffer would then be thoroughly mixed and incubated for 60 minutes at 37° C. Upon the completion of incubation, the assay would then be started by the addition of 10 μM of fluorescent substrate Mca-P-L-G-L-Dpa-A-R-NH2. The fluorescent product, McaPLG, could then be measured at an excitation wavelength of 355 nm and emission wavelength of 405 nm using an automatic plate multireader at 37° C. A positive control could also be run separately using the broad spectrum MMP inhibitor Tyr-hydroxamic acid as a control compound.

Example 134

Assay for Determining MMP-3 Inhibition

If one were interested in measuring the MMP-3 inhibitor activity of the MMP inhibitors of the present invention one could use the method of Knight (Knight, C. G. et. al, *FEBS LETT.* 296 (3), (1992), 263-266), in which an assay buffer comprising of 50 mM Tris-HCl, pH 7.6, 200 mM NaCl, 5 mM CaCl$_2$ and 1 μM ZnSO4 is used. A single concentration could be tested (i.e., 1 microMolar) in duplicate runs. Catalytic domain of MMP-3 (human recombinant) enzyme could then be added to the compound solution. The mixture of enzyme and compound in assay buffer would then be thoroughly mixed and incubated for 60 minutes at 37° C. Upon the completion of incubation, the assay would then be started by the addition of 10 μM of fluorescent substrate McaRPK-PVENvalWRK(Dnp)NH2. The fluorescent product, McaRPK, could then be measured at an excitation wavelength of 355 nm and emission wavelength of 405 nm using an automatic plate multireader at 37° C. A positive control could also be run separately using the broad spectrum MMP inhibitor Tyr-hydroxamic acid as a control compound.

Example 135

Assay for Determining MMP-12 Inhibition

MMP-12 inhibitor activity can be carried out by first separating the cleaved and uncleaved substrates by charge via electrophoretic mobility shift and then measuring the fluorescence of the separated products and comparing them with control reactions to determine inhibition of enzyme activity. One could then run the MMP-12 assay using an assay buffer comprised of 100 mM HEPES, pH 7.5, 0.01% Brij-35, 1.5 mM NaCl and 2 mM $CaCl_2$. A single inhibitor concentration could be tested (i.e. 1 microMolar) in duplicate runs. The reaction could be started by first the addition of substrate and then incubating the reaction mixture for 1 hour at room temperature. The reaction could then be terminated via the addition of a stop buffer consisting of 100 mM HEPES (pH 7.5), 30 mM EDTA, 0.015% Brij-35, and 5% DMSO. A positive control could then be run separately using the broad spectrum MMP inhibitor GM6001 as a control compound.

Example 136

Assay for Determining MMP-13 Inhibition

If one were interested in measuring the MMP-13 inhibitor activity of the MMP inhibitors of the present invention one could use the method of Knight (Knight, C. G. et. al, *FEBS LETT.* 296 (3), (1992), 263-266), in which an assay buffer comprising of 50 mM Tris-HCl, pH 7.6, 200 mM NaCl, 5 mM $CaCl_2$ and 1 μM ZnSO4 is used. A single concentration could be tested (i.e., 1 microMolar) in duplicate runs. Catalytic domain of MMP-13 (human recombinant) enzyme could then be added to the compound solution. The mixture of enzyme and compound in assay buffer would then be thoroughly mixed and incubated for 60 minutes at 37° C. Upon the completion of incubation, the assay would then be started by the addition of 10 μM of fluorescent substrate Mca-β-L-G-L-Dpa-A-R-NH2. The fluorescent product, McaPLG, could then be measured at an excitation wavelength of 355 nm and emission wavelength of 405 nm using an automatic plate multireader at 37° C. A positive control could also be run separately using the broad spectrum MMP inhibitor Tyr-hydroxamic acid as a control compound.

What is claimed is:
1. A compound having Formula (II):

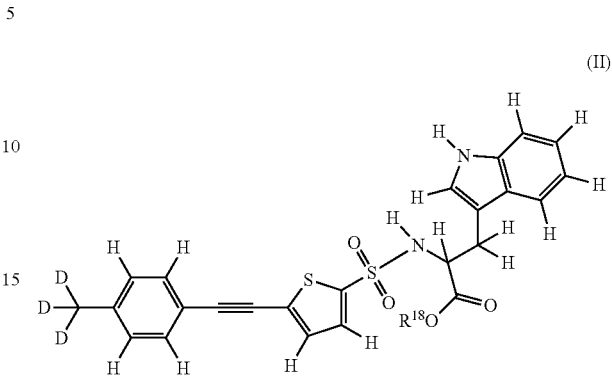

(II)

wherein:
$R^{18}$ is independently selected from the group consisting of hydrogen, deuterium, alkyl, deuteroalkyl, sodium, potassium; or N-oxides, pharmaceutically acceptable salts, prodrugs, formulations, polymorphs, tautomers, racemic mixtures or stereoisomers thereof.

2. A compound selected from the group consisting of:

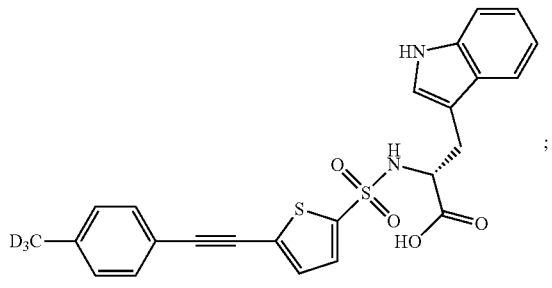

118 or a pharmaceutically acceptable salt thereof.

* * * * *